US011491091B2

(12) United States Patent
Küper et al.

(10) Patent No.: US 11,491,091 B2
(45) Date of Patent: Nov. 8, 2022

(54) COOLING PRODUCT

(71) Applicant: SYMRISE AG, Holzminden (DE)

(72) Inventors: Thomas Küper, Reken (DE); Heiko Oertling, Lausanne (CH); Sabine Lange, Holzminden (DE)

(73) Assignee: Symrise AG, Holzminden (DE)

( * ) Notice: Subject to any disclaimer, the term of this patent is extended or adjusted under 35 U.S.C. 154(b) by 145 days.

(21) Appl. No.: 16/205,409

(22) Filed: Nov. 30, 2018

(65) Prior Publication Data

US 2019/0099342 A1    Apr. 4, 2019

Related U.S. Application Data

(62) Division of application No. 13/704,037, filed as application No. PCT/EP2010/066272 on Oct. 27, 2010, now abandoned.

(30) Foreign Application Priority Data

Jun. 14, 2010  (EP) ..................................... 10165901

(51) Int. Cl.
*A61K 8/34*    (2006.01)
*A61K 8/42*    (2006.01)
(Continued)

(52) U.S. Cl.
CPC ................ *A61K 8/345* (2013.01); *A61K 8/42* (2013.01); *A61Q 5/00* (2013.01); *A61Q 19/00* (2013.01); *A61K 2800/244* (2013.01)

(58) Field of Classification Search
CPC .... A61K 2800/244; A61K 8/345; A61K 8/42; A61K 2300/00; A61K 47/10; A61K 8/046; A61K 8/365; A61K 8/73; A61K 9/0014; A61K 9/122; A61K 2800/24; A61K 2800/242; A61K 2800/30; A61K 31/70; A61K 31/716; A61K 36/00; A61K 36/14; A61K 36/17; A61K 36/185; A61K 36/24; A61K 36/48; A61K 36/53; A61K 36/704; A61K 36/71; A61K 45/06; A61K 47/06; A61K 47/14; A61K 47/26; A61K 47/34; A61K 47/36; A61K 47/38; A61K 47/44; A61K 8/34; A61K 8/347; A61K 8/362; A61K 8/37; A61K 8/43; A61K 8/49; A61K 8/4993; A61K 8/731; A61K 8/736; A61K 8/8152; A61K 8/8158; A61K 8/86; A61K 8/87; A61K 8/922; A61K 9/107; A61K 9/12; A61K 2800/21; A61K 2800/413; A61K 2800/70; A61K 2800/75; A61K 2800/91; A61K 31/015; A61K 31/07; A61K 31/137; A61K 31/155; A61K 31/167; A61K 31/17; A61K 31/19; A61K 31/196; A61K 31/20; A61K 31/202; A61K 31/203; A61K 31/351; A61K 31/41; A61K 31/415; A61K 31/4164; A61K 31/4174; A61K 31/425; A61K 31/433; A61K 31/436; A61K 31/44; A61K 31/4412; A61K 31/4422; A61K 31/496; A61K 31/497; A61K 31/505; A61K 31/506; A61K 31/52; A61K 31/522; A61K 31/535; A61K 31/5375; A61K 31/551; A61K 31/554; A61K 31/56; A61K 31/567; A61K 31/568; A61K 31/573; A61K 31/575; A61K 31/7036; A61K 31/7048; A61K 35/04; A61K 38/00; A61K 38/12; A61K 38/13; A61K 38/212; A61K 45/00; A61K 47/12; A61K 47/18; A61K 47/20; A61K 47/22; A61K 47/24; A61K 47/32; A61K 47/46; A61K 8/02; A61K 8/06; A61K 8/062; A61K 8/064; A61K 8/068; A61K 8/31; A61K 8/342; A61K 8/361; A61K 8/375; A61K 8/39; A61K 8/494; A61K 8/4953; A61K 8/4973; A61K 8/498; A61K 8/60; A61K 8/602; A61K 8/671; A61K 8/737; A61K 8/8141; A61K 8/8147; A61K 8/8176; A61K 8/891; A61K 8/965; A61K 8/97; A61K 8/9717; A61K 8/9761; A61K 8/9767; A61K 8/9771; A61K 8/9789;
(Continued)

(56) References Cited

U.S. PATENT DOCUMENTS 4,136,163 A    1/1979 Watson et al.
5,405,604 A    4/1995 Hall
(Continued)

FOREIGN PATENT DOCUMENTS

DE    2608226 A1    9/1977
EP    1639993 A1    3/2006
(Continued)

OTHER PUBLICATIONS

Database CA [Online] Chemical Abstracts Service, Columbus, Ohio,US; Jan. 16, 2004 (Jan. 16, 2004), Sasaki, Tatsuo et al., "Oral Compositions Containing Alkanediols and Monoterpenes and Antiseptic Compositions Containing Alkanediols and Menthol", XP002622637, retrieved from STN Database accession No. 2004:36936 * abstract -& JP 2004 010497 A (Lion Corp., Japan) Jan. 15, 2004.
(Continued)

*Primary Examiner* — Audrea B Coniglio
(74) *Attorney, Agent, or Firm* — Dilworth & Barrese, LLP

(57) ABSTRACT

There are provided herein cosmetic and sanitary products comprising physiologic cooling compounds, selected 1,2-alkanediols, and tensides and/or UV filters.

5 Claims, No Drawings

(51) Int. Cl.
*A61Q 19/00* (2006.01)
*A61Q 5/00* (2006.01)

(58) Field of Classification Search
CPC ...... A61K 8/9794; A61K 9/00; A61K 9/0007;
A61K 9/0034; A61K 9/006; A61K 9/10;
A61K 9/1075; A61K 9/124; A61K
9/7015; A01N 53/00; A01N 65/12; A01N
43/30; A01N 57/12; A01N 65/08; A01N
25/16; A01N 65/00; A01N 2300/00;
A01N 25/04; A01N 25/06; A01N 31/02;
A01N 37/04; A01N 43/36; A01N 43/40;
A01N 43/50; A01N 47/44; A01N 65/28;
A01N 25/02; A01N 25/30; A61Q 19/00;
A61Q 5/00; A61Q 19/08; A61Q 11/00;
A61Q 19/02; A61Q 17/02; A61Q 17/04;
A61Q 19/007; A61Q 19/06; A61Q 1/10;
A61Q 1/14; A61Q 5/02; A61Q 5/12;
A61Q 7/00; A61Q 15/00; A61Q 17/00;
A61Q 17/005; A61Q 19/002; A61Q
19/004; A61Q 19/008; A61Q 19/04;
A61Q 19/10; A61Q 5/006; A61Q 7/02
USPC .......................................................... 474/70
See application file for complete search history.

(56) References Cited

U.S. PATENT DOCUMENTS

| 9,029,415 B2 | 5/2015 | Küper et al. |
| 2006/0110416 A1 | 5/2006 | Ryles et al. |
| 2007/0225378 A1 | 9/2007 | Ishida et al. |
| 2008/0253973 A1* | 10/2008 | Tamarkin ............. A61K 8/8152 424/47 |
| 2009/0054520 A1* | 2/2009 | Surburg ................... A61K 8/49 514/529 |
| 2009/0156563 A1* | 6/2009 | Baschong ............. A61K 8/347 514/159 |
| 2010/0086498 A1 | 4/2010 | Haught et al. |
| 2010/0138531 A1 | 7/2010 | Johncock et al. |
| 2011/0305657 A1 | 12/2011 | Kuper et al. |

FOREIGN PATENT DOCUMENTS

| EP | 1958627 A2 | 8/2008 | |
| EP | 2033688 A2 | 3/2009 | |
| JP | 2004010497 A | 1/2004 | |
| WO | WO-0213776 A2 | 2/2002 | |
| WO | WO-2006/069953 A1 | 7/2006 | |
| WO | 2009087242 A2 | 7/2009 | |
| WO | WO-2009087242 A2 * | 7/2009 | ............. A23L 33/10 |

OTHER PUBLICATIONS

Erman MB, "Cooling Agents and Skin Care Applications", Cosmetics & Toiletries, vol. 120, No. 5. 2005 . pp. 105-118, XP009051809.
Watson, HR et al., "New Compounds with the Menthol Cooling Effect," Journal of the Society Cosmetic Chemists, Society of Cosmetic Chemists, vol. 29, No. 1, 1978, pp. 185-200, XP009045124.
International search report with references cited and written opinion under Rule 43 PCT attached to the search report, International Application No. PCT/EP2010/066272, filed Oct. 27, 2010.
European Search Report, European Application No. 10165901.9, dated Feb. 28, 2011.
Final Office Action issued in U.S. Appl. No. 13/159,925 (US Publication No. US 2011/03056571), dated Apr. 28, 2014.

* cited by examiner

COOLING PRODUCT

CROSS-REFERENCE TO RELATED APPLICATIONS

This application filed Nov. 30, 2018 is a division of U.S. application Ser. No. 13/704,037, filed Apr. 23, 2013, which is a national stage entry of PCT/EP10/66272 with an international filing date of Oct. 27, 2010 and claims foreign priority to EP10165901.9 filed Jun. 14, 2010.

AREA OF INVENTION

The invention relates to a use of one, two, three or more certain polyols for enhancing the cooling effect of a cooling substance. It further relates to a cooling mixture comprising a cooling effect enhancing polyol and a cooling substance consisting of one or more physiologically cooling compounds and optionally further compounds having an additional enhancing effect on the cooling effect of the substance. Moreover the invention relates to a method for producing a corresponding cooling mixture and a method for generating an enhanced cooling effect of a cooling substance on the skin or a mucous membrane.

BACKGROUND OF THE INVENTION

Cooling substances are used in the area of personal care for application onto the skin, hair and mucous membranes. Such applications include lotions and creams, skin cleansers, shampoos, hair conditioners, cleaning tissues, sanitary towels, tampons, nappies as well as other cosmetic products such as lipsticks or Eau de Toilette. A multiplicity of cooling substances of natural and synthetic origin has been described. The most well known substance out of these is menthol, in particular l-menthol, which was initially found in peppermint oil. Menthol binds to the TRPM8 (Transient Receptor Potential Melastatin 8) receptor also known under the designation of CMR (Cold Menthol Receptor 1). This receptor belongs to the family of TRPS (Transient Receptor Potential Ion Channels) and is expressed in specific peripheral neurons, where it forms a pore consisting of four protein monomers. Low temperatures as well as the binding of cooling substances to the channel will open the latter and will thus allow calcium and sodium ions to enter through the membrane. This flow of ions results in a depolarization of the membrane and a generation of an action potential which will be converted in the brain into a sensation of cold (Clapham D E et al 2005, Pharmacological reviews, 57 (4), 427-450; Peier A M et al 2005, Cell, 108 (5), 705-15). Several menthol derivatives have been described, which induced the opening of TRPM8 (British Patent 1971 #1315761 Watson H. R., J. Soc. Cosmet. Chem, 29, 1978, 185-200; Furrer S. M., Chem. Percept. 1, 2008, 119-126), however, there are also structures which have a cooling effect and are not based on menthol, such as Icilin (Wei E. T., J. Pharm. Pharmacol. 35, 1983, 110-112; WO 2004/026840), WS-23 or substances such as mentioned in WO 2007/019719.

Relevant Prior Art

Activators of TRPM8 may have a repellent effect on insects (WO 2002/015692, WO 2004/000023, US 2004/0028714) and may also have calming properties during the treatment of inflammation-induced pain and hyperalgesia as well as a hyperactive bladder (Beck B. Cell Calcium, 41, 2007, 285-294; Levine J. D. Biochim. Biophys. Acta, Mol. Basis. Dis. 1772, 2007, 989-1003; Mukerji G., BMC Urology 6, 2006, 6; US 2003/0207904; US 2005/6893626, Lashinger E S. Am. J. Physiol. Renal Physiol. 295, 2008, 303-810).

A number of studies could further show that some activators of TRPM8 have a growth inhibiting effect on tumors (Slominski A., Am. J. Physiol. 295, 2008, 293-295; Yamamura H, to Am. J. Physiol. Cell Physiol. 295, 2008, 296-301).

Due to their close structural relationship to menthol, many cooling substances have an odor similar to that of mint and are therefore not suitable for topical application. In addition, a high concentration of more than 3% has to be used in many physiological cooling substances, in order to induce a tangible cooling effect. High concentrations of cooling substances may cause undesired side effects such as stinging and burning on the skin (Warner G., Brain, 2004, 127, 1159-1171; Green B G, Behav Brain Res, 2007, 176, 284-291).

Object of the Invention

In the light of this background it is the object of the present invention to provide a way of providing a cooling sensation of a given strength, wherein the concentration of cooling substance (i.e. physiologically cooling compounds) is reduced. At the same time this way should be open for topical applications and applications of care products.

BRIEF DESCRIPTION OF THE INVENTION

This object is achieved by a use of one, two, three or more polyols selected from the group (A) consisting of branched or unbranched alkanediols and branched or unbranched alkanetriols each having 3-12 carbon atoms for enhancing the cooling effect of a cooling substance, the substance consisting of a physiologically cooling compound or a mixture of 2, 3, 4, 5, 6, 7, 8, 9, 10 or more physiologically cooling compounds on the skin or a mucous membrane.

Because of the priority situation for this application the solution of the above object of the invention may be also formulated as a use of one, two, three or more polyols selected from the group A consisting of branched or unbranched alkanediols and branched or unbranched alkanetriols each having 3-12 carbon atoms for enhancing the cooling effect of a cooling substance, the cooling substance consisting of (i)  5-methyl-2-(propane-2-yl)cyclohexyl-N-ethyloxamate (formula I)

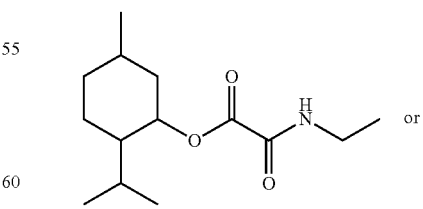

(ii) a physiologically cooling compound different to 5-methyl-2-(propane-2-yl)cyclohexyl-N-ethyloxamate or (iii) a mixture of 2, 3, 4, 5, 6, 7, 8, 9, 10 or more physiologically cooling compounds different to 5-methyl-2-(propane-2-yl)cyclohexyl-N-ethyloxamate or (iv) a mixture of one, 2, 3, 4, 5, 6, 7, 8, 9 or more physiologically cooling compounds with 5-methyl-2-(propane-2-yl)cyclohexyl-N-ethyloxamate on the skin or a mucous membrane.

There are many physiologically cooling compounds known from the state of the art. Surprisingly, the inventors have now been able to show that the combination of these compounds with branched or unbranched alkanediols or branched or unbranched alkanetriols each having 3 to 12 carbon atoms results in an enhancement of the cooling effect in the case of a topical application. This is not an additive effect since the corresponding diols and triols do not possess a cooling effect.

Physiologically cooling compounds in terms of the present text are compounds that are able to provide a cooling sensation case that a sufficient amount is topically applicated. Of course it is possible within the scope of the invention that for the use according to the invention an amount of cooling substance is used that is so low that the cooling effect may be perceived only as a result of an enhancement by the corresponding polyols (and optionally by an enhancement of further compounds, see below).

In case of doubt, the perceptibility of the cooling effect is to be determined by means of a panel test wherein the corresponding mixture is applied onto the skin of at least 10 test persons. If in the course of this, preferably in combination with a blind test, 90% of the test persons confirm a cooling effect, then this will preferably correspond to the criteria for the presence of a corresponding effect.

Topical applications in terms of the present text are applications where the corresponding active substance or the combination of active substances is brought into contact with the skin or with a mucous membrane. It is especially preferred that the evaluation of a cooling effect and its enhancement is made analog to the application example presented below.

Preferred physiologically cooling compounds are selected from the group consisting of 5-methyl-2-(propane-2-yl)cyclohexyl-N-ethyloxamate, N-ethyl-p-menthane carboxamide (WS-3, also referred to as menthane-3-carboxylic acid-N-ethyl amide), N-2,3-trimethyl-2-isopropyl butane amide (WS-23), menthyl lactate (Frescolat® ML), menthone glycerine acetal (Frescolat® MGA), mono-menthyl succinate (Physcool®), mono-menthyl glutarate, O-menthyl-glycerine, menthyl-N,N-dimethyl succinamate, N-(4-cyano methyl phenyl)-p-menthane carboxamide, N-(2-(pyridin-2-yl)ethyl)-3-p-menthane carboxamide, menthol and menthol derivatives (e.g. L-menthol, D-menthol, racemic menthol, isomenthol, neoisomenthol, neomenthol) menthyl ether (e.g. (l-menthoxy)-1,2-propanediol, (l-menthoxy)-2-methyl-1,2-propanediol, 1-menthyl-methyl ether), menthyl ester (e.g. menthyl formiate, menthyl acetate, menthyl isobutyrate, menthyl lactates, L-menthyl-L-lactate, L-menthyl-D-lactate, menthyl-(2-methoxy)acetate, menthyl-(2-methoxy ethoxy)acetate, menthyl pyroglutamate), N-(4-cyano methyl phenyl)-p-menthane carboxamide, N-(2-(pyridin-2-yl)ethyl)-3-p-menthane carboxamides, menthyl carbonates (e.g. menthyl propylene glycol carbonate, menthyl ethylene glycol carbonate, menthyl glycerine carbonate or mixtures thereof), the semi-esters of mentholes with a dicarboxylic acid or their derivatives (e.g. mono-menthyl succinate, mono-menthyl glutarate, mono-menthyl malonate, O-menthyl succinic acid ester-N,N-(dimethyl)amide, O-menthyl succinic acid ester amide), menthane carboxylic acid amide (e.g. menthane carboxylic acid-N-ethylamid [WS3], N.alpha.-(menthane-carbonyl)glycine ethyl ester [WS5], menthane carboxylic acid-N-(4-cyanophenyl)amide, menthane carboxylic acid-N-(alkoxyalkyl)amide), menthone and menthone derivatives (e.g. L-menthone glycerine ketal), 2,3-dimethyl-2-(2-propyl)-butyric acid derivatives (e.g. 2,3-dimethyl-2-(2-propyl)-butyric acid-N-methyl amide [WS23]), isopulegol or its esters (1e(−)-isopulegol,1-(−)-isopulegol acetate), menthane derivatives (e.g. p-menthane-3,8-diol), N-(4-cyano methyl phenyl)-p-menthane carboxamides, N-(2-(pyridin-2-yl)ethyl)-3-p-menthane carboxamides, cubebol or synthetic or natural mixtures containing cubebol, pyrrolidone derivates of cycloalkyl dione derivatives (e.g. 3-methyl-2(1-pyrrolidinyl)-2-cyclopentane-1-one) or tetrahydropyrimidine-2-ones (e.g. Icilin or related compounds such as those described in WO 2004/026840).

Further preferred cooling compounds are N-(4-cyano methyl phenyl)-p-menthane carboxamide, N-(2-(pyridin-2-yl)ethyl)-3-p-menthane carboxamides, menthyl ether (e.g. (l-menthoxy)-1,2-propanediol, (l-menthoxy)-2-methyl-1,2-propanediol), more polar menthyl esters (e.g. menthyl lactates, L-menthyl-L-lactate, L-menthyl-D-lactate, menthyl-(2-methoxy)acetate, menthyl-(2-methoxy ethoxy)acetate, menthyl pyroglutamate), menthyl carbonates (e.g. menthyl propylene glycol carbonate, menthyl ethylene glycol carbonate, menthyl glycerine carbonate), the semi-esters of menthols with a dicarboxylic acid or the derivatives thereof (e.g. mono-menthyl succinate, mono-menthyl glutarate, mono-menthyl malonate, O-menthyl succinic acid ester-N, N-(dimethyl)amide, O-menthyl succinic acid ester amide), menthane carboxylic acid amides not according to the invention (e.g. menthane carboxylic acid-N-ethylamide [WS3], N.alpha.-(menthane carbonyl)glycine ethyl ester [WS5], menthane carboxylic acid-N-(4-cyanophenyl)amide, menthane carboxylic acid-N-(alkoxyalkyl)amide), menthone derivatives (e.g. L-menthone glycerine ketal), 2,3-dimethyl-2-(2-propyl)-butyric acid derivatives (e.g. 2,3-dimethyl-2-(2-propyl)-butyric acid-N-methyl amide), pyrrolidone derivatives of cycloalkyl dione derivatives (e.g. 3-methyl-2(1-pyrrolidinyl)-2-cyclopentene-1-one) or tetrahydropyrimidine-2-one (e.g. Icilin or related compounds such as those described in WO 2004/026840). 3,4-methylendioxycinnamic acid-N-cyclohexyl-N-2-pyridylamide, isopropyl-(5-methoxy-2-pyridin-2-yl-pyrimidin-4-yl)-amine, 3,4,6,7,11b,12-hexahydro-3,3-dimethyl-Spiro[13H-dibenzo[af]quinolizine-1-3,2'-[1,3]dithiolan]-1(2H)-one, 5,6,10b,11-tetrahydro-3-methyl-Spiro[12H-benzo[a]furo[3,4-f]quinolizine-1-2,2'-[1,3]dithiolan]-1(3H)-one. Most preferred as cooling compounds are compounds selected from the group consisting of 5-methyl-2-(propane-2-yl)cyclohexyl-N-ethyloxamate, N-ethyl-p-menthane carboxamide (WS-3, also referred to as menthane-3-carboxylic acid-N-ethyl amide), menthyl lactate (Frescolat® ML), menthane glycerine acetal (Frescolat® MGA), N-(4-cyano methyl phenyl)-p-menthane carboxamide and (l-menthoxy)-1,2-propanediol.

Preferred for a use according to the invention is that a or the polyol or several or all of the polyols of group A is or are selected from the group consisting of the branched or Unbranched alkanediols having 3 to 12 carbon atoms.

The preferred polyols show an improved enhancement effect on the effect of cooling substances. Preferred polyols for use according to the invention are discussed below.

More preferred is the use according to the invention wherein the ratio between amount by weight of the cooling substance and the amount by weight of the polyol or the polyols of group A taken together is 1:20 to 1:0.1, preferably 1:10 to 1:0.5 and most preferably 1:5 to 1:1.

In these preferred amount ratios the cooling enhancing effect elicited by the use according to the invention can be achieved in many mixtures best.

In the use according to the invention cooling mixtures are made by mixing the compounds to be used. Accordingly, the following described mixtures are part of the invention, too. It is a matter of course that the use may be carried out in connection with the mixtures and especially preferred mixtures according to the invention, too. The same is valid for cosmetic compositions according to the invention and sanitary articles according to the invention in particular in the respective preferred embodiments which are described below.

Accordingly a part of the invention is cooling mixture comprising or consisting of
(i) 5-methyl-2-(propane-2-yl)cyclohexyl-N-ethyloxamate (formula I)

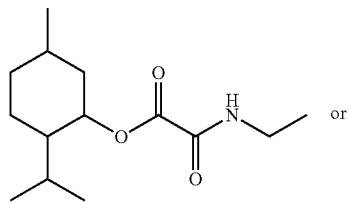 [SMILES: CCNC(=O)C(=O)OC1CC(C)CCC1C(C)C]

or (ii) a physiologically cooling compound different to 5-methyl-2-(propane-2-yl)cyclohexyl-N-ethyloxamate or
(iii) a mixture of 2, 3, 4, 5, 6, 7, 8, 9, 10 or more physiologically cooling compounds different to 5-methyl-2-(propane-2-yl)cyclohexyl-N-ethyloxamate or
(iv) a mixture of one, 2, 3, 4, 5, 6, 7, 8, 9 or more physiologically cooling compounds with 5-methyl-2-(propane-2-yl)cyclohexyl-N-ethyloxamate and
(b) one, two, three or more polyols selected from the group A consisting of branched or unbranched alkanediols and branched or unbranched alkanetriols each having 3-12 carbon atoms.

The cooling mixture according to the invention shows an enhanced cooling effect of the cooling substance (i.e. the cooling compound or the cooling compounds from which the cooling substance consists). It has to be noted that the enhancing effect exhibited by the alkandiol or the alkantriol can be further enhanced by certain substances/compounds which will be described below.

In case that the cooling composition comprises 5-methyl-2-(propane-2-yl)cyclohexyl-N-ethyloxamate it is preferred at least part of this compound is present in the (1R,2S,5R) configuration (formula II):

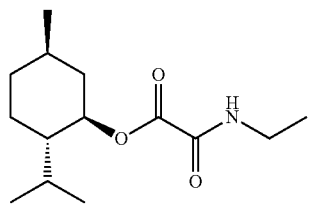 [SMILES: CCNC(=O)C(=O)O[C@@H]1C[C@H](C)CC[C@H]1C(C)C]

The 1R,2S,5R isomer of 5-methyl-2-(propane-2-yl)cyclohexyl-N-ethyloxamate is particularly accessible for an enhancement of the cooling effect and may in addition by synthesized in an economical manner via L-menthol as a starting compound.

Correspondingly, a cooling mixture according to the invention is preferred, wherein the proportion of 5-methyl-2-(propan-2-yl)cyclohexyl-N-ethyloxamate present in the (1R,2S,5R) configuration in relation to the overall proportion of 5-methyl-2-(propane-2-yl)cyclohexyl-N-ethyloxamate is .gtoreq. 45%, preferably .gtoreq. 70% and particularly probably .gtoreq. 97%.

According to the invention, as an alternative or in addition to the preferred embodiments, a cooling mixture according to the invention is preferred, wherein the ratio between the amount of cooling substance (especially of 5-methyl-2-(propane-2-yl)cyclohexyl-N-ethyloxamate) and the amount of substance of the polyol or of the polyols of group A taken together is 1:20 to 1:0.1, preferably 1:10 to 1:0.5 and particularly preferably 1:5 to 1:1.

In terms of the invention it is further preferred if in the cooling mixture according to the invention, a or the polyol or several or all of the polyols of group A is or are selected from the group consisting of branched or unbranched alkanediols having 3 to 12 carbon atoms.

It is further preferred for the cooling mixture according to the invention, if in a or the alkanepolyol of group A or in several or all of the alkanepolyols of group A both or at least two of the hydroxyl groups are positioned vicinal to one another.

In addition, a cooling mixture according to the invention is preferred wherein exclusively one or more branched or unbranched 1,2-alkanediols having 5 to 12 carbon atoms are used as component (b).

The last-mentioned preferred variants of the cooling mixture each result, either alone or in a combination of the preferred features, in an improved enhancing effect for the actual active cooling substance 5-methyl-2-(propane-2-yl) cyclohexyl-N-ethyloxamate. Preferred to diols or triols for the cooling mixture as component (b) or as part of component (b) are 1,2-pentanediol, 1,2-hexanediol, 1,2-heptanediol, 1,2-octanediol, 1,2-nonanediol, 1,2-decanediol, 1,2-dodecanediol and glycerol.

What is particularly preferred in this context is that component (b) in the cooling mixture comprises or consists of n-1,2-pentanediol.

Provided the cooling mixture according to the invention comprises n-1,2-pentanediol, it is preferred if the ratio between the amount of substance of 5-methyl-2-(propane-2-yl)cyclohexy-N-ethyloxamate and the amount of substance of n-1,2-pentanediol is 1:20 to 1:0.1, preferably 1:10 to 1:0.5 and particularly preferably 1:5 to 1:1.

In the case of this quantity ratio of substances, n-1,2-pentanediol (also as pentylene glycol) will develop its enhancing effect especially well. Moreover, corresponding ratios are to be regarded as especially economical with regard to their cost-benefit factor.

Further preferred is a cooling mixture according to the invention, which as a further component comprises a compound having an antagonistic effect on the heat receptors of the skin or of mucous membranes and thus reduces the sensation of heat. Trans-4-tert.-butylcyclohexanol is preferably used as such a compound, Preferably, these compounds, and in particular trans-4-tert.-butylcyclohexanol, are used in a quantity ratio of substances relative to the sum of diols and triols of 100:1 to 1:1000, more preferably of 10:1 to 1:100 and particularly preferably of 1:1 to 1:10.

By adding corresponding heat receptor antagonists it is possible to enhance the perceived cooling effect mediated via cooling receptors subjectively even further by reducing the sensitivity of the heat receptors.

Surprisingly, the inventors have found that the enhanced cooling effect of the above cooling mixtures according to the invention and the above use according to the invention can be further enhanced by certain groups of compounds.

Accordingly, a cooling mixture according to the invention is preferred that the comprises in addition to the component a) (cooling substance as described above) and component b) (polyol) a further enhancing substance for the cooling effect of component a) This further enhancing substance is preferably one or more compounds selected from silicon oils (group B) and/or terpenes (Group C) and/or [0040] musk compounds (group D) and/or abrasives (group E) and/or tensides (group F).

Surprisingly, it has turned out that the different compounds of groups B-F are able to enhance the cooling effect of a physiologically cooling substance. Without being bound to a theory the reason may be that the members of groups B-F in some kind influence the barrier of the skin so that the cooling receptors located in the skin (or a mucous membrane) are better available for the cooling substance. Maybe this is especially valid for compounds of group C-F. In the case of silicones and maybe some compounds of the other groups mentioned above there may be an additional occlusion effect which results in an improved exposure of the skin or the mucous membrane to the cooling substance. In addition to that silicones improve skin moistening which also may improve the penetration of cooling substances, Regarding tensides it has been known that these compounds improve for many different compounds the penetration ability for the outer layers of the skin. However, it has to be noted that not each modulator of penetration ability is also a cooling effect enhancer.

Preferred compounds exhibiting an additional enhancing effect on the cooling sensation exhibited by the cooling substance are described in the following:

Preferably one or more silicons (group B) are selected from the group consisting of: Acefylline Methylsilanol Mannuronate, Acetylmethionyl Methylsilanol Elastinate Acrylates/Behenyl, Acrylate/Dimethicone Methacrylate Copolymer, Acrylates/Behenyl Methacrylate/Dimethicone Methacrylate Copolymer, Acrylates/Bis-Hydroxypropyl Dimethicone Cross-polymer, Acrylates/Dimethicone Copolymer, Acrylates/Dimethicone Methacrylate/Ethylhexyl Acrylate Copolymer, Acrylates/Dimethiconol Acrylate Copolymer, Acrylates/Ethylhexyl Acrylate/Dimethicone Methacrylate Copolymer, Acrylates/Octylacrylamide/Diphenyl Amodimethicone Copolymer, Acrylates/Polytrimethylsiloxymethacrylate Copolymer, Acrylates/Propyl Trimethicone Methacrylate Copolymer, Acrylates/Stearyl Acrylate/Dimethicone Methacrylate Copolymer, Acrylates/Tridecyl Acrylate/Triethoxysilylpropyl Methacrylate/Dimethicone Methacrylate Copolymer, Acrylates/Trifluoropropylmethacrylate/Polytrimethyl Siloxymethacrylate Copolymer, Amino Bispropyl Dimethicone, Aminoethylaminopropyl Dimethicone, Aminopropyl Dimethicone, Aminopropyl Phenyl Trimethicone, Aminopropyl Triethoxysilane, Ammonium Dimethicone PEG-7 Sulfate, Amodimethicone, Amodimethicone Hydroxystearate, Amodimethicone/Silsesquioxane Copolymer, Ascorbyl Carboxydecyl Trisiloxane, Ascorbyl Methylsilanol Pectinate, Behenoxy Dimethicone, Behentrimonium Dimethicone PEG-8 Phthalate, Behenyl Dimethicone, Bisamino PEG/PPG-41/3 Aminoethyl PG-Propyl Dimethicone, Bis-Aminopropyl/Ethoxy Aminopropyl Dimethicone, Bis(Butylbenzoate) Diaminotriazine Aminopropyltrisiloxane, Bis-Butyldimethicone Polyglyceryl-3, Bis-Butyloxyamodimethicone/PEG-60 Copolymer, Bis(C13-15 Alkoxy) Hydroxybutamidoamodimethicone, Bis(C13-15 Alkoxy) PG-Amodimethicone, Bis-(C1-8 Alkyl Lauroyl Lysine Decylcarboxamide) Dimethicone, Bis-Cetyl Cetyl Dimethicone, Bis-Cetyl/PEG-8 Cetyl PEG-8 Dimethicone, Bis-Diphenylethyl Disiloxane, Bis-Ethyl Ethyl Methicone, Bis-Gluconamidoethylaminopropyl Dimethicone, Bis-Hydrogen Dimethicone, Bis-Hydroxyethoxypropyl Dimethicone Bis-Hydroxylauryl, Dimethicone/IPDI Copolymer, Bis-Hydroxy/Methoxy Amodimethicone, Bis-Hydroxypropyl Dimethicone Behenate, Bis-Hydroxypropyl Dimethicone/SMDI Copolymer, Bis-Isobutyl PEG-14/Amodimethicone Copolymer, Bis-Isobutyl PEG-15/Amodimethicone Copolymer, Bis-Isobutyl PEG/PPG-20/35/Amodimethicone Copolymer, Bis-Isobutyl PEG/PPG-10/7/Dimethicone Copolymer, Bis-Isobutyl PEG-24/PPG-7/Dimethicone Copolymer, Bis-PEG-1 Dimethicone, Bis-PEG-4 Dimethicone, Bis-PEG-8 Dimethicone, Bis-PEG-12 Dimethicone, Bis-PEG-20 Dimethicone, Bis-PEG-12 Dimethicone Beeswax, Bis-PEG-12 Dimethicone Candelillate, Bis-PEG-15 Dimethicone/IPDI Copolymer, Bis-PEG-15 Methyl Ether Dimethicone, Bis-PEG-18 Methyl Ether Dimethyl Silane, Bis-PEG/PPG-14/14 Dimethicone, Bis-PEG/PPG-15/5 Dimethicone, Bis-PEG/PPG-18/6 Dimethicone, Bis-PEG/PPG-20/20 Dimethicone, Bis-PEG/PPG-16/16 PEG/PPG-16/16 Dimethicone, Bis-PEG/PPG-20/5 PEG/PPG-20/5 Dimethicone, Bisphenylhexamethicone, Bis-Phenylpropyl Dimethicone, Bispolyethylene Dimethicone, Bis-(Polyglyceryl-3 Oxyphenylpropyl) Dimethicone, Bis-(Polyglyceryl-7 Oxyphenylpropyl) Dimethicone, Bis-PPG-15 Dimethicone/IPDI Copolymer, Bis(PPG-7 Undeceneth-21) Dimethicone, Bis-Stearyl Dimethicone, Bis-Trimethoxysilylethyl Tetramethyldisiloxyethyl Dimethicone, Bis-Vinyldimethicone, Bis-VinylDimethicone/Dimethicone Copolymer, Borage Seed Oil PEG-7 Dimethicone Esters, Butyl Acrylate/C6-14 Perfluoroalkylethyl Acrylate/Mercaptopropyl Dimethicone Copolymer, Butyl Acrylate/Hydroxypropyl Dimethicone Acrylate Copolymer, Butyl Dimethicone Acrylate/Cyclohexylmethacrylate/Ethylhexyl Acrylate Copolymer, Butyldimethicone Methacrylate/Methyl Methacrylate Crosspolymer, t-Butyl Dimethyl Silyl Grape Seed Extract, Butyl Polydimethylsiloxyl Ethylene/Propylene/Vinylnorbomene Copolymer, C6-8 Alkyl C3-6 Alkyl Glucoside Dimethicone, C20-24 Alkyl Dimethicone, C24-28 Alkyl Dimethicone, C26-28 Alkyl Dimethicone, C30-45 Alkyl Dimethicone, C30-60 Alkyl Dimethicone, C32 Alkyl Dimethicone, C30-45 Alkyl Dimethicone/Polycyclohexene Oxide Crosspolymer, C26-28 Alkyldimethylsilyl Polypropylsilsesquioxane, C30-45 Alkyldimethylsilyl Polypropylsilsesquioxane, C20-24 Alkyl Methicone, C24-28 Alkyl Methicone, C26-28 Alkyl Methicone, C30-45 Alkyl Methicone, C20-28 Alkyl Perfluorodecylethoxy Dimethicone, C26-54 Alkyl Tetradecyl Dimethicone, Capryl Dimethicone, Caprylyl Dimethicone Ethoxy Glucoside, Caprylyl Methicone, Caprylyl Trimethicone, Carboxydecyl Trisiloxane, Castor Oil Bis-Hydroxypropyl Dimethicone Esters Cerotyl Dimethicone, Cetearyl Dimethicone Crosspolymer, Cetearyl Dimethicone/Vinyl Dimethicone Crosspolymer, Cetearyl Methicone, Cetrimonium Carboxydecyl PEG-8 Dimethicone, Cetrimonium Dimethicone PEG-7 Phthalate, Cetyl Behenyl Dimethicone, Cetyl Dimethicone, Cetyl Dimethicone/Bis-Vinyldimethicone Crosspolymer, Cetyl Hexacosyl Dimethicone, Cetyloxy Dimethicone, Cetyl PEG-8 Dimethicone, Cetyl PEG/PPG-15/15 Butyl Ether Dimethicone, Cetyl PEG/PPG-7/3 Dimethicone, Cetyl PEG/PPG-10/1 Dimethicone, Cetyl Triethylmonium Dimethicone PEG-8 Phthalate, Cetyl Triethylmonium Dimethicone PEG-8 Succinate, Copper Acetyl Tyrosinate Methylsilanol, Copper PCA Methylsilanol, C4-14 Perfluoroalkylethoxy Dimthicone, Cycloethoxymethicone, Cycloheptasiloxane, Cyclohexasiloxane, Cyclomethicone, Cyclopentasiloxane, Cyclophenylmethicone, Cyclotetrasiloxane, Cyclovinylmethicone, Cystine Bis-PG-Propyl Silanetriol, DEA PG-Propyl PEG/PPG-18/21 Dimethicone, Diisostearoyl Trimethylolpropane Siloxy Silicate, Dilauroyl Trimethylolpropane Siloxy Silicate, Dilinoleamidopropyl Dimethylamine Dimethicone PEG-7 Phosphate, Dimethicone, Dimethicone Crosspolymer, Dimethicone Crosspolymer-3, Dimethicone/Divinyldimethicone/Silsesquioxane Crosspolymer, Dimethicone Ethoxy Glucoside, Dimethicone Hydroxypropyl Trimonium Chloride, Dimethicone/Mercaptopropyl Methicone Copolymer, Dimethicone PEG-15 Acetate Dimethicone PEG-8 Adipate, Dimethicone PEG-7 Avocadoate, Dimethicone PEG-8 Avocadoate, Dimethicone PEG-8 Beeswax, Dimethicone PEG-8 Benzoate, Dimethicone PEG-8 Borageate, Dimethicone PEG-7 Cocoate, Dimethicone/PEG-10 Crosspolymer, Dimethicone/PEG-10/15 Crosspolymer, Dimethicone/PEG-15 Crosspolymer, Dimethicone PEG-7 Isostearate, Dimethicone PEG-8 Isostearate, Dimethicone PEG-7 Lactate, Dimethicone PEG-8 Lanolate, Dimethicone PEG-8 Laurate, Dimethicone PEG-8 Meadowfoamate, Dimethicone PEG-7 Octyldodecyl Citrate, Dimethicone PEG-7 Olivate, Dimethicone PEG-8 Olivate, Dimethicone PEG-7 Phosphate, Dimethicone PEG-8 Phosphate, Dimethicone PEG-10 Phosphate, Dimethicone PEG-7 Phthalate, Dimethicone PEG-8 Phthalate, Dimethicone PEG-8 Polyacrylate, Dimethicone PEG/PPG-20/23 Benzoate, Dimethicone PEG/PPG-7/4 Phosphate, Dimethicone PEG/PPG-12/4 Phosphate, Dimethicone PEG-7 Succinate, Dimethicone PEG-8 Succinate, Dimethicone PEG-7 Sulfate, Dimethicone PEG-7 Undecylenate, Dimethicone PG-Diethylmonium Chloride, Dimethicone/Phenyl Vinyl Dimethicone Crosspolymer, Dimethicone/Polyglycerin-3 Crosspolymer, Dimethicone/PPG-20 Crosspolymer, Dimethicone Propylethylenediamine Behenate, Dimethicone Propyl PG-Betaine, Dimethicone/Silsesquioxane Copolymer, Dimethicone Silylate, Dimethicone/Vinyl Dimethicone Crosspolymer, Dimethiconevinyltrimethylsiloxysilicate Crosspolymer, Dimethiconol, Dimethiconol Arginine, Dimethiconol Beeswax, Dimethiconol Behenate, Dimethiconol Borageate, Dimethiconol Candelillate, Dimethiconol Carnaubate, Dimethiconol Cysteine, Dimethiconol Dhupa Butterate, Dimethiconol Fluoroalcohol Dilinoleic Acid, Dimethiconol Hydroxystearate, Dimethiconol Illipe Butterate, Dimethiconol/IPDI Copolymer, Dimethiconol Isostearate, Dimethiconol Kokum Butterate, Dimethiconol Lactate, Dimethiconol Meadowfoamate, Dimethiconol Methionine, Dimethiconol/Methylsilanol/Silicate Crosspolymer, Dimethiconol Mohwa Butterate, Dimethiconol Panthenol, Dimethiconol Sal Butterate, Dimethiconol/Silica Crosspolymer, Dimethiconol/Silsesquioxane Copolymer, Dimethiconol Stearate, Dimethiconol/Stearyl, Methicone/Phenyl Trimethicone Copolymer, Dimethoxysilyl Ethylenediaminopropyl Dimethicone, Dimethylamninopropylamido PCA Dimethicone, Dimethyl Oxobenzo Dioxasilane, Dimethylsilanol Hyaluronate, Dioleyl Tocopheryl Methylsilanol, Diphenyl Amodimethicone, Diphenyl Dimethicone, Diphenyl Dimethicone Crosspolymer Diphenyl Dimethicone/Vinyl Diphenyl Dimethicone/Silsesquioxane Crosspolymer, Diphenylethyl Benzyloxy Dilsiloxane, Diphenylisopropyl Dimethicone, Diphenylsiloxy Phenyl/Propyl Trimethicone, Diphenylsiloxy Phenyl Trimethicone Disiloxane, Disodium Amodimethicone Disuccinamide, Disodium PEG-12 Dimethicone Sulfosuccinate, Disodium PEG-8 Lauryl Dimethicone Sulfosuccinate, Divinyldimethicone/Dimethicone Copolymer, Divinyldimethicone/Dimethicone Crosspolymer, Drometrizole Trisiloxane, Ethylhexyl Acrylate/VP/Dimethicone Methacrylate Copolymer, Ethyl Methicone, Ethyl Trisiloxane, Fluoro )C2-8 Alkyldimethicone, Gluconamidopropyl Aminopropyl Dimethicone, 4-(2-Beta-Glucopyranosiloxy) Propoxy-2-Hydroxybenzophenone, Glyceryl Undecyl Dimethicone, Glycidoxy Dimethicone, Hexadecyl Methicone, Hexyl Dimethicone, Hexyl Methicone, Hexyltrmethoxysilane, Hydrogen Dimethicone, Hydrogen Dimethicone/Octyl Silsesquioxane Copolymer, Hydrolyzed Collagen PG-Propyl Dimethiconol, Hydrolyzed Collagen PG-Propyl Methylsilanediol, Hydrolyzed Collagen PG-Propyl Silanetriol, Hydrolyzed Keratin PG-Propyl Methylsilanediol, Hydrolyzed Sesame Protein PG-Propyl Methylsilanediol, Hydrolyzed Silk PG-Propyl Methylsilanediol, Hydrolyzed Silk PG-Propyl Methylsilanediol Crosspolymer, Hydrolyzed Soy Protein/Dimethicone PEG-7 Acetate, Hydrolyzed Soy Protein PG-Propyl Methylsilanediol, Hydrolyzed Vegetable Protein PG-Propyl Silanetriol, Hydrolyzed Wheat Protein/Cystine Bis-PG-Propyl Silanetriol Copolymer, Hydrolyzed Wheat Protein/Dimethicone PEG-7 Acetate, Hydrolyzed Wheat Protein/Dimethicone PEG-7 Phosphate Copolymer, Hydrolyzed Wheat Protein PG-Propyl Methylsilanediol, Hydrolyzed Wheat Protein PG-Propyl Silanetriol, Hydroxyethyl Acetomonium PG-Dimethicone, Hydroxypropyldimethicone, Hydroxypropyl Dimethicone Behenate, Hydroxypropyl Dimethicone Isostearate, Hydroxypropyl Dimethicone Stearate, Isobutylmethacrylate/Bis-Hydroxypropyl Dimethicone Acrylate Copolymer, Isobutylmethacrylate/Trifluoroethylmethacrylate/Bis-Hydroxypropyl Dimethicone Acrylate Copolymer, Isopentyl Trimethoxycinnamate Trisiloxane, Isopolyglyceryl-3 Dimethicone, Isopolyglyceryl-3 Dimethiconol, Isopropyl Titanium Triisostearate/Triethoxysilylethyl, Polydimethylsiloxyethyl Dimethicone Crosspolymer, Isostearyl Carboxydecyl PEG-8 Dimethicone, Lactoyl Methylsilanol Elastinate, Lauryl Dimethicone, Lauryl Dimethicone PEG-15 Crosspolymer, Lauryl Dimethicone PEG-10 Phosphate, Lauryl Dimethicone/Polyglycerin-3 Crosspolymer, Lauryl Methicone, Lauryl PEG-8 Dimethicone, Lauryl PEG-10 Methyl Ether Dimethicone, Lauryl PEG-9 Polydimethylsiloxyethyl Dimethicone, Lauryl PEG/PPG-18/18 Methicone, Lauryl Phenylisopropyl Methicone, Lauryl Phenylpropyl Methicone, Lauryl Polydimethylsiloxyethyl Dimethicone/Bis-Vinyldimethicone Crosspolymer, Lauryl Polyglyceryl-3 Polydimeethylsiloxyethyl Dimethicone, Lauryl Trimethicone, Linoleamidopropyl PG-Dimonium Chloride Phosphate Dimethicone, Methacryloyl Propyltrimethoxysilane, Methicone, Methoxy Amodimethicone/Silsesquioxane Copolymer, Methoxycinnamidopropyl Polysilsesquioxane, Methoxycinnamoylpropyl Silsesquioxane Silicate, Methoxy PEG-13 Ethyl Polysilsesquioxane, Methoxy PEG/PPG-7/3 Aminopropyl Dimethicone, Methoxy PEG/PPG-25/4 Dimethicone, Methoxy PEG-10 Propyltrimethoxysilane, Methyleugenyl PEG-8 Dimethicone, Methylpolysiloxane Emulsion, Methylsilanol Acetylmethionate, Methylsilanol Acetyltyrosine, Methylsilanol Ascorbate, Methylsilanol Carboxymethyl Theophylline, Methylsilanol Carboxymethyl Theophylline Alginate, Methylsilanol Elastinate, Methylsilanol Glycyrrhizinate, Methylsilanol Hydroxyproline, Methylsilanol Hydroxyproline Aspartate, Methylsilanol Mannuronate, Methylsilanol PCA, Methylsilanol PEG-7 Glyceryl Cocoate, Methylsilanol/Silicate Crosspolymer, Methylsilanol Spirulinate, Methylsilanol Tri-PEG-8 Glyceryl Cocoate, Methyl Trimethicone, Methyltrimethoxysilane, Myristylamidopropyl Dimethylamine Dimethicone PEG-7 Phosphate, Myristyl Methicone, Myristyl Trisiloxane, Nylon-611/Dimethicone Copolymer, PCA Dimethicone, PEG-7 Amodimethicone, PEG-8 Amodimethicone, PEG-8 Cetyl Dimethicone, PEG-3 Dimethicone, PEG-6 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG-10 Dimethicone Crosspolymer, PEG-12 Dimethicone Crosspolymer, PEG-8 Dimethicone Dimer Dilinoleate, PEG-8 Dimethicone/Dimer Dilinoleic Acid Copolymer, PEG-10 Dimethicone/Vinyl Dimethicone Crosspolymer, PEG-8 Distearmonium Chloride PG-Dimethicone, PEG-10/Lauryl to Dimethicone Crosspolymer, PEG-15/Lauryl Dimethicone Crosspolymer, PEG-15/Lauryl Polydimethylsiloxyethyl Dimethicone Crosspolymer, PEG-8 Methicone, PEG-6 Methicone Acetate, PEG-6 Methyl Ether Dimethicone, PEG-7 Methyl Ether Dimethicone, PEG-8 Methyl Ether Dimethicone, PEG-9 Methyl Ether Dimethicone, PEG-10 Methyl Ether Dimethicone, PEG-11 Methyl Ether Dimethicone, PEG-32 Methyl Ether Dimethicone, PEG-8 Methyl Ether Triethoxysilane, PEG-10 Nonafluorohexyl Dimethicone Copolymer, PEG-4 PEG-12 Dimethicone, PEG-8 PG-Coco-Glucoside Dimethicone, PEG-9 Polydimethylsiloxyethyl Dimethicone, PEG/PPG-20/22 Butyl Ether Dimethicone, PEG/PPG-22/22 Butyl Ether Dimethicone, PEG/PPG-23/23 Butyl Ether Dimethicone, PEG/PPG-24/18 Butyl Ether Dimethicone, PEG/PPG-27/9 Butyl Ether Dimethicone, PEG/PPG-3/10 Dimethicone, PEG/PPG-4/12 Dimethicone, PEG/PPG-6/4 Dimethicone, PEG/PPG-6/11 Dimethicone, PEG/PPG-8/14 Dimethicone, PEG/PPG-8/26 Dimethicone, PEG/PPG-10/2 Dimethicone, PEG/PPG-12/16 Dimethicone, PEG/PPG-:12/18 Dimethicone, PEG/PPG-14/4 Dimethicone, PEG/PPG-15/5 Dimethicone, PEG/PPG-15/15 Dimethicone, PEG/PPG-16/2 Dimethicone, PEG/PPG-16/8 Dimethicone, PEG/PPG-17/18 Dimethicone, PEG/PPG-18/6 Dimethicone, PEG/PPG-18/12 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethi-cone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, PEG/PPG-30/10 Dimethicone, PEG/PPG-25/25 Dimethicone/Acrylates Copolymer, PEG/PPG-20/22 Methyl Ether Dimethicone, PEG/PPG-24/24 Methyl Ether Glycidoxy Dimethicone, PEG/PPG-10/3 Oleyl Ether Dimethicone, PEG/PPG-5/3 Trisiloxane, PEG-4 Trifluoropropyl Dimethicone Copolymer, PEG-8 Trifluoropropyl Dimethicone Copolymer, PEG-10 Trifluoropropyl Dimethicone Copolymer, PEG-8 Trisiloxane, Perfluorocaprylyl riethoxysilylethyl Methicone, Perfluorononyl Dimethicone, Perfluorononyl Dimethicone/Methicone/Amodimethicone Crosspolymer, Perfluorononylethyl Carboxydecyl Behenyl Dimethicone, Perfluorononylethyl Carboxydecyl Hexacosyl Dimethicone, Perfluorononylethyl Carboxydecyl Lauryl/Behenyl Dimethicone, Perfluorononylethyl Carboxydecyl Lauryl Dimethicone, Perfluorononylethyl Carboxydecyl PEG-8 Dimethicone, Perfluorononylethyl Carboxydecyl PEG-10 Dimethicone, Perfluorononylethyl Dimethicone/Methicone Copolymer, Perfluorononylethyl PEG-8 Dimethicone, Perfluorononylethyl Stearyl Dimethicone, Perfluorooctylethyl/Diphenyl Dimethicone Copolymer, Perfluoroactylethyl Triethoxysilane, Perfluorooctylethyl Trimethoxysilane, Perfluorooctylethyl Trisiloxane, Perfluorooctyl Triethoxysilane, PG-Amodimethicone, Phenethyl Dimethicone, Phenethyl Disiloxane, Phenyl Dimethicone, Phenylisopropyl Dimethicone, Phenyl Methicone, Phenyl Methiconol, Phenylpropyldimethylsiloxysilicate, Phenylpropyl Ethyl Methicone, Phenyl Propyl Trimethicone, Phenyl Propyl Trimethicone/Diphenylmethicone, Phenyl Trimethicone, Platinum Divinyldisiloxane, Polyacrylate-6, Polydiethylsiloxane, Polydimethylsiloxyethyl Dimethicone/Bis-Vinyldimethicone Crosspolymer, Polydmnethylsiloxyethyl Dimethicone/Methicone Copolymer, Polydimethylsiloxy PEG/PPG-24/19 Butyl Ether Silsesquioxane, Polydimethylsiloxy PPG-13 Butyl Ether Silsesquioxane, Polyglyceryl-3 Disiloxane Dimethicone, Polyglyceryl-3/Lauryl Polydimethylsiloxyethyl Dimethicone Crosspolymer, Polyglyceryl-3 Polydimethylsiloxyethyl Dimethicone, Poly(Glycol Adipate)/Bis-Hydroxyethoxypropyl Dimethicone Copolymer, Polymethylsilsesquioxane, Polymethylsilsesquioxane/Trimethylsiloxysilicate, Polyphenylsilsesquioxane, Polypropylsilsesquioxane, Polysilicone-1, Polysilicone-2, Polysilicone-3, Polysilicone-4, Polysilicone-5, Polysilicone-6, Polysilicone-7, Polysilicone-8, Polysilicone-9, Polysilicone-10, Polysilicone-11, Polysilicone-12, Polysilicone-13, Polysilicone-14, Polysilicone-15, Polysilicone-16, Polysilicone-17, Polysilicone-18, Polysilicone-19, Polysilicone-20, Polysilicone-21, Polysilicone-18 Cetyl Phosphate, Polysilicone-1 Crosspolymer, Polysilicone-18 Stearate, Polyurethane-10, Potassium Dimethicone PEG-7 Panthenyl Phosphate, Potassium Dimethicone PEG-7 Phosphate, PPG-12 Butyl Ether Dimethicone, PPG-2 Dimethicone, PPG-12 Dimethicone, PPG-27 Dimethicone, PPG-4 Oleth-10 Dimethicone, Propoxytetramethyl Piperidinyl Dimethicone, Propyl Trimethicone, Quaternium-80, Retinoxytrimethylsilane, Silanediol Salicylate, Silanetriol, Silanetriol Arginate, Silanetriol Glutamate, Silanetriol Lysinate, Silanetriol Melaninate, Silanetriol Trehalose Ether, Silica, Silica Dimethicone Silylate, Silica Dimethyl Silylate, Silica Silylate, Silicon Carbide, Silicone Quaternium-1, Silicone Quaternium-2, Silicone Quaternium-2 Panthenol Succinate, Silicone Quaternium-3, Silicone Quatemium-4, Silicone Quaternium-5, Silicone Quaternium-6, Silicone Quaternium-7, Silicone Quaternium-8, Silicone Quaternum-9, Silicone Quaternium-10, Silicone Quaternium-11, Silicone Quaternium-12, Silicone Quaternium-15, SiliconeQuaternium-16, Silicone Quaternium-16/Glycidoxy Dimethicone Crosspolymer, Silicone Quaternium-17, Silicone Quaternium-18, Silicone Quaternium-19, Silicone Quaternium-20, Silicone Quaternium-21, Silicone Quaternium-22, Silicone Quaternium-24, Silicone Quaternium-25, Siloxanetriol Alginate, Siloxanetriol Phytate, Simethicone, Sodium Carboxydecyl PEG-8 Dimethicone, Sodium Dimethicone PEG-7 Acetyl Methyltaurate, Sodium Hyaluronate Dimethylsilanol, Sodium Lactate Methylsilanol, Sodium Mannuronate Methylsilanol, Sodium PCA Methylsilanol, Sodium PG-Propyldimethicone Thiosulfate Copolymer, Sodium PG-Propyl Thiosulfate Dimethicone, Sodium Propoxyhydroxypropyl Thiosulfate Silica, Sorbityl Silanediol, Soy Triethoxysilylpropyldimonium Chloride, Stearalkonium Dimethicone PEG-8 Phthalate, Stearamidopropyl Dimethicone, Steardimonium Hydroxypropyl Panthenyl PEG-7 Dimethicone Phosphate Chloride, Steardimonium Hydroxypropyl PEG-7 Dimethicone Phosphate Chloride, Stearoxy Dimethicone, Stearoxymethicone/Dimethicone Copolymer, Stearoxytrimethylsilane, Stearyl Aminopropyl Methicone, Stearyl Dimethicone, Stearyl/Lauryl Methacrylate Crosspolymer, Stearyl Methicone, Stearyl Triethoxysilanek, Stearyl Trimethicone, Styrene/Acrylates/Dimethicone Acrylate Crosspolymer, Styrene/Acrylates/Dimethicone Copolymer, TEA-Dimethicone PEG-7 Phosphate, Tetrabutoxypropyl Trisiloxane, Tetramethyl Hexaphenyl Tetrasiloxane, Tetramethyl Tetraphenyl Trisiloxane, Tocopheryloxypropyl Trisiloxane, Trideceth-9 PG-Amodimethicone, Triethoxycaprylylsilane, Triethoxysilylethyl Dimethicone/Methicone Copolymer, Triethoxysilylethyl Polydimethylsiloxyethyl Dimethicone, Triethoxysilylethyl Polydimethylsiloxyethyl Hexyl Dimethicone, Triethoxysilylpropylcarbamoyl Ethoxypropyl Butyl Dimethicone, Trifluoromethyl C1-4 Alkyl Dimethicone, Trifluoropropyl Cyclopetasiloxane, Trifluoropropyl Cyclotetrasiloxane, Trifluoropropyl Dimethicone, Trifluoropropyl Dimethicone/PEG-10 Crosspolymer, Trifluoropropyl Dimethicone/Trifluoropropyl Divinyldimethicone Crosspolymer, Trifluoropropyl Dimethicone/Vinyl Trifluoropropyl, Dimethicone/Silsesquioxane Crosspolymer, Trifluoropropyl Dimethiconol, Trifluoropropyldimethyl/trimethylsiloxysilicate, Trifluoropropyl Methicone, Trimethoxycaprylylsilane, Trimethoxysilyl Dimethicone, Trimethyl Pentaphenyl Trisiloxane, Trimethylsiloxyamodimethicone, Trimethylsiloxyphenyl Dimethicone, Trimethylsiloxysilicate, Trimethylsiloxysilicate/Dimethicone Crosspolymer, Trimethylsiloxysilicate/Dimethiconol Crosspolymer, Trimethylsiloxysilylcarbamoyl Pullulan, Trimethylsilyl Hydrolyzed Conchiolin Protein PG-Propyl Methylsilanediol Crosspolymer, Trimethylsilyl Hydrolyzed Silk PG-Propyl Methylsilanediol Crosspolymer, Trimethylsilyl Hydrolyzed Wheat Protein PG-Propyl Methylsilanediol Crosspolymer, Trimethylsilyl Pullulan, Trimethylsilyl Trimethylsiloxy Glycolate, Trimethylsilyl Trimethylsiloxy Lactate, Trimethylsilyl Trimethylsiloxy Salicylate, Triphenyl Trimethicone, Trisiloxane, Tris-Tributoxysiloxymethylsilane, Undecylcrylene Dimethicone, Vinyl Dimethicone, Vinyl Dimethi-cone/Lauryl Dimethicone Crosspolymer, Vinyl Dimethicone/Methicone Silsesquioxane Crosspolymer, Vinyldimethyl/Trimethylsiloxysilicate Stearyl Dimethicone Crosspolymer, VP/Dimethiconylacrylate/Polycarbamyl/Polyglycol Ester, Zinc Carboxydecyl Trisiloxane and Zinc Dimethicone PEG-8 Succinate More preferably the silicones to be contained in the mixture according to the inventions are Dimethicone, Cyclomethicone, Phenyl Trimethicone, Cyclohexasiloxane and Cyclopentasiloxane.

According to the invention it is preferred one or more terpenes (group C) are selected from the group consisting of: Acyclic terpene alcohols such as for example citronellol; geraniol; neral; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof; Acyclic terpene aldehydes and ketones such as for example geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal; Cyclic terpene alcohols such as for example menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates, 3-methyl-2-butenoates; cyclic terpene aldehydes and ketones such as for example menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4-a-methanonaphthalen-8(5-H)-one; nootkatone; dihydronootkatone; alpha-sinensal; beta-sinensal and acetylated cedarwood oil and methyl cedryl ketone.

It is more preferred that one or more terpenes (group C) are selected from the group consisting of menthol, menthone, carvone, cineol, isopulegol, alpha-terpineol and limonene.

For the musk-compounds (group D) it is preferred according to the invention that one or more compounds are selected from the group consisting of compounds as listed in the following Table A:

TABLE A

| Product name | Name/CAS name |
| --- | --- |
| EXALTENON | 4-Cyclopentadecen-1-one (4Z)-; 4-Cyclopentadecen-1-one |
| CIVETON | 9-Cycloheptadecen-1-one, (9Z)- |
| CYCLOHEXADECANOLID | Oxacycloheptadecan-2-one, |
| DIHYDROAMBRETTOLID | omega-Hexadecanolid |
| ETHYLENDODECANDIOAT | 1,4-Dioxacyclohexadecane-5,16-dione |
| GLOBALIDE ® | Oxacyclohexadecen-2-on; 15-Pentadec-(11/12)-enolid |
| ETHYLENBRASSYLAT | 1,4-Dioxacycloheptadecane-5,17-dione |
| MUSCON | 3-Methy-cyclopentadecanone |
| AMBRETTOLID | Oxacycloheptadec-10-en-2-one |
| MUSCENON | 3-Methyl-cyclopentadecenone |
| VEVIONE, AMBRETONE | 5-Cyclohexadecen-1-one |
| AURELIONE ® | 7/8-Cyclohexadecen-1-one |
| GLOBANONE ® | 8-Cyclohexadecen-1-one |
| ISOMUSCONE ® | Cyclohexadecanone |
| EXALTOLID, MACROLIDE ® | Oxacyclohexadecan-2-one |
| COSMONE ® | 3-Methyl-(5E/Z)-cyclotetradecen-1-one |
| TRASEOLIDE ® | 1-[2,3-Dihydro-1,1,2,6-tetramethyl-3-(1-methylethyl)-1H-inden-5-yl]-ethanone |
| PHANTOLIDE ® | 1-(2,3-Dihydro-1,1,2,3,3,6-hexamethyl-1H-inden-5-yl)-ethanone |
| TONALIDE ® | 1-(5,6,7,8-Tetrahydro-3,5,5,6,8,8-hexamethyl-2-naphthalenyl)-ethanone |
| CRYSOLIDE | 1-[6-(1,1-Dimethylethyl)-2,3-dihydro-1,1-dimethyl-1H-inden-4-yl]-ethanone |
| CHROMANOLIDE ® | Tridecanoic acid,1-methylethyl ester; Cyclopenta[g]-2-benzopyran, 1,3,4,6,7,8-hexahydro-4,6,6,7,8,8-hexamethyl- |

TABLE A-continued

| Product name | Name/CAS name |
| --- | --- |
| GALAXOLIDE ® | Cyclopenta[g]-2-benzopyran, 1,3,4,6,7,8-hexahydro-4,6,6,7,8,8-hexamethyl- |
| SERENILODE | 2-(1-(3,3-dimethylcyclohexyl)ethoxy)-2-methylpropyl-cyclopropanecarboxylate |
| HELVETOLIDE ® | 1-Propanol, 2-[1-(3,3-dimethylcyclohexyl)ethoxy]-2-methyl-, 1-propanoate |
| MOSKENE | 2,3-Dihydro-1,1,3,3,5-pentamethyl-4,6-dinitro-1H-Indene |
| MUSK TIBETENE | 1-(1,1-Dimethylethyl)-3,4,5-trimethyl-2,6-dinitrobenzol |
| ORINOX | 1-[4-(1,1-Dimethylethyl)-2,6-dimethylphenyl]-ethanone |
| MUSK XYLOL | 1-(1,1-Dimethylethyl)-3,5-dimethyl-2,4,6-trinitrobenzol |
| MUSK KETONE | 1-[4-(1,1-Dimethylethyl)-2,6-dimethyl-3,5-dinitrophenyl]-ethanone |
| MUSK ALPHA | 1,3-Dibromo-2-methoxy-4-methyl-5-nitrobenzol |

More preferably one or compounds of group D are selected from the group consisting of: 8-Cyclohexadecen-1-one, 1,3,4,6,7,8-hexahydro-4,6,6,7,8,8-hexamethyl-cyclopenta[g]-2-benzopyran, Cyclohexadecanone, 15-Pentadec-(11/12)-enolid and Oxacyclohexadecan-2-one.

For the mixtures of the invention (and the use of the invention) it is preferred that one or more abrasives (group E) are selected from the group consisting of: Actinidia Chinensis (Kiwi) Seed, Adansonia Digitata Seed Powder, Agave Americana Leaf Powder, Alumina, Aluminum Iron Silicates, Aluminum Silicate, Amethyst Powder, Ammonium Acryloyldimethyltaurate/Laureth-7 Methacrylate Copolymer, Amorphophallus Konjac Root Powder, Ampelopsis Japonica Root Powder, Angelica Archangelica Seed Powder, Angelica Dahurica Root Powder, Angelica Dahurica Seed Powder, Arachis Hypogaea (Peanut) Flour, Argania Spinosa Shell Powder, Artemisia Carvifolia Powder, Astragalus Membranaceus Root Powder, Astrocaryum Murumuru Seed Powder, Atractyloides Macrocephala Root/Stalk Powder, Attapulgite, Avena Sativa (Oat) Bran, Avena Sativa (Oat) Kernel Flour, Avena Sativa (Oat) Kernel Meal, Bambusa Arundinacea Juice, Bambusa Arundinacea Stem Powder, Bertholletia Exceisa Seed Powder, Bletilla Striata Root/Stalk Powder, 1,4-Butandiol/Succinic Acid/Adipic Acid/HDI Copolymer, Butyrospermum Parkii (Shea) Nut Shell Powder, Calcium Carbonate, Calcium Phosphate, Calcium Pyrophosphate, Calcium Sulfate, Calcium Sulfate Hydrate, Cannabis Sativa Seedcake, Carapa Guaianensis Seed Powder, Carya Illinoensis (Pecan) Shell Powder, Castanea Crenata (Chestnut) Shell Powder, Chalk, Charcoal Powder, Chenopodium Quinoa Seed, Chitin, Chlorophora Tinctoria Wood Extract, Chondrus Crispus Powder, Cicer Arietinum Seed Powder, Citrullus Lanatus (Watermelon) Seed Powder, Citrus Nobilis (Mandarin Orange) Peel Powder, Citrus Tangerina (Tangerine) Peel, Cnidium Monnieri Seed Powder, Cocos Nucifera (Coconut) Fruit, Cocos Nucifera (Coconut) Shell Powder, Codonopsis Pilosula Root Powder, Coffea Arabica (Coffee) Seed Powder, Coffea Robusta Seed Powder, Colloidal Oatmeal, Conchiolin Powder, Coptis Chinensis Root/Stalk Powder, Coral Powder, Corylus Avellana (Hazel) Seed Powder, Corylus Avellana (Hazel) Shell Powder, Cymbopogon Flexuosus Leaf Powder, Diamond Powder, Diatomaceous Earth, Dicalcium Phosphate, Dicalcium Phosphate Dihydrate, Dipentaerythrityl Hexaisostearate, Dolomite, Egg Shell Powder, Eijitsu, Elguea Clay, Emerald, Empetrum Nigrum Flower/Fruit/Leaf Extract, Eucalyptus Globulus Leaf Powder, Euterpe Oleracea Pulp Powder, Ficus Carica (Fig) Seed, Foeniculum Vulgare (Fennel) Seed, Fragaria Vesca (Strawberry) Seed, Fuller's Earth, Garcinia Mangostana Peel Powder, Garnet Powder, Glycine Soja (Soybean) Flour, Glycine Soja (Soybean) Seed Powder, Hakka, Helianthus Annuus (Sunflower) Seed, Helianthus Annuus (Sunflower) Seedcake, Helianthus Annuus (Sunflower) Seed Flour, Hibiscus Sabdariffa Flower Powder, Hippophae Rhamnoides Husk Powder, Hippophae Rhamnoides Seed Powder, Honey Powder, Hordeum Distichon (Barley) Seed Flour, Hordeum Vulgare Powder, Hordeum Vulgare Seed Flour, Hydrated Silica, Hydroxyapatite, Illite, Ipomoea Seed Powder, Isatis Tinctoria Root Powder, Juglans Mandshurica (Walnut) Shell Powder, Juglans Regia (Walnut) Shell Powder, Juniperus Oxycedrus Wood Powder, Kaolin, Kochia Scoparia Fruit Powder, Kurumi Kaku, Lauryl Acrylate/VA Crosspolymer, Leonurus Artemisia Powder, Linum Usitatissimum (Linseed) Seed Flour, Litchi Chinensis Seed Powder, Lithothamnium Calcarum Powder, Lithothamnium Corallioides Powder, Loess, Luffa Cylindrica Fruit, Luffa Cylindrica Fruit Powder, Lygodium japonicum Spore, Macadamia Integrifolia Shell Powder, Macadamia Ternifolia Shell Powder, Magnesium Potassium Fluorosilicate, Magnesium Sodium Fluorosilicate, Magnesium Trisilicate, Magnolia Denudata Bud Powder, Mangifera Indica (Mango) Seed, Marble Powder, Matricaria Maritima Powder, Matteuccia Struthiopteris Bud Powder, Mauritia Flexuosa Pulp Powder, Melaleuca Alternifolia (Tea Tree) Leaf, Melaleuca Alternifolia (Tea Tree) Leaf Powder, Microcrystalline Cellulose, Montmorillonite, Moring a Oleifera Fruit Powder, Moroccan Lava Clay, Mother of Pearl, Mudstone Powder, Myristyl Betaine, Nacre Powder, Nelumbo Nucifera Flower Powder, Nelumbo Nucifera Seed Powder, Nigella Damascena Seed Powder, Oenothera Biennis (Evening Primrose) Seed, Olea Europaea (Olive) Fruit, Olea Europaea (Olive) Husk Powder, Olea Europaea (Olive) Leaf Powder, Olea Europaea (Olive) Seed, Olea Europaea (Olive) Seed Powder, Oryza Sativa (Rice) Bran, Oryza Sativa (Rice) Germ Powder, Ostrea Shell Extract, Ostrea Shell Powder, Oubaku, Ovum Powder, Oyster Shell Powder, Paeonia Lactiflora Root Powder, Paeonia Officinalis Flower Powder, Papaver Soniniferum Seed, Passiflora Edulis Seed Powder, Pegmatite, Perlite, Persea Gratissima (Avocado) Fruit Powder, Persea Gratissima (Avocado) Seed, Phaseolus Angularis Seed, Phaseolus Radiatus Seed Starch, Pistacia Vera Shell Powder, Plantago Psyllium Husk, Plantago Psyllium Husk Powder, Platinum Powder, Polyethylene, Polylactic Acid, Poria Cocos Powder, Porphyra Umbilicalis Powder, Potassium Undecylenoyl Glutamate, Prunus Amygdalus Dulcis (Sweet Almond) Seedcoat Powder, Prunus Amygdalus Dulcis (Sweet Almond) Seed Meal, Prunus Amygdalus Dulcis (Sweet Almond) Shell Powder, Prunus Armeniaca (Apricot) Seed Powder, Prunus Avium (Sweet Cherry) Seed Powder, Prunus Avium (Sweet Cherry) Shell Powder, Prunus Cerasus (Bitter Cherry) Shell Powder, Prunus Mume Fruit, Prunus Persica (Peach) Flower Powder, Prunus Persica (Peach) Seed Powder, Pumice, Punica Granatum Seed, Punica Granatum Seed Powder, Quartz, Quartz Powder, Quassia Amara Wood Powder, Rosa Canina Seed, Rosa Canina Seed Powder, Rosa Centifolia Flower Powder, Rosa Rugosa Bud Powder, Rubus Idaeus (Raspberry) Seed, Rubus Idaeus (Raspberry) Seed Powder, Salt Mine Mud, Salvia Hispanica Seed, Salvia Hispanica Seed Powder, Sand, Sanguisorba Officinalis Root/Stalk Powder, Schinziophyton Rautanenii Kernel Powder, Sclerocarya Birrea Seed Powder, Scutellaria Baicalensis Root Powder, Sea Salt, Secale Cereale (Rye) Seed Flour, Silica, Sillimanite, Smilax Lanceaefolia Root/Stalk Powder, Sodium Bicarbonate, Sodium Calcium Boron Phosphate, Sodium Hydroxypropyl Starch Phosphate, Sodium Magnesium Fluorosilicate, Sodium Silicoaluminate, Solum Diatomeae, Sophora Flavescens Root Powder, Stemona Sessifolia Root Powder, Symphytum Officinale Leaf Powder, Synthetic Ruby, Synthetic Ruby Powder, Syring a Oblata Bark/Leaf Powder, Talc, Theobroma Cacao (Co-coa) Husk, Theobroma Cacao (Cocoa) Seed Powder, Theobroma Cacao (Cocoa) Shell Powder, Theobroma Grandiflorum Seed Powder, Tin Oxide, Titanium Oxynitride, Topaz, Touki, Tribulus Terrestris Fruit Powder, Tricalcium Phosphate, Trichosanthes Kirilowii Fruit Powder, Triticum Vulgare (Wheat) Bran, Triticum Vulgare (Wheat) Germ Powder, Triticum Vulgare (Wheat) Kernel Flour, Triticum Vulgare (Wheat) Starch, Vaccinium Angustifolium (Blueberry) Seed, Vaccinium Macrocarpon (Cranberry) Seed, Vaccinium Macrocarpon (Cranberry) Seed Powder, Vanilla Planifolia Seed Powder, Vanilla Tahitensis Seed, Viola Prionantha Powder, Virola Sebifera Seed Powder, Vitis Vinifera (Grape) Seed Powder, Volcanic Ash, Volcanic Rock, Wood Powder, Yokuinin, Zea Mays (Corn) Cob Meal, Zea Mays (Corn) Cob Powder, Zea Mays (Corn) Kernel Meal, Zea Mays (Corn) Seed Flour, Zea Mays (Corn) Starch and Zirconium Silicate.

For the abrasives (group E) it is more preferred that one or more abrasives are selected from the group consisting of Silica, Calcium Carbonate, Calcium Phosphate, Calcium Pyrophosphate, Dicalcium phosphate and Tin Oxide.

In the mixtures according to the invention (and in the use according to the invention) it is preferred that one or more tensides (group F) are selected from the group consisting of: Almondamidopropylamine Oxide, Almondamidopropyl Betaine, Aminopropyl Laurylglutamine, Ammonium C12-15 Alkyl Sulfate, Ammonium C:12-16 Alkyl Sulfate, Ammonium Capryleth Sulfate, Ammonium Cocomonoglyceride Sulfate, Ammonium Coco-Sulfate, Ammonium Cocoyl Isethionate, Ammonium Cocoyl Sarcosinate, Ammonium C12-15 Pareth Sulfate, Ammonium C9-10 Perfluoroalkylsulfonate, Ammonium Dinonyl Sulfosuccinate, Ammonium Dodecylbenzenesulfonate, Ammonium Isostearate, Ammonium Laureth-6 Carboxylate, Ammonium Laureth-8 Carboxylate, Ammonium Laureth Sulfate, Ammonium Laureth-5 Sulfate, Ammonium Laureth-7 Sulfate, Ammonium Laureth-9 Sulfate, Ammonium Laureth-12 Sulfate, Ammonium Lauroyl Sarcosinate, Ammonium Lauryl Sulfate, Ammonium Lauryl Sulfosuccinate, Ammonium Myreth Sulfate, Ammonium Myristyl Sulfate, Ammonium Nonoxynol-4 Sulfate, Amonium Nonoxynol-30 Sulfate, Ammonium Oleate, Ammonium Palm Kernel Sulfate, Ammonium Stearate, Ammonium Tallate, AMPD-Isostearoyl Hydrolyzed Collagen, AMPD-Rosin Hydrolyzed Collagen, AMP-Isostearoyl Hydrolyzed Collagen, AMP-Isostearoyl Hydrolyzed Keratin, AMP-Isostearoyl Hydrolyzed Soy Protein, AMP-Isostearoyl Hydrolyzed Wheat Protein, Apricotamidopropyl Betaine, Arachidic Acid, Arginine Hexyldecyl Phosphate, Avocadamidopropyl Betaine, Avocado Oil Glycereth-8 Esters, Babassu Acid, Babassuamidopropylamine Oxide, Babassuamidopropyl Betaine, Beeswax Acid, Behenamidopropyl Betaine, Behenamine Oxide, Beheneth-25, Beheneth-30, Behenic Acid, Behenyl Betaine, Bis-Butyldimethicone Polyglyceryl-3, Butoxynol-5 Carboxylic Acid, Butoxynol-19 Carboxylic Acid, Butyldimoniumhydroxypropyl Butylglucosides Chloride, Butyldimoniumhydroxypropyl Laurylglucosides Chloride, Butyl Glucoside, Butylglucoside Caprate, Butylglucosides Hydroxypropyltrmonim Chloride, Butyloctanoic Acid, C18-36 Acid, C20-40 Acid, C30-50 Acid, C16-22 Acid Amide MEA, Calcium Dodecylbenzenesulfonate, Calcium Lauroyl Taurate, C9-16 Alkane/Cycloalkane, C10-14 Alkyl Benzenesulfonic Acid, C12-14 Alkyl Diaminoethylglycine HCL, C9-15 Alkyl Phosphate, Candida Bombicola/Glucose/Methyl Rapeseedate Ferment, Canolamidopropyl Betaine, Capric Acid, Caproic Acid, Caproyl Ethyl Glucoside, Capryl/Capramidopropyl Betaine, Capryleth-4 Carboxylic Acid, Capryleth-6 Carboxylic Acid, Capryleth-9 Carboxylic Acid, Caprylic Acid, Capryloyl Collagen Amino Acids, Capryloyl Glycine, Capryloyl Hydrolyzed Collagen, Capryloyl Hydrolyzed Keratin, Capryloyl Keratin Amino Acids, Capryloyl Silk Amino Acids, Caprylyl/Capryl Glucoside, Caprylyl/Capryl Wheat Bran/Straw Glycosides, Caprylyl Glucoside, Caprylyl Glyceryl Ether, Caprylyl Pyrrolidone, Carnitine, Ceteareth-20, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Ceteareth-55, Ceteareth-60, Ceteareth-80, Ceteareth-100, Ceteareth-25 Carboxylic Acid, Ceteareth-2 Phosphate, Ceteareth-4 Phosphate, Ceteareth-5 Phosphate, Ceteareth-10 Phosphate, Ceteth-20, Ceteth-23, Ceteth-24, Ceteth-25, Ceteth-30, Ceteth-40, Ceteth-45, Ceteth-150, Ceteth-8 Phosphate, Ceteth-10 Phosphate, Ceteth-20 Phosphate, Cetoleth-22, Cetoleth-24, Cetoleth-25, Cetoleth-30, Cetyl Betaine, Chrysanthemum Sinense Flower Extract, C12-14 Hydroxyalkyl Hydroxyethyl Beta-Alanine, C12-14 Hydroxyalkyl Hydroxyethyl Sarcosine, Cocamidoethyl Betaine, Cocamidopropylamine Oxide, Cocamidopropyl Betainamide MEA Chloride, Cocamidopropyl Betaine, Cocamidopropyl Hydroxysultaine, Cocamine Oxide, Cocaminobutyric Acid, Cocaminopropionic Acid, Coceth-7 Carboxylic Acid, Coceth-4 Glucoside, Cocoamphodipropionic Acid, Cocobetainamido Amphopropionate, Coco-Betaine, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Coco-Glucoside, Cocoglucosides Hydroxypropyltrimonium Chloride, Coco-Hydroxysultaine, Coco-Morpholine Oxide, Coconut Acid, Coconut Oil Glycereth-8 Esters, Coco/Oleamidopropyl Betaine, Coco-Sultaine, Coco/Sunfloweramidopropyl Betaine, Cocoylcholine Methosulfate, Cocoyl Glutamic Acid, Cocoyl Hydrolyzed Collagen, Cocoyl Hydrolyzed Keratin, Cocoyl Hydrolyzed Oat Protein, Cocoyl Hydrolyzed Rice Protein, Cocoyl Hydrolyzed Silk, Cocoyl Hydrolyzed Soy Protein, Cocoyl Hydrolyzed Wheat Protein, Cocoyl Sarcosine, Corn Acid, Cottonseed Acid, Cottonseed Oil Glycereth-8 Esters, C10-16 Pareth-1, C10-16 Pareth-2, C11-13 Pareth-6, C11-13 Pareth-9, C11-13 Pareth-10, C11-15 Pareth-30, C11-15 Pareth-40, C12-13 Pareth-1, C12-13 Pareth-23, C12-14 Pareth-5, C12-14 Pareth-9, C13-15 Pareth-21, C14-15 Pareth-8, C20-22 Pareth-30, C20-40 Pareth-40, C20-40 Pareth-95, C22-24 Pareth-33, C30-50 Pareth-40, C9-11 Pareth-6 Carboxylic Acid, C9-11 Pareth-8 Carboxylic Acid, C11-15 Pareth-7

Carboxylic Acid, C12-13 Pareth-5 Carboxylic Acid, C12-13 Pareth-7 Carboxylic Acid, C12-13 Pareth-8 Carboxylic Acid, C12-13 Pa-reth-12 Carboxylic Acid, C12-15 Pareth-7 Carboxylic Acid, C12-15 Pareth-8 Carboxylic Acid, C12-15 Pareth-12 Carboxylic Acid, C14-15 Pareth-8 Carboxylic Acid, C6-10 Pareth-4 Phosphate, C12-13 Pareth-2 Phosphate, C12-13 Pareth-10 Phosphate, C12-15 Pareth-6 Phosphate, C12-15 Pareth-8 Phosphate, C12-15 Pareth-10 Phosphate, C12-16 Pareth-6 Phosphate, C4-18 Perfluoroalkylethyl Thiohydroxypropyltrimonium Chloride, Cupuassuamidopropyl Betaine, DEA-C12-13 Alkyl Sulfate, DEA-C12-15 Alkyl Sulfate, DEA-Ceteareth-2 Phosphate, DEA-Cetyl Sulfate, DEA-Cocoamphodipropionate, DEA-C12-13 Pareth-3 Sulfate, DEA-Cyclocarboxypropyloleate, DEA-Dodecylbenzenesulfonate, DEA-Isostearate, DEA-Laureth Sulfate, DEA-Lauryl Sulfate, DEA-Linoleate, DEA-Methyl Myristate Sulfonate, DEA-Myreth Sulfate, DEA-Myristate, DEA-Myristyl Sulfate, DEA-Oleth-5 Phosphate, DEA-Oleth-20 Phosphate, DEA PG-Oleate, Deceth-7 Carboxylic Acid, Deceth-7 Glucoside, Deceth-9 Phosphate, Decylamine Oxide, Decyl Betaine, Decyl Glucoside, Decyltetradeceth-30, Decyltetradecylamine Oxide, Diammonium Lauramido-MEA Sulfosuccinate, Diammonium Lauryl Sulfosuccinate, Diammonium Oleamido PEG-2 Sulfosuccinate, Dibutoxymethane, Di-C12-15 Pareth-2 Phosphate, Di-C12-15 Pareth-4 Phosphate, Di-C12-15 Pareth-6 Phosphate, Di-C12-15 Pareth-8 Phosphate, Di-C12-15 Pareth-10 Phosphate, Didodecyl Butanetetracarboxylate, Diethylamine Laureth Sulfate, Diethylhexyl Sodium Sulfosuccinate, Dihydroxyethyl C8-10 Alkoxypropylamine Oxide, Dihydroxyethyl C9-11 Alkoxypropylamine Oxide, Dihydroxyethyl C12-15 Alkoxypropylamine Oxide, Dihydroxyethyl Cocamine Oxide, Dihydroxyethyl Lauramine Oxide, Dihydroxyethyl Stearamine Oxide, Dihydroxyethyl Tallowamine Oxide, Dimethicone PEG-7 Phosphate, Dimethicone PEG-10 Phosphate, Dimethicone PEG/PPG-7/4 Phosphate, Dimethicone PEG/PPG-12/4 Phosphate, Dimethicone/Polyglycerin-3 Crosspolymer, Dimethicone Propyl PG-Betaine, Dimyristyl Phosphate, Dioleoylamidoethyl Hydroxyethylmonium Methosulfate, DIPA-Hydrogenated Cocoate, DTPA-Lanoate, DIPA-Myristate, Dipotassium Capryloyl Glutamate, Dipotassium Lauryl Sulfosuccinate, Dipotassium Undecylenoyl Glutamate, Disodium Babassuamido MEA-Sulfosuccinate, Disodium Caproamphodiacetate, Disodium Capraamphodipropionate, Disodium Capryloamphodiacetate, Disodium Capryloamphodipropionate, Disodium Capryloyl Glutamate, Disodium Cetearyl Sulfosuccinate, Disodium Cetyl Phenyl Ether Disulfonate, Disodium Cetyl Sulfosuccinate, Disodium Cocamido MEA-Sulfosuccinate, Disodium Cocamido MIPA PEG-4 Sulfosuccinate, Disodium Cocamido MIPA-Sulfosuccinate, Disodium Cocamido PEG-3 Sulfosuccinate, Disodium Coceth-3 Sulfosuccinate, Disodium Cocoamphocarboxyethylhydroxypropylsulfonate, Disodium Cocoamphodiacetate, Disodium Cocoamphodipropionate, Disodium Coco-Glucoside Sulfosuccinate, Disodium Coco-Sulfosuccinate, Disodium Cocoyl Butyl Gluceth-10 Sulfosuccinate, Disodium Cocoyl Glutamate, Disodium C12-14 Pareth-1 Sulfosuccinate, Disodium C12-14 Pareth-2 Sulfosuccinate, Disodium C12-15 Pareth Sulfosuccinate, Disodium C12-14 Sec-Pareth-3 Sulfosuccinate, Disodium C12-14 Sec-Pareth-5 Sulfosuccinate, Disodium C12-14 Sec-Pareth-7 Sulfosuccinate, Disodium C12-14 Sec-Pareth-9 Sulfosuccinate, Disodium C12-14 Sec-Pareth-12 Sulfosuccinate, Disodium Deceth-5 Sulfosuccinate, Disodium Deceth-6 Sulfosuccinate, Disodium Decyl Phenyl Ether Disulfonate, Disodium Dihydroxyethyl Sulfosuccinylundecylenate, Disodium Ethylene Dicocamide PEG-15 Disulfate, Disodium Hydrogenated Cottonseed Glyceride Sulfosuccinate, Disodium Hydrogenated Tallow Glutamate, Disodium Hydroxydecyl Sorbitol Citrate, Disodium Isodecyl Sulfosuccinate, Disodium Isostearamido MEA-Sulfosuccinate, Disodium Isostearamido MIPA-Sulfosuccinate, Disodium Isostearoamphodiacetate, Disodium Isostearoamphodipropionate, Disodium Isostearyl Sulfosuccinate, Disodium Laneth-5 Sulfosuccinate, Disodium Lauramido MEA-Sulfosuccinate, Disodium Lauramido MIPA Glycol Sulfosuccinate, Disodium Lauramido PEG-2 Sulfosuccinate, Disodium Lauramido PEG-5 Sulfosuccinate, Disodium Laureth-5 Carboxyamphodiacetate, Disodium Laureth-7 Citrate, Disodium Laureth Sulfosuccinate, Disodium Laureth-6 Sulfosuccinate, Disodium Laureth-9 Sulfosuccinate, Disodium Laureth-12 Sulfosuccinate, Disodium Lauriminobishydroxypropylsulfonate, Disodium Lauriminodiacetate, Disodium Lauriminodipropionate, Disodium Lauriminodipropionate Tocopheryl Phosphates, Disodium Lauroamphodiacetate, Disodium Lauroamphodipropionate, Disodium N-Lauroyl Aspartate, Disodium Lauroyl Glutamate, Disodium Lauryl Phenyl Ether Disulfonate, Disodium Lauryl Sulfosuccinate, Disodium Nlyristamido MEA-Sulfosuccinate, Disodium Nonoxynol-10 Sulfosuccinate, Disodium Oleamido MEA-Sulfosuccinate, Disodium Oleamido MIPA-Sulfosuccinate, Disodium Oleamido PEG-2 Sulfosuccinate, Disodium Oleoamphodipropionate, Disodium Oleth-3 Sulfosuccinate, Disodium Oleyl Phosphate, Disodium Oleyl Sulfosuccinate, Disodium Palmitamido PEG-2 Sulfosuccinate, Disodium Palmitoleamido PEG-2 Sulfosuccinate, Disodium PEG-4 Cocamido MIPA-Sulfosuccinate, Disodium PEG-12 Dimethicone Sulfosuccinate, Disodium PEG-8 Palm Glycerides Sulfosuccinate, Disodium PPG-2-Isodeceth-7 Carboxymnphodiacetate, Disodium Ricinoleamido MEA-Sulfosuccinate, Disodium Sitostereth-14 Sulfosuccinate, Disodium Soyamphodiacetate, Disodium Stearamido MEA-Sulfosuccinate, Disodium Steariminodipropionate, Disodium Stearoamphodiacetate, Disodium Stearoyl Glutamate, Disodium Stearyl Sulfosuccinamate, Disodium Stearyl Sulfosuccinate, Disodium 2-Sulfolaurate, Disodium 2-Sulfopalmitate, Disodium Tallamido MEA-Sulfosuccinate, Disodium Tallowamido MEA-Sulfosuccinate, Disodium Tallowamhodiacetate, Disodium Tallowiminodipropionate, Disodium Tallow Sulfosuccinamate, Disodium Tridecylsulfosuccinate, Disodium Undecylenamido MEA-Sulfosuccinate, Disodium Undecylenamido PEG-2 Sulfosuccinate, Disodium Undecylenoyl Glutamate, Disodium Wheat Germamido MEA-Sulfosuccinate, Disodium Wheat Germamido PEG-2 Sulfosuccinate, Disodium Wheatgermamphodiacetate, Di-TEA-Cocamide Diacetate, Di-TEA-Oleamido PEG-2 Sulfosuccinate, Di-TEA-Palmitoyl Aspartate, Ditridecyl Sodium Sulfosuccinate, Dodecylbenzene Sulfonic Acid, Erucamidopropyl Hydroxysultaine, Ethylhexeth-3 Carboxylic Acid, Ethyl PEG-15 Cocamine Sulfate, Glyceryl Capryl Ether, Hexyldecanoic Acid, Hydrogenated Coconut Acid, Hydrogenated Laneth-25, Hydrogenated Menhaden Acid, Hydrogenated Palm Acid, Hydrogenated Palm Kernel Amine Oxide, Hydrogenated Tallow Acid, Hydrogenated Tallowamine Oxide, Hydrogenated Tallow Betaine, Hydrogenated Talloweth-25, Hydrogenated Tallowoyl Glutamic Acid, Hydrolyzed Candida Bombicola Extract, Hydroxyceteth-60, Hydroxyethyl Acetamonium PG-Dimethicone, Hydroxyethylbutylamine Laureth Sulfate, Hydroxyethyl Carboxymethyl Cocamidopropylamine, Hydroxyethyl Hydroxypropyl C12-15 Alkoxypropylamine Oxide, Hydroxylauryl/Hydroxymyristyl Betaine, Hydroxystearic Acid, Hydroxysuccinimidyl C10-40 Isoalkyl Acidate, Hydroxysuccinimidyl C21-22 Isoalkyl Acidate, Hydroxysultaines, IPDI/PEG-15 Soyamine Oxide Copolymer, IPDI/PEG-15 Soyethonium Ethosulfate Copolymer, IPDI/PEG-15 Soy Glycinate Copolymer, Isoceteth-30, Isolaureth-4 Phosphate, Isopolyglyceryl-3 Dimethicone, Isopolyglyceryl-3 Dimethiconol, Isopropanolamine Lanolate, Isopropylamine Dodecylbenzenesulfonate, Isostearamidopropylamine Oxide, Isostearamidopropyl Betaine, Isostearamidopropyl Morpholine Oxide, Isosteareth-8, Isosteareth-16, Isosteareth-22, Isosteareth-25, lsosteareth-50, Isostearic Acid, Isostearoyl Hydrolyzed Collagen, Jojoba Oil PEG-150 Esters, Jojoba Wax PEG-80 Esters, Jojoba Wax PEG-120 Esters, Laneth-20, Laneth-25, Laneth-40, Laneth-50, Laneth-60, Laneth-75, Lanolin Acid, Lauramidopropylamine Oxide, Lauramidopropyl Betaine, Lauramidopropyl Hydroxysultaine, Lauramine Oxide, Lauraminopropionic Acid, Laurdimoniumhydroxypropyl Decylglucosides Chloride, Laurdimoniumhydroxypropyl Laurylgiucosides Chloride, Laureth-16, Laureth-20, Laureth-21, Laureth-23, Laureth-25, Laureth-30, Laureth-38, Laureth-40, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, Laureth-6 Citrate, Laureth-7 Citrate, Laureth-1 Phosphate, Laureth-2 Phosphate, Laureth-3 Phosphate, Laureth-4 Phosphate, Laureth-7 Phosphate, Laureth-8 Phosphate, Laureth-7 Tartrate, Lauric Acid, Laurimino Bispropanediol, Lauriminodipropionic Acid, Lauroamphodipropionic Acid, Lauroyl Beta-Alanine, Lauroyl Collagen Amino Acids, Lauroyl Ethyltrimonium Methosulfate, Lauroyl Hydrolyzed Collagen, Lauroyl Hydrolyzed Elastin, Lauroyl Methyl Glucamide, Lauroyl Sarcosine, Lauroyl Silk Amino Acids, Lauryl Betaine, Lauryl Dimethicone/Polyglycerin-3 Crosspoymer, Lauryldimoniumhydroxypropyl Cocoglucosides Chloride, Lauryl Glucoside, Laurylgiucosides Hydroxypropyltrimonium Chloride, Lauryl Glycol Hydroxypropyl Ether, Lauryl Hydroxysultaine, Lauryl Malamide, Lauryl Methylgiucamide, Lauryl/Myristyl Glycol Hydroxypropyl Ether, Lauryl/Myristyl Wheat Bran/Straw Glycosides, Lauryl Polyglyceryl-3 Polydimethylsiloxyethyl Dimethicone, Lauryl Pyrrolidone, Lauryl Sultaine, Linoleic Acid, Linolenic Acid, Linseed Acid, Lysine Cocoate, Macadamia Seed Oil Glycereth-8 Esters, Magnesium Coceth Sulfate, Magnesium Coco-Sulfate, Magnesium lsododecylbenzenesulfonate, Magnesium Laureth-11 Carboxylate, Magnesium Laureth Sulfate, Magnesium Laureth-5 Sulfate, Magnesium Laureth-8 Sulfate, Magnesium Laureth-:16 Sulfate, Magnesium Laureth-3 Sulfosuccinate, Magnesium Lauryl Hydroxypropyl Sulfonate, Magnesium Lauryl Sulfate, Magnesium Methyl Cocoyl Taurate, Magnesium Myreth Sulfate, Magnesium Oleth Sulfate, Magnesium/TEA-Coco-Sulfate, Manicouagan Clay, MEA-Cocoate, MEA-Laureth-6 Carboxylate, MEA-Laureth Sulfate, MEA-Lauryl Sulfate, MEA PPG-6 Laureth-7 Carboxylate, MEA-PPG-8-Stearth-7 Carboxylate, MEA-Undecylenate, Meroxapol 108, Meroxapol 174, Meroxapol 178, Meroxapol 254, Meroxapol 255, Meroxapol 258, Meroxapol 314, Methoxy PEG-450 Amidoglutaroyl Succinimide, Methoxy PEG-450 Amide Hydroxysuccinimidyl Succinamate, Methoxy PEG-450 Maleimide, Methyl Morpholine Oxide, Milkamidopropyl Amine Oxide, Milkamidopropyl Betaine, Minkamidopropylamine Oxide, Minkamidopropyl Betaine, MIPA C12-15 Pareth Sulfate, MIPA-Dodecylbenzenesulfonate, MIPA-Laureth Sulfate, MIPA-Lauryl Sulfate, Mixed Isopropanolamines Lanolate, Mixed Isopropanolamines Lauryl Sulfate, Mixed Isopropanolamines Myristate, Morpholine Oleate, Morpholine Stearate, Myreth-3 Carboxylic Acid, Myreth-5 Carboxylic Acid, Myristalkoniun Chloride, Myristamidopropylamine Oxide, Myristamidopropyl Betaine, Myristamidopropyl Dimethylamine Phosphate, Myristamidopropyl Hydroxysultaine, Myristamidopropyl PG-Dimonium Chloride Phosphate, Myristamine Oxide, Myrstaminopropionic Acid, Myristic Acid, Myristoyl Ethyltrimonium Methosulfate, Myristoyl Glutamic Acid, Myristoyl Hydrolyzed Collagen, Myristoyl Sarcosine, Myristyl Betaine, Myristyl/Cetyl Amine Oxide, Myristyldimoniumhydroxypropyl Cocoglucosides Chloride, Myristyl Glucoside, Myristyl Phosphate, Nonoxynol-20, Nonoxynol-23, Nonoxynol-25, Nonoxynol-30, Nonoxynol-35, Nonoxynol-40, Nonoxynol-44, Nonoxynol-50, Nonoxynol-100, Nonoxynol-120, Nonoxynol-5 Carboxylic Acid, Nonoxynol-8 Carboxylic Acid, Nonoxynol-10 Carboxylic Acid, Nonoxynol-3 Phosphate, Nonoxynol-4 Phosphate, Nonoxynol-6 Phosphate, Nonoxynol-9 Phosphate, Nonoxynol-10 Phosphate, Nonyl Nonoxynol-30, Nonyl Nonoxynol-49, Nonyl Nonoxynol-100, Nonyl Nonoxynol-150, Nonyl Nonoxynol-7 Phosphate, Nonyl Nonoxynol-8 Phosphate, Nonyl Nonoxynol-9 Phosphate, Nonyl Nonoxynol-10 Phosphate, Nonyl Nonoxynol-11 Phosphate, Nonyl Nonoxynol-15 Phosphate, Nonyl Nonoxynol-24 Phosphate, Oatamidopropyl Betaine, Octoxynol-16, Octoxynol-25, Octoxynol-30, Octoxynol-33, Octoxynol-40, Octoxynol-70, Octoxynol-20 Carboxylic Acid, Octyldodeceth-20, Octyldodeceth-25, Octyldodeceth-30, Oleamidopropylamine Oxide, Oleamidopropyl Betaine, Oleamidopropyl Hydroxysultaine, Oleamine Oxide, Oleic Acid, Oleoyl Hydrolyzed Collagen, Oleoyl Sarcosine, Oleth-20, Oleth-23, Oleth-24, Oleth-25, Oleth-30, Oleth-35, Oleth-40, Oleth-44, Oleth-50, Oleth-3 Carboxylic Acid, Oleth-6 Carboxylic Acid, Oleth-10 Carboxylic Acid, Oleyl Betaine, Olivamidopropylamine Oxide, Olivamidopropyl Betaine, Olive Acid, Olivoyl Hydrolyzed Wheat Protein, Ophiopogon Extract Stearate, Ozonized Oleth-10, Ozonized PEG-10 Oleate, Ozonized PEG-14 Oleate, Ozonized Polysorbate 80, Palm Acid, Paimamidopropyl Betaine, Palmeth-2 Phosphate, Palmitamidopropylamine Oxide, Palmitamidopropyl Betaine, Palmitamine Oxide, Paimitic Acid, Palmitoyl Collagen Amino Acids, Palmitoyl Glycine, Palmitoyl Hydrolyzed Collagen, Palmitoyl Hydrolyzed Milk Protein, Palmitoyl Hydrolyzed Wheat Protein, Palmitoyl. Keratin Amino Acids, Palmitoyl Oligopeptide, Palmitoyl Silk Amino Acids, Palm Kernel Acid, Palm Kernelamidopropyl Betaine, Peach Kernel Oil Glycereth-8 Esters, Peanut Acid, PEG-10 Castor Oil, PEG-40 Castor Oil, PEG-44 Castor Oil, PEG-50 Castor Oil, PEG-54 Castor Oil, PEG-55 Castor Oil, PEG-60 Castor Oil, PEG-80 Castor Oil, PEG-100 Castor Oil, PEG-200 Castor Oil, PEG-11 Cocamide, PEG-6 Cocamide Phosphate, PEG-4 Cocamine, PEG-8 Cocamine, PEG-12 Cocamine, PEG-150 Dibehenate, PEG-90 Diisostearate, PEG-75 Dilaurate, PEG-150 Dilaurate, PEG-75 Dioleate, PEG-150 Dioleate, PEG-75 Distearate, PEG-120 Distearate, PEG-150 Distearate, PEG-175 Distearate, PEG-190 Distearate, PEG-250 Distearate, PEG-30 Glyceryl Cocoate, PEG-40 Glyceryl Cocoate, PEG-78 Glyceryl Cocoate, PEG-80 Glyceryl Cocoate, PEG-30 Glyceryl Isostearate, PEG-40 Glyceryl Isostearate, PEG-50 Glyceryl Isostearate, PEG-60 Glyceryl Isostearate, PEG-90 Glyceryl Isostearate, PEG-23 Glyceryl Laurate, PEG-30 Glyceryl Laurate, PEG-25 Glyceryl Oleate, PEG-30 Glyceryl Oleate, PEG-30 Glyceryl Soyate, PEG-25 Glyceryl Stearate, PEG-30 Glyceryl Stearate, PEG-40 Glyceryl Stearate, PEG-120

Glyceryl Stearate, PEG-200 Glyceryl Stearate, PEG-28 Glyceryl Tallowate, PEG-80 Glyceryl Tallowate, PEG-82 Glyceryl Tallowate, PEG-130 Glyceryl Tallowate, PEG-200 Glyceryl Tallowate, PEG-45 Hydrogenated Castor Oil, PEG-50 Hydrogenated Castor Oil, PEG-54 Hydrogenated Castor Oil, PEG-55 Hydrogenated Castor Oil, PEG-60 Hydrogenated Castor Oil, PEG-80 Hydrogenated Castor Oil, PEG-100 Hydrogenated Castor Oil, PEG-200 Hydrogenated Castor Oil, PEG-30 Hydrogenated Lanolin, PEG-70 Hydrogenated Lanolin, PEG-50 Hydrogenated Palmamide, PEG-2 Isostearate, PEG-3 Isostearate, PEG-4 Isostearate, PEG-6 Isostearate, PEG-8 Isostearate, PEG-10 Isostearate, PEG-12 Isostearate, PEG-20 Isostearate, PEG-30 Isostearate, PEG-40 Isostearate, PEG-26 Jojoba Acid, PEG-40 Jojoba Acid, PEG-15 Jojoba Alcohol, PEG-26 Jojoba Alcohol, PEG-40 Jojoba Alcohol, PEG-35 Lanolin, PEG-40 Lanolin, PEG-50 Lanolin, PEG-55 Lanolin, PEG-60 Lanolin, PEG-70 Lanolin, PEG-75 Lanolin, PEG-85 Lanolin, PEG-100 Lanolin, PEG-150 Lanolin, PEG-75 Lanolin Oil, PEG-2 Lauramide, PEG-3 Lauramine Oxide, PEG-20 Laurate, PEG-32 Laurate, PEG-75 Laurate, PEG-150 Laurate, PEG-70 Mango Glycerides, PEG-20 Mannitan Laurate, PEG-8 Methyl Ether Dimethicone, PEG-120 Methyl Glucose Dioleate, PEG-80 Methyl Glucose Laurate, PEG-120 Methyl Glucose Trioleate, PEG-4 Montanate, PEG-30 Oleamine, PEG-20 Oleate, PEG-23 Oleate, PEG-32 Oleate, PEG-36 Oleate, PEG-75 Oleate, PEG-150 Oleate, PEG-20 Palmitate, PEG-150 Polyglyceryl-2 Tristearate, PEG/PPG-28/21 Acetate Dimethicone, PEG/PPG-24/18 Butyl Ether Dimethicone, PEG/PPG-3/17 Copolymer, PEG/PPG-5/35 Copolymer, PEG/PPG-8/55 Copolymer, PEG/PPG-10/30 Copolymer, PEG/PPG-10/65 Copolymer, PEG/PPG-12/35 Copolymer, PEG/PPG-16/17 Copolymer, PEG/PPG-20/9 Copolymer, PEG/PPG-20/20 Copolymer, PEG/PPG-20/60 Copolymer, PEG/PPG-20/65 Copolymer, PEG/PPG-22/25 Copolymer, PEG/PPG-28/30 Copolymer, PEG/PPG-30-35 Copolymer, PEG/PPG-30/55 Copolymer, PEG/PPG-35/40 Copolymer, PEG/PPG-50/40 Copolymer, PEG/PPG-150/35 Copolymer, PEG/PPG-160/30 Copolymer, PEG/PPG-190/60 Copolymer, PEG/PPG-200/40 Copolymer, PEG/PPG-300/55 Copolymer, PEG/PPG-20/22 Methyl Ether Dimethicone, PEG-26-PPG-30 Phosphate, PEG/PPG-4/2 Propylheptyl Ether, PEG/PPG-6/2 Propylheptyl Ether, PEG-7/PPG-2 Propylheptyl Ether, PEG/PPG-8/2 Propylheptyl Ether, PEG/PPG-10/2 Propylheptyl Ether, PEG/PPG-14/2 Propylheptyl Ether, PEG/PPG-40/2 Propylheptyl Ether, PEG/PPG-10/2 Ricinoleate, PEG/PPG-32/3 Ricinoleate, PEG-55 Propylene Glycol Oleate, PEG-25 Propylene Glycol Stearate, PEG-75 Propylene Glycol Stearate, PEG-120 Propylene Glycol Stearate, PEG-5 Rapeseed Sterol, PEG-10 Rapeseed Sterol, PEG-40 Ricinoleamide, PEG-75 Shea Butter Glycerides, PEG-75 Shorea Butter Glycerides, PEG-20 Sorbitan Cocoate, PEG-20 Sorbitan Isostearate, PEG-40 Sorbitan Lanolate, PEG-75 Sorbitan Lanolate, PEG-10 Sorbitan Laurate, PEG-40 Sorbitan Laurate, PEG-44 Sorbitan Laurate, PEG-75 Sorbitan Laurate, PEG-80 Sorbitan Laurate, PEG-20 Sorbitan Oleate, PEG-80 Sorbitan Palmitate, PEG-40 Sorbitan Stearate, PEG-60 Sorbitan Stearate, PEG-: 160 Sorbitan Triisostearate, PEG-40 Soy Sterol, PEG-2 Stearamide Carboxylic Acid, PEG-9 Stearamide Carboxylic Acid, PEG-20 Stearate, PEG-23 Stearate, PEG-25 Stearate, PEG-30 Stearate, PEG-32 Stearate, PEG-35 Stearate, PEG-36 Stearate, PEG-40 Stearate, PEG-45 Stearate, PEG-50 Stearate, PEG-55 Stearate, PEG-75 Stearate, PEG-90 Stearate, PEG-100 Stearate, PEG-120 Stearate, PEG-150 Stearate, PEG-45 Stearate Phosphate, PEG-20 Tallate, PEG-50 Tallow Amide, PEG-2 Tallowamide DEA, PEG-20 Tallowate, PEG-66 Trihydroxystearin, PEG-200 Trihydroxystearin, PEG-60 Tsubakiate Glycerides, Pelargonic Acid, Pentadoxynol-200, Pheneth-6 Phosphate, Poloxamer 105, Poloxamer 108, Poloxamer 182, Poloxamer 183, Poloxam 184, Poloxamer 188, Poloxamer 217, Poloxamer 234, Poloxamer 235, Poloxamer 237, Poloxamer 238, Poloxamer 288, Poloxamer 334, Poloxamer 335, Poloxamer 338, Poloxamine 908, Poloxamine 1508, Polydimethylsiloxy PEG/PPG-24/19 Butyl Ether Silsesquioxane, Polydimethylsiloxy PPG-13 Butyl Ether Silsesquioxane, Polyglyceryl-6 Caprate, Polyglyceryl-10 Dilaurate, Polyglyceryl-20 Heptacaprylate, Polyglyceryl-20 Hexacaprylate, Polyglyceryl-2 Lauryl Ether, Polyglyceryl-10 Lauryl Ether, Polyglyceryl-20 Octaisononanoate, Polyglyceryl-6 Pentacaprylate, Polyglyceryl-10 Pentacaprylate, Polyglyceryl-3 Polydimethylsiloxyethyl Dimethicone, Polyglyceryl-6 Tetracaprylate, Polyglyceryl-10 Tetralaurate, Polyglyceryl-6 Tricaprylate, Polyglyceryl-10 Trilaurate, Polyquaternium-77, Polyquaternium-78, Polyquaternium-79, Polyquaternium-80, Polyquaternium-81, Polyquaternium-82, Pomaderris Kumerahou Flower/Leaf Extract, Poria Cocos Extract, Potassium Abietoyl Hydrolyzed Collagen, Potassium Babassuate, Potassium Behenate, Potassium C9-15 Alkyl Phosphate, Potassium C11-15 Alkyl Phosphate, Potassium C12-13 Alkyl Phosphate, Potassium C12-14 Alkyl Phosphate, Potassium Caprate, Potassium Capryloyl Glutamate, Potassium Capryloyl Hydrolyzed Rice Protein, Potassium Castorate, Potassium Cocoate, Potassium Cocoyl Glutamate, Potassium Cocoyl Glycinate, Potassium Cocoyl Hydrolyzed Casein, Potassium Cocoyl Hydrolyzed Collagen, Potassium Cocoyl Hydrolyzed Corn Protein, Potassium Cocoyl Hydrolyzed Keratin, Potassium Cocoyl Hydrolyzed Oat Protein, Potassium Cocoyl Hydrolyzed Potato Protein, Potassium Cocoyl Hydrolyzed Rice Bran Protein, Potassium Cocoyl Hydrolyzed Rice Protein, Potassium Cocoyl Hydrolyzed Silk, Potassium Cocoyl Hydrolyzed Soy Protein, Potassium Cocoyl Hydrolyzed Wheat Protein, Potassium Cocoyl Hydrolyzed Yeast Protein, Potassium Cocoyl PCA, Potassium Cocoyl Sarcosinate, Potassium Cocoyl Taurate, Potassium Cornate, Potassium Cyclocarboxypropyloleate, Potassium Dihydroxyethyl Cocamine Oxide Phosphate, Potassium Dimethicone PEG-7 Phosphate, Potassium Dodecylbenzenesulfonate, Potassium Hempseedate, Potassium Hydrogenated Cocoate, Potassium Hydrogenated Palmate, Potassium Hydrogenated Tallowate, Potassium Hydroxystearate, Potassium isostearate, Potassium Lanolate, Potassium Laurate, Potassium Laureth-3 Carboxylate, Potassium Laureth-4 Carboxylate, Potassium Laureth-5 Carboxylate, Potassium Laureth-6 Carboxylate, Potassium Laureth-10 Carboxylate, Potassium Laureth Phosphate, Potassium Lauroyl Collagen Amino Acids, Potassium Lauroyl Glutamate, Potassium Lauroyl Hydrolyzed Collagen, Potassium Lauroyl Hydrolyzed Pea Protein, Potassium Lauroyl Hydrolyzed Soy Protein, Potassium Lauroyl PCA, Potassium Lauroyl Pea Amino Acids, Potassium Lauroyl Sarcosinate, Potassium Lauroyl Silk Amino Acids, Potassium Lauroyl Wheat Amino Acids, Potassium Lauryl Phosphate, Potassium Lauryl Sulfate, Potassium Linoleate, Potassium Metaphosphate, Potassium Methyl Cocoyl Taurate, Potassium Myristate, Potassium Myristoyl Glutamate, Potassium Myristoyl Hydrolyzed Collagen, Potassium Octoxynol-12 Phosphate, Potassium Oleate, Potassium Oleoyl Hydrolyzed Collagen, Potassium Olivate, Potassium Olivoyl Hydrolyzed Oat Protein, Potassium Oliyoyl Hydrolyzed Wheat Protein, Potassium Olivoyl/Lauroyl Wheat Amino Acids, Potassium Olivoyl PCA, Potassium Palmate, Potassium Palmitate, Potassium Palmitoyl Hydrolyzed Corn Protein, Potassium Palmitoyl Hydrolyzed Oat Protein, Potassium Palmitoyl Hydrolyzed Rice Protein, Potassium Palmitoyl Hydrolyzed Sweet Almond Protein, Potassium Palmitoyl Hydrolyzed Wheat Protein, Potassium Palm Kernelate, Potassium Peanutate, Potassium Rapeseedate, Potassium Ricinoleate, Potassium Safflowerate, Potassium Soyate, Potassium Stearate, Potassium Stearoyl Hydrolyzed Collagen, Potassium Tallate, Potassium Tallowate, Potassium Taurate, Potassium Taurine Laurate, Potassium Trideceth-3 Carboxylate, Potassium Trideceth-4 Carboxylate, Potassium Trideceth-7 Carboxylate, Potassium Trideceth-15 Carboxylate, Potassium Trideceth-19 Carboxylate, Potassium Trideceth-6 Phosphate, Potassium Trideceth-7 Phosphate, Potassium Tsubakiate, Potassium Undecylenate, Potassium Undecylenoyl Hydrolyzed Collagen, Potassium Undecylenoyl Hydrolyzed Rice Protein, PPG-30-Buteth-30, PPG-36-Buteth-36, PPG-38-Buteth-37, PPG-30-Capryleth-4 Phosphate, PPG-10 Cetyl Ether Phosphate, PPG-2 C9-11 Pareth-8, PPG-1-Deceth-5, PPG-3-Deceth-2 Carboxylic Acid, PPG-30 Ethylhexeth-4 Phosphate, PPG-20-Glycereth-30, PPG-2 Hydroxyethyl Cocoilsostearamide, PPG-2-Isodeceth-8, PPG-2-Isodeceth-10, PPG-2-Isodeceth-18, PPG-2-lsodeceth-25, PPG-4-lsodeceth-10, Propyltrimonium Hydrolyzed Collagen, Quaternium-24, Quaternium-52, Quaternium-87, Rapeseed Acid. Rice Bran Acid, Rice Oil Glycereth-8 Esters, Ricinoleamidopropyl Betaine, Ricinoleic Acid, Ricinoleth-40, Safflower Acid, Sapindus Oahuensis Fruit Extract, Saponaria Officinalis Root Powder, Saponins, Sekken-K, Sekken-Na/K, Sekken Soji, Sekken Soji-K, Sesame Oil Glycereth-8 Esters, Sesamidopropylamine Oxide, Sesamidopropyl Betaine, Shea Butteramidopropyl Betaine, Shea Butter Glycereth-8 Esters, Sodium Arachidate, Sodium Arganampohoacetate, Sodium Astrocaryum Murumuruate, Sodium Avocadoate, Sodium Babassuamphoacetate, Sodium Babassuate, Sodium Babassu Sulfate, Sodium Behenate, Sodium Bisglycol Ricinosulfosuccinate, Sodium Bis-Hydroxyethylglycinate Coco-Glucosides Crosspolymer, Sodium Bis-Hydroxyethylglycinate Lauryl-Glucosides Crosspolymer, Sodium Borageamidopropyl PG-Dimonium Chloride Phosphate, Sodium Butoxynol-12 Sulfate, Sodium Butylglucosides Hydroxypropyl Phosphate, Sodium C13-17 Alkane Sulfonate, Sodium C14-18 Alkane Sulfonate, Sodium C12-15 Alkoxypropyl Iminodipropionate, Sodium C10-16 Alkyl Sulfate, Sodium C11-15 Alkyl Sulfate, Sodium C12-13 Alkyl Sulfate, Sodium C12-15 Alkyl Sulfate, Sodium C12-18 Alkyl Sulfate, Sodium C16-20 Alkyl Sulfate, Sodium C9-22 Alkyl Sec Sulfonate, Sodium C14-17 Alkyl Sec Sulfonate, Sodium Caprate, Sodium Capromnphoacetate, Sodium Caproamphohydroxypropylsulfonate, Sodium Caproamphopropionate, Sodium Caproyl Methyltaurate, Sodium Caprylate, Sodium Capryleth-2 Carboxylate, Sodium Capryleth-9 Carboxylate, Sodium Capryloamphoacetate, Sodium Capryloamphohydroxypropylsulfonate, Sodium Capryloamphopropionate, Sodium Capryloyl Glutamate, Sodium Capryloyl Hydrolyzed Wheat Protein, Sodium Caprylyl PG-Sulfonate, Sodium Caprylyl Sulfonate, Sodium Castorate, Sodium Ceteareth-13 Carboxylate, Sodium Cetearyl Sulfate, Sodium Ceteth-13 Carboxylate, Sodium Cetyl Sulfate, Sodium Cocamidopropyl PG-Dimonium Chloride Phosphate, Sodium Cocaminopropionate, Sodium Coceth Sulfate, Sodium Coceth-30 Sulfate, Sodium Cocoabutteramphoacetate, Sodium Cocoa Butterate, Sodium Cocoamphoacetate, Sodium Cocoamphohydroxypropylsulfonate, Sodium Cocoamphopropionate, Sodium Cocoate, Sodium Coco/Babassu/ Andiroba Sulfate, Sodium Coco/Babassu Sulfate, Sodium Cocoglucosides Hydroxypropyl Phosphate, Sodium Coco-glucosides Hydroxypropylsulfonate, Sodium Coco-Glucoside Tartrate, Sodium Cocoglyceryl Ether Sulfonate, Sodium Coco/Hydrogenated Tallow Sulfate, Sodium Cocoiminodiacetate, Sodium Cocomonoglyceride Sulfate, Sodium Cocomonoglyceride Sulfonate, Sodium Coco PG-Dimonium Chloride Phosphate, Sodium Coco-Sulfate, Sodium Coco Sulfoacetate, Sodium Cocoyl Alaninate, Sodium Cocoyl Amino Acids, Sodium Cocoyl Collagen Amino Acids, Sodium Cocoyl Glutamate, Sodium Cocoyl Glutaminate, Sodium Cocoyl Glycinate, Sodium Cocoyl/Hydrogenated Tallow Glutamate, Sodium Cocoyl Hydrolyzed Collagen, Sodium Cocoyl Hydrolyzed Keratin, Sodium Cocoyl Hydrolyzed Rice Protein, Sodium Cocoyl Hydrolyzed Silk, Sodium Cocoyl Hydrolyzed Soy Protein, Sodium Cocoyl Hydrolyzed Sweet Almond Protein, Sodium Cocoyl Hydrolyzed Wheat Protein, Sodium Cocoyl Hydrolyzed Wheat Protein Glutamate, Sodium Cocoyl Isethionate, Sodium Cocoyl Methylaminopropionate, Sodium Cocoyl Oat Amino Acids, Sodium Cocoyl/Palmoyl/Sunfloweroyl Glutamate, Sodium Cocoyl Proline, Sodium Cocoyl Sarcosinate, Sodium Cocoyl Taurate, Sodium Cocoyl Threoninate, Sodium Cocoyl Wheat Amino Acids, Sodium C12-14 Olefin Sulfonate, Sodium C14-16 Olefin Sulfonate, Sodium C14-18 Olefin Sulfonate, Sodium C16-18 Olefin Sulfonate, Sodium Cornamphopropionate, Sodium Cottonseedamphoacetate, Sodium C13-15 Pareth-8 Butyl Phosphate, Sodium C9-11 Pareth-6 Carboxylate, Sodium C11-15 Pareth-7 Carboxylate, Sodium C12-13 Pareth-5 Carboxylate, Sodium C12-13 Pareth-8 Carboxylate, Sodium C12-13 Pareth-12 Carboxylate, Sodium C12-15 Pareth-6 Carboxylate, Sodium C12-15 Pareth-7 Carboxylate, Sodium C12-15 Pareth-8 Carboxylate, Sodium C14-15 Pareth-8 Carboxylate, Sodium C12-14 Sec-Pareth-8 Carboxylate, Sodium C14-15 Pareth-PG Sulfonate, Sodium C12-:13 Pareth-2 Phosphate, Sodium C13-15 Pareth-8 Phosphate, Sodium C9-15 Pareth-3 Sulfate, Sodium C10-15 Pareth Sulfate, Sodium C10-16 Pareth-2 Sulfate, Sodium C12-13 Pareth Sulfate, Sodium C12-15 Pareth Sulfate, Sodium C12-15 Pareth-3 Sulfate, Sodium C13-15 Pareth-3 Sulfate, Sodium C:12-14 Sec-Pareth-3 Sulfate, Sodium C12-15 Pareth-3 Sulfonate, Sodium C12-15 Pareth-7 Sulfonate, Sodium C12-15 Pareth-15 Sulfonate, Sodium Deceth-2 Carboxylate, Sodium Deceth Sulfate, Sodium Decylbenzenesulfonate, Sodium Decylglucosides Hydroxypropyl Phosphate, Sodium Decylglucosides Hydroxypropylsulfonate, Sodium Dilaureth-7 Citrate, Sodium Dilaureth-10 Phosphate, Sodium Dilinoleamidopropyl PG-Dimonium Chloride Phosphate, Sodium Dilinoleate, Sodium Dioleth-8 Phosphate, Sodium Dodecylhenzenesulfonate, Sodium Ethyl 2-Sulfolaurate, Sodium Glyceryl Oleate Phosphate, Sodium Grapeseedamidopropyl PG-Dimonium Chloride Phosphate, Sodium Grapeseedamphoacetate, Sodium Grapeseedate, Sodium Hempseedamphoacetate, Sodium Hexeth-4 Carboxylate, Sodium Hydrogenated Cocoate, Sodium Hydrogenated Cocoyl Methyl Isethionate, Sodium Hydrogenated Palmate, Sodium Hydrogenated Tallowate, Sodium Hydrogenated Tallowoyl Glutamate, Sodium Hydroxylauryldimonium Ethyl Phosphate, Sodium Hydroxypropyl Palm Kernelate Sulfonate, Sodium Hydroxypropylphosphate Decylglucoside Crosspolymer, Sodium Hydroxypropylphosphate Laurylglucoside Crosspolymer, Sodium Hydroxypropylsulfonate Cocoglucoside Crosspolymer, Sodium Hydroxypropylsulfonate Decylglucoside Crosspolymer, Sodium Hydroxypropylsulfonate Laurylgiucoside Crosspolymer, Sodium Hydroxystearate, Sodium Isostearate, Sodium Isosteareth-6 Carboxylate, Sodium Isosteareth-11 Carboxylate, Sodium Isostearoamphoacetate, Sodium Isostearoamphopropionate, Sodium N-Isostearoyl Methyltaurate, Sodium Laneth Sulfate, Sodium Lanolate, Sodium Lardate, Sodium Lauramido Diacetate, Sodium Lauraminopropionate, Sodium Laurate, Sodium Laureth-3 Carboxylate, Sodium Laureth-4 Carboxylate, Sodium Laureth-5 Carboxylate, Sodium Laureth-6 Carboxylate, Sodium Laureth-8 Carboxylate, Sodium Laureth-11 Carboxylate, Sodium Laureth-12 Carboxylate, Sodium Laureth-13 Carboxylate, Sodium Laureth-14 Carboxylate, Sodium Laureth-16 Carboxylate, Sodium Laureth-17 Carboxylate, Sodium Laureth Sulfate, Sodium Laureth-5 Sulfate, Sodium Laureth-7 Sulfate, Sodium Laureth-8 Sulfate, Sodium Laureth-12 Sulfate, Sodium Laureth-40 Sulfate, Sodium Laureth-7 Tartrate, Sodium Lauriminodipropionate, Sodium Lauroamphoacetate, Sodium Lauroamphohydroxypropylsulfonate, Sodium Lauroampho PG-Acetate Phosphate, Sodium Lauroamphopropionate, Sodium Lauroyl Aspartate, Sodium Lauroyl Collagen Amino Acids, Sodium Lauroyl Glycine Propionate, Sodium Lauroyl Hydrolyzed Collagen, Sodium Lauroyl Hydrolyzed Silk, Sodium Lauroyl Hydroxypropyl Sulfonate, Sodium Lauroyl Isethionate, Sodium Lauroyl Methylaminopropionate, Sodium Lauroyl Methyl Isethionate, Sodium Lauroyl Millet Amino Acids, Sodium Lauroyl/Myristoyl Aspartate, Sodium Lauroyl Oat Amino Acids, Sodium Lauroyl Sarcosinate, Sodium Lauroyl Silk Amino Acids, Sodium Lauroyl Taurate, Sodium Lauroyl Wheat Amino Acids, Sodium Lauryl Diethylenediaminoglycinate, Sodium Lauryl Glucose Carboxylate, Sodium Laurylglucosides Hydroxypropyl Phosphate, Sodium Laurylglucosides Hydroxypropylsulfonate, Sodium Lauryl Glycol Carboxylate, Sodium Lauryl Hydroxyacetamide Sulfate, Sodium Lauryl Phosphate, Sodium Lauryl Sulfate, Sodium Lauryl Sulfoacetate, Sodium Linoleate, Sodium Macadamiaseedate, Sodium Mangoamphoacetate, Sodium Mangoseedate, Sodium/MEA Laureth-2 Sulfosuccinate, Sodium Methoxy PPG-2 Acetate, Sodium Methyl Cocoyl Taurate, Sodium Methyl Lauroyl Taurate, Sodium Methyl Myristoyl Taurate, Sodium Methyl Oleoyl Taurate, Sodium Methyl Palmitoyl Taurate, Sodium Methyl Stearoyl Taurate, Sodium Methyl 2-Sulfolaurate, Sodium Methyl 2-Sulfopalmitate, Sodium Methyltaurate Isopamitamide, Sodium Methyltaurine Cocoyl Methyltaurate, Sodium Myreth Sulfate, Sodium Myristate, Sodium Myristoamphoacetate, Sodium Myristoyl Glutamate, Sodium Myristoyl Hydrolyzed Collagen, Sodium Myristoyl isethionate, Sodium Myristoyl Sarcosinate, Sodium Myristyl Sulfate, Sodium Nonoxynol-6 Phosphate, Sodium Nonoxynol-9 Phosphate, Sodium Nonoxynol-1 Sulfate, Sodium Nonoxynol-3 Sulfate, Sodium Nonoxynol-4 Sulfate, Sodium Nonoxynol-6 Sulfate, Sodium Nonoxynol-8 Sulfate, Sodium Nonoxynol-10 Sulfate, Sodium Nonoxynol-25 Sulfate, Sodium Octoxynol-2 Ethane Sulfonate, Sodium Octoxynol-2 Sulfate, Sodium Octoxynol-6 Sulfate, Sodium Octoxynol-9 Sulfate, Sodium Oleate, Sodium Oleoamphoacetate, Sodium Oleoamphohydroxypropylsulfonate, Sodium Oleoamphopropionate, Sodium Oleoyl Hydrolyzed Collagen, Sodium Oleoyl Isethionate, Sodium Oleth Sulfate, Sodium Oleyl Methyl Isethionate, Sodium Oleyl Sulfate, Sodium Olivamphoacetate, Sodium Olivate, Sodium Olivoyl Glutamate, Sodium Palmamphoacetate, Sodium Palmate, Sodium Palm Glyceride Sulfonate, Sodium Palmitate, Sodium Palmitoyl Hydrolyzed Collagen, Sodium Palmitoyl Hydrolyzed Wheat Protein, Sodium Palmitoyl Sarcosinate, Sodium Palm Kernelate, Sodium Palm Kerneloyl Isethionate, Sodium Palmoyl Glutamate, Sodium Passiflora Edulis Seedate, Sodium Peanutamphoacetate, Sodium Peanutate, Sodium PEG-6 Cocamide Carboxylate, Sodium PEG-8 Cocamide Carboxylate, Sodium PEG-4 Cocamide Sulfate, Sodium PEG-3 Lauramide Carboxylate, Sodium PEG-4 Lauramide Carboxylate, Sodium PEG-8 Palm Glycerides Carboxylate, Sodium Pentaerythrityl Hydroxypropyl Iminodiacetate Dendrimer, Sodium Propoxy PPG-2 Acetate, Sodium Rapeseedate, Sodium Ricebranamphoacetate, Sodium Ricinoleate, Sodium Ricinoleoamphoacetate, Sodium Rose Hipsamphoacetate, Sodium Rosinate, Sodium Safflowerate, Sodium Saffioweroyl Hydrolyzed Soy Protein, Sodium Sesameseedate, Sodium Sesamphoacetate, Sodium Sheabutteramphoacetate, Sodium Soyate, Sodium Soy Hydrolyzed Collagen, Sodium Stearate, Sodium Stearoamphoacetate, Sodium Stearoamphohydroxypropylsulfonate, Sodium Stearoamphopropionate, Sodium Stearoyl Casein, Sodium Stearoyl Glutamate, Sodium Stearoyl Hyaluronate, Sodium Stearoyl Hydrolyzed Collagen, Sodium Stearoyl Hydrolyzed Corn Protein, Sodium Stearoyl Hydrolyzed Silk, Sodium Stearoyl Hydrolyzed Soy Protein, Sodium Stearoyl Hydrolyzed Wheat Protein, Sodium Stearoyl Lactalbumin, Sodium Stearoyl Methyl Isethionate, Sodium Stearoyl Oat Protein, Sodium Stearoyl Pea Protein, Sodium Stearoyl Soy Protein, Sodium Stearyl Dimethyl Glycine, Sodium Stearyl Sulfate, Sodium Sunflowerseedamphoacetate, Sodium Surfactin, Sodium Sweetalmondamphoacetate, Sodium Sweet Almondate, Sodium Tallamphopropionate, Sodium Tallate, Sodium Tallowamphoacetate, Sodium Tallowate, Sodium Tallow Sulfate, Sodium Tamanuseedate, Sodium Taurate, Sodium Taurine Cocoyl Methyltaurate, Sodium Taurine Laurate, Sodium/TEA-Lauroyl Collagen Amino Acids, Sodium/TEA-Lauroyl Hydrolyzed Collagen, Sodium/TEA-Lauroyl Hydrolyzed Keratin, Sodium/TEA-Lauroyl Keratin Amino Acids, Sodium/TEA-Undecylenoyl Collagen Amino Acids, Sodium/TEA-Undecylenoyl Hydrolyzed Collagen, Sodium/TEA-Undecylenoyl Hydrolyzed Corn Protein, Sodium/TEA-Undecylenoyl Hydrolyzed Soy Protein, Sodium/TEA-Undecylenoyl Hydrolyzed Wheat Protein, Sodium Theobroma Grandiflorum Seedate, Sodium Trideceth-3 Carboxylate, Sodium Trideceth-4 Carboxylate, Sodium Trideceth-6 Carboxylate, Sodium Trideceth-7 Carboxylate, Sodium Trideceth-8 Carboxylate, Sodium Trideceth-12 Carboxylate, Sodium Trideceth-15 Carboxylate, Sodium Trideceth-19 Carboxylate, Sodium Trideceth Sulfate, Sodium Tridecylbenzenesulfonate, Sodium Tridecyl Sulfate, Sodium Trimethylolpropane Hydroxypropyl Iminodiacetate Dendrimer, Sodium Undeceth-5 Carboxylate, Sodium Undecylenate, Sodium Undecylenoamphoacetate, Sodium Undecylenoamphopropionate, Sodium Undecylenoyl Glutamate, Sodium Wheat Germamphoacetate, Sorbeth-160 Tristearate, Soy Acid, Soyamidopropylamine Oxide, Soyamidopropyl Betaine, Soybean Oil Glycereth-8 Esters, Stearamidopropylamine Oxide, Stearamidopropyl Betaine, Stearamine Oxide, Steareth-15, Steareth-16, Steareth-20, Steareth-21, Steareth-25, Steareth-27, Steareth-30, Steareth-40, Steareth-50, Steareth-80, Steareth-100, Steareth-2 Phosphate, Steareth-3 Phosphate, Stearic Acid, Stearoxypropyltrimonium Chloride, Stearoyl Glutamic Acid, Stearoyl Sarcosine, Stearyl Betaine, Stearyldimoniumhydroxypropyl Butylglucosides Chloride, Stearyldimoniumhydroxypropyl Decylglucosides Chloride, Stearyldimoniumhydroxypropyl Laurylglucosides Chloride, Sulfated Castor Oil, Sulfated Coconut Oil, Sulfated Glyceryl Oleate, Sulfated Olive Oil, Sulfated Peanut Oil, Sunfloweramide MEA, Sunflower Seed Acid, Sunflowerseedamidopropyl Hydroxyethyldimonium Chloride, Sunflower Seed Oil Glycereth-8 Esters, Tall Oil Acid, Tallow Acid, Tallowamidopropylamine Oxide, Tallowamidopropyl Betaine, Tallowamidopropyl Hydroxysultaine, Tallowamine Oxide, Tallow Betaine, Tallow Dihydroxyethyl Betaine, Tallowoyl Ethyl Glucoside, TEA-Abietoyl Hydrolyzed Collagen, TEA-C12-14 Alkyl Phosphate, TEA-C10-15 Alkyl Sulfate, TEA-C11-15 Alkyl Sulfate, TEA-C12-13 Alkyl Sulfate, TEA-C12-14 Alkyl Sulfate, TEA-C12-15 Alkyl Sulfate, TEA C14-17 Alkyl Sec Sulfonate, TEA-Canolate, TEA-Cocamide Diacetate, TEA-Cocoate, TEA-Coco-Sulfate, TEA-Cocoyl Alaninate, TEA-Cocoyl Glutamate, TEA-Cocoyl Glutaminate, TEA-Cocoyl Glycinate, TEA-Cocoyl Hydrolyzed Collagen, TEA-Cocoyl Hydrolyzed Soy Protein, TEA-Cocoyl Sarcosinate, TEA-Dimethicone PEG-7 Phosphate, TEA-Dodecylbenzenesulfonate, TEA-Hydrogenated Cocoate, TEA-Hydrogenated Tallowoyl Glutamate, TEA-Isostearate, TEA-Isostearoyl Hydrolyzed Collagen, TEA-Laura minopropionate, TEA-Laurate, TEA-Laurate/Myristate, TEA-Laureth Sulfate, TEA-lauroyl Collagen Amino Acids, TEA-Lauroyl Glutamate, TEA-Lauroyl Hydrolyzed Collagen, TEA-Lauroyl Keratin Amino Acids, TEA-Lauroyl Methylaminopropionate, TEA-Lauroyl/Myristoyl Aspartate, TEA-Lauroyl Sarcosinate, TEA-Lauryl Phosphate, TEA-Lauryl Sulfate, TEA-Myristaminopropionate, TEA-Myristate, TEA-Myristoyl Hydrolyzed Collagen, TEA-Oleate, TEA-Oleoyl Hydrolyzed Collagen, TEA-Oleoyl Sarcosinate, TEA-Oleyl Sulfate, TEA-Palmitate, TEA-Palm Kernel Sarcosinate, TEA-PEG-3 Cocamide Sulfate, TEA-Rosinate, TEA-Stearate, TEA-Tallate, TEA-Tridecylbenzenesulfonate, TEA-Undecylenate, TEA-Undecylenoyl Hydrolyzed Collagen, Tetramethyl Decynediol, Tetrasodium Dicarboxyethyl Stearyl Sulfosuccinamate, TIPA-Laureth Sulfate, TIPA-Lauryl Sulfate, TIPA-Myristate, TIPA-Stearate, Tocopheryl Phosphate, Trehalose Undecylenoate, Tri-C12-15 Pareth-2 Phosphate, Tri-C12-15 Pareth-6 Phosphate, Tri-C12-15 Pareth-8 Phosphate, Tri-C12-15 Pareth-10 Phosphate, Trideceth-20, Trideceth-50, Trideceth-3 Carboxylic Acid, Trideceth-4 Carboxylic Acid, Trideceth-7 Carboxylic Acid, Trideceth-8 Carboxylic Acid, Trideceth-15 Carboxylic Acid, Trideceth-19 Carboxylic Acid, Trideceth-10 Phosphate, Tridecylbenzenesulfonic Acid, Trilaureth-9 Citrate, Trimethylolpropane Hydroxypropyl Bis-Hydroxyethylamine Dendrimer, Trisodium Lauroampho PG-Acetate Chloride Phosphate, Undecanoic Acid, Undeceth-5 Carboxylic Acid, Undecylenmnidopropylamine Oxide, Undecylenamidopropyl Betaine, Undecylenic Acid, Undecylenoyl Collagen Amino Acids, Undecylenoyl Glycine, Undecylenoyl Hydrolyzed Collagen, Undecylenoyl Wheat Amino Acids, Undecyl Glucoside, Wheat Germ Acid, Wheat Germamidopropylamine Oxide, Wheat Germamidopropyl Betaine, Yucca Schidigera Leaf/Root/Stem Extract, Yucca Schidigera Stem Extract, Zinc Coceth Sulfatea and Zinc Coco-Sulfate.

For the compounds of the group F it is more preferred that one or more compounds are selected from the group consisting of Sodium Laureth Sulfate, Cocamidopropyl Betaine, Sodium Cocoamphoacetate, CocoGiucoside and Ammonium Laury Sulfosuccinate.

It has to be noted that it is in the sense of the invention that in the preferred mixtures there may be comprised one or more compounds of one, two, three, four or all of the groups to B-F. With the preferred or more preferred compounds of group B-F an improved and more improved enhancing effect for the sum of cooling sensation can be achieved.

Very good enhancement effects for the cooling sensation can be attained if there are certain ratios (by weight) from the cooling substance to the sum of the compounds of groups B, C, D, E or F.

Preferred, more preferred and most preferred ratios are listed in the following table, wherein better effects can be attained with the more preferred and the best effects can be attained with the most preferred ratios.

TABLE B

Preferred ratios of Cooling substance to Abrasives, Tensides, Terpenes/Musk, Silicon Oil

| Abrasives (GroupE) | Tensides (Group F) | Terpenes and/or Musks (Group C/D) | Silicone Oil (Group B) |
| --- | --- | --- | --- |
| A: 1:0.01 to 1:1000 | A: 1:0.01 to 1:1000 | A: 1:0.01 to 1:1000 | A: 1:0.01 to 1:1000 |
| B: 1:0.1 to 1:100 | B: 1:0.1 to 1:100 | B: 1:0.1 to 1:10 | B: 1:0.1 to 1:100 |
| C: 1:1 to 1:30 | C: 1:1 to 1:30 | C.: 1:0.2 to 1:5 | C: 1:0.2 to 1:50 |

A: preferably
B: more preferably
C: most preferably

It has to be noted that the ratios in the above table B refer to all compounds of a specific group as a sum (e.g. all tensides according to group F). According to the invention it is further preferred if there are compounds of more than one of the groups B-F contained in the mixture according to the invention that for two, three, four or all of these groups the preferred, the more preferred or the most preferred ratios are set in the mixture.

For achieving a good cooling effect in the sense of the invention certain ratios of polyols (compounds of group A) to compounds of group B, C, D, E or F are preferred.

TABLE C

Preferred ratios of Polyols (Group A) to Abrasives, tensides, terpenes/Musk, Silicon Oil in mixtures

| Abrasives (GroupE) | Tensides (Group F) | Terpenes and/or Musks (Group C/D) | Silicone Oil (Group B) |
| --- | --- | --- | --- |
| A: 1:0.01 to 1:1000 | A: 1:0.01 to 1:1000 | A: 1:0.001 to 1:15 | A: 1:0.01 to 1:1000 |
| B: 1:0.1 to 1:100 | B: 1:0.1 to 1:100 | B: 1:0.005 to 1:10 | B: 1:0.1 to 1:100 |
| C: 1:1 to 1:10 | C: 1:0.1 to 1:10 | C: 1:0.01 to 1:3 | C: 1:012 to 1:20 |

A: preferably
B: more preferably
C: most preferably

For the ratios depicted in table C the above said regarding the ratios depicted in table B is applicable in an analog way.

It is further preferred that in mixtures according to the invention the ratios of table B and table C (dependent thereof from which groups there are members contained in the mixture) are both present.

Part of the invention is also a cosmetic composition comprising a cooling mixture according to the invention.

Also part of the invention is a sanitary article comprising a cooling mixture according to the invention.

Preferred cosmetic compositions are hair care products and skin care products, preferred sanitary articles are sanitary towels, tampons and nappies, in particular baby nappies.

For cosmetic compositions it is preferred if the proportion of 5-methyl-2-(propane-2-yl)cyclohexyl-N-ethyloxamate in the overall composition is in the range of 0.001 to 20, preferably of 0.01 to 10 and especially of 0,1 to 5% by wt. respectively in relation to the overall weight of the cosmetic composition.

For sanitary articles it is preferred if the proportion of 5-methyl-2-(propane-2-yl)cyclohexyl-N-ethyloxamate in the overall composition is in the range of 0.000001 to 20, preferably of 0.0001 to 10 and especially of 0.001 to 5% by wt. respectively in relation to the overall weight of the sanitary article.

In cosmetic compositions according to the invention and sanitary articles according to the invention it is in general preferred that the amount of coding substance is 0.01-3 wt.-% and/or the amount of polyols of group A is 0.1-50 wt.-%, wherein each wt.-% is applied to the total weight of the cosmetic composition or the sanitary article. If the mixture according to the invention comprises compounds of one or more of groups B-F it is preferred that the compounds of group B (silicone oil) all together are present in an amount of 1-50 wt-%, the compounds of the group C (terpenes) and/or D (musk) all together are present in an amount of 0.0:1-5 wt.-%, the compound of group F (abrasives) all together are present in an amount 0.1-35 wt.-% and the compounds of group F (tensides) all together are present in an amount of 0.1-30 wt.-%, wherein each wt.-% is applied to the total weight of the cosmetic composition or the sanitary article.

Cooling Skin and Hair Care Products

According to a preferred embodiment, the compositions according to the invention are a cooling skin or hair care product or cleansing agent.

Preferred skin or hair cleansing compositions are soaps having a liquid to gel type consistency, in particular transparent soaps, luxurious soaps, deodorant soaps, cream soaps, baby soaps, skin protection soaps, abrasive soaps and syndets, pasty soaps, soft soaps, washing pastes, peeling soaps, liquid wash, shower and bath preparations such as wash lotions, shower baths and shower gels, foam baths, oil baths and scrub preparations, shaving foams, lotions and creams.

According to a further preferred embodiment this is a shower gel, a shampoo formulation or a bath preparation. Such compositions according to the invention contain at least one cooling mixture according to the invention as well as usually anionic surfactants as primary surfactants and amphoteric and/or non-ionic surfactants as co-surfactants. Further suitable active substances and/or auxiliary agents are generally selected from lipids, perfume oils, colorants, organic acids, preservatives and antioxidants as well as from thickeners/gel formers, skin conditioners and moisture retainers.

Special Embodiments for Skin Care Products

Suitable skin cosmetic compositions are for example toners, face masks, deodorants and other cosmetic lotions, compositions for the use in decorative cosmetics comprise for example blemish sticks, studio pigments, mascara and eye shadows, lipsticks, eye liner pens, eyeliner, rouges, powder and eyebrow pencils.

Moreover, the compositions according to the invention may be used in nose strips for pore cleaning, in anti-acne products, repellents, shaving products, after- and pre-shave care products, after-sun care products, hair removing agents, hand cleaning products, hair dyes, intimate hygiene products, foot care products as well as in baby care products.

The skin care products according to the invention are preferably W/O or O/W skin creams, day and night creams, eye creams, face creams, anti-wrinkle creams, sun protection creams, moisture retention creams, after shave, bleaching creams, self-tanning creams, vitamin creams, skin lotions, care lotions and moisture retention lotions.

Depending on the area of application, the compositions according to the invention may be applied in a form suitable for skin care, such as for example as a cream, foam, gel, stick, mousse, milk, spray (pump spray or a spray containing a blowing agent) or as a lotion.

Apart from the cooling mixtures according to the invention and suitable carriers, the compositions according to the invention may contain also further active substances and auxiliary agents that are in customary use in skin cosmetics, in particular as described above, These include preferably emulsifiers, preservatives, perfume oils, active cosmetic substances such as phytantriol, vitamins A, F and C, retinol, bisabolol, panthenol, sun screen compositions, bleaching products, dyestuffs, toning agents, tanning agents, collagen, enzymes, protein hydrolysate, stabilizing agents, pH regulators, dyestuffs, salts, thickeners, gel formers, consistency agents, silicones, moisture retaining agents, re-moisturizing agents and further customary additives.

Preferred oil and fat components of the skin cosmetic compositions according to the invention are the above-mentioned mineral and synthetic oils such as for example paraffins, silicone oils and aliphatic hydrocarbons having more than 8 carbon atoms, animal and vegetable oils such as for example sunflower oil, coconut oil, avocado oil, olive oil, lanolin or waxes, fatty acids, fatty acid esters such as for example triglycerides of C6-C30 fatty acids, wax ester such as for example jojoba oil, fatty alcohols, vaseline, hydrogenated lanolin and acetylated lanolin as well as mixtures thereof.

In order to achieve certain properties such as an improved feel to touch, spreading, water resistance and/or binding of active substances and auxiliary agents, such as for example pigments, the skin cosmetic compositions according to the invention may additionally also contain conditioning substances on the basis of silicone compounds. Suitable silicone compounds are in particular polyalkyl siloxanes, polyaryl siloxanes, polyarylalkyl siloxanes, polyether siloxanes or silicone resins.

The preparation of the cosmetic compositions according to the invention is carried out according to customary methods as known by a person skilled in the art.

For the preparation of the compositions according to the invention, the active substances may be mixed or diluted with a suitable auxiliary agent (excipient). Excipients may be solid, semi-solid or liquid materials which may be used as a vehicle, carrier or medium for the active substances. The admixture of further auxiliary agents may, if desired, be carried out in a manner known to a person skilled in the art. In addition, polymers and dispersions are suitable, as auxiliary agents in pharmacy, preferably as or in (a) coating agent(s) or as (a) binder(s) for solid dosage forms. They may also be used as tablet coating agents and tablet binding agents.

Preferably, the cosmetic compositions according to the invention are present in the form of emulsions, in particular as water-in-oil (W/O) or oil-in-water (O/W) emulsions. However, it is also possible to select other types of formulations, for example gels, oils, oleogels, multiple emulsions, for example in the form of W/O/W or O/W/O emulsionen, anhydrous ointments or ointment bases etc. Also emulsifier-free formulations such as hydrodispersions, hydrogels or a Pickering emulsion are advantageous embodiments.

The preparation of emulsions is carried out according to known methods. Apart from at least one active substance according to the invention, the emulsions contain as a rule usual components such as fatty alcohols, fatty acid esters and in particular fatty acid triglycerides, fatty acids, lanolin and derivatives thereof, natural or synthetic oils or waxes and emulsifiers in the presence of water. The selection of emulsion type specific additives and the preparation of suitable emulsions are described, for example, in Schrader, Grundlagen and Rezepturen der Kosmetika, Huthig Buch Verlag, Heidelberg, 2.sup.nd edition, 1989, part three, to which reference is herewith explicitly made.

A suitable emulsion as a W/O emulsion, for example for a skin cream etc. generally includes an aqueous phase which is emulsified by means of a suitable emulsifier system in an oil or fat phase. A polyelectrolyte complex is used for providing the aqueous phase.

Preferred fatty components which may be included in the fat phase of the emulsions are: hydrocarbon oils such as paraffin oil, purcellin oil, perhydrosqualene and solutions of microcrystalline waxes in these oils; animal or vegetable oils such as sweet almond oil, avocado oil, calophyllum oil, lanolin and derivates thereof, castor oil, sesame oil, olive oil, jojoba oil, Karite oil, hoplostethus oil, mineral oils having a distillation starting point under atmospheric pressure at approx. 250.degree. C. and a distillation end point at 410.degree. C., such as for example vaseline oil, esters of saturated or unsaturated fatty acids such as alkyl myristate, e.g. i-propyl, butyl or cetyl myristate, hexadecyl stearate, ethyl or i-propyl palmitate, octane or decanoic acid triglyceride and cetyl ricinoleate.

The fat phase may contain soluble silicone oils such as dimethyl polysiloxan, methylphenyl polysiloxane and the silicone glycol copolymer, fatty acids and fatty alcohols also in other oils.

Besides the cooling mixtures according to the invention also waxes may be used, such as for example carnauba wax, candililla wax, beeswax, microcrystalline wax, Ozokerit wax and Ca, Mg and Al oleates, myristates, linoleates and stearates.

Further, a composition according to the invention may be present as an O/W emulsion. Such an emulsion usually contains an oil phase, emulsifiers which stabilize the oil phase in the water phase, and an aqueous phase which is usually present in a thickened condition. As emulsifiers, O/W emulsifiers such as polyglycerin ester, sorbitan ester or partially esterified glycerides are considered.

According to a further preferred embodiment, the compositions according to the invention may be a shower gel, a shampoo formulation or a bath preparation.

Such formulations contain at least one cooling mixture according to the invention as well as usually anionic surfactants as primary surfactants and amphoteric and/or non-ionic surfactants as co-surfactants. Further suitable active substances and/or auxiliary agents are generally selected from lipids, perfume oils, dyestuffs, organic acids, preservatives and anti-oxidants as well as from thickeners/gel formers, skin conditioners and moisture retention agents.

In the wash, shower and bath compositions according to the invention, all of the anionic, neutral, amphoteric or cationic surfactants that are usually used in body cleansing agents may be used.

Suitable anionic surfactants are for example alkyl sulfates, alkyl ether sulfates, alkyl sulfonates, alkyl aryl sulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefin sulfonates, in particular alkaline and earth alkaline metal salts, e.g. sodium, potassium, magnesium, calcium as well as ammonium and triethanolamine salts. The alkyl ether sulfates, alkyl ether phosphates and alkyl ether carboxylates may contain 1. to 10 ethylene oxide or propylene oxide units, preferably 1 to 3 ethylene oxide units in a molecule.

These include e.g, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecyl benzol sulfonate, triethanolamine dodecyl benzol sulfonate.

Suitable amphoteric surfactants are for example alkyl betaine, alkyl amido propyle betaine, alkyl sulfobetaine, alkyl glycinate, alkyl carboxy glycinates, alkyl amphoacetates or propionates, alkyl amphodiacetates or dipropionates.

For example, coca dimethyl sulfopropyl betaine, lauryl betaine, cocamido propyl betaine or sodium cocoamphopropionate may be used, As non-ionic surfactants for example the reaction products of aliphatic alcohols or alkyl phenols having 6 to 20 C atoms in the alkyl chain, which may be linear or branched, with ethylene oxide and/or propylene oxide are suitable. The amount of alkylene oxide is approx. 6 to 60 moles per mole of alcohol, Further, alkyl amine oxides, mono- or dialkyl alkanolamides, fatty acid esters of polyethylene glykolen, ethoxylated fatty acid amides, alkyl polyglycosides or sorbitan ether ester are suitable.

Moreover, the wash, shower and bath compositions according to the invention may contain usual cationic surfactants such as for example quaternary ammonium compounds, for example cetyl trimethyl ammonium chloride.

Further, the shower gel/shampoo formulations may contain a thickener such as e.g. common salt, PEG-55, propylene glycol oleate, PEG-120 methyl lucose ioleate and others as well as preservatives, further active substances and auxiliary agents and water.

Cosmetic compositions according to the invention in terms of a skin care product may also be sun protection compositions. It will be clear to a person skilled in the art that sun protection compositions may also be use for purposes other than skin care. In terms of the present application, however, sun protection compositions are understood to be skin care products (in the broadest possible sense). Sun protection compositions according to the invention comprise a cooling mixture according to the invention.

Advantageously, these compositions contain at least one UVA filter and/or at least one UVB filter and/or at least one inorganic pigment. The composition may here be present in different forms, such as are usually used for example for sun protection compositions. Thus, they may form for example a solution, an emulsion of the water-in-oil (W/O) or of the oil in water (O/W) type, or a multiple emulsion, for example of the water-in-oil-in-water (W/O/W) type, a gel, a hydrodispersion, a solid stick or an aerosol. The sun protection compositions according to the invention may particularly advantageously be combined with substances which absorb or reflect UV radiation, wherein the overall amount of the filter substances is 0.01% by wt. to 40% by wt., preferably 0.1% to 10% by wt., in particular 1.0 to 5.0% by wt. in relation to the overall weight of the compositions, in order to provide cosmetic compositions which protect the hair or the skin from ultraviolet radiation. Advantageously, these compositions contain at least one UVA filter and/or at least one UVB filter and/or at least one enorganic pigment, so that a sun protection factor of at least greater or equal 2 (preferably greater or equal 5) is achieved. These compositions according to the invention may be present here in different forms as are customarily used for example for sun protection compositions. Thus, they may constitute for example a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or an aerosol.

Advantageous UV filters are UVB filters such as for example:
- p-aminobenzoic acid,
- p-aminobenzoic acid ethyl ester (25 mole) ethoxylated,
- p-dimethyl aminobenzoic acid-2-ethyl hexyl ester,
- p-aminobenzoic acid ethyl ester (2 mole) N-propoxylated,
- p-aminobenzoic acid glycerine ester,
- salicylic acid homomethyl ester (homosalate) (Neo Heliopan® HMS),
- salicylic acid-2-ethyl hexyl ester (Neo Heliopan® OS),
- triethanol amino salicylate,
- 4-isopropyl benzyl salicylate,
- anthranilic acid menthyl ester (Neo Heliopan® MA),
- diisopropyl cinnamic acid ethyl ester,
- p-methoxy cinnamic acid-2-ethyl hexyl ester (Neo Heliopan® AV),
- diisopropyl cinnamic acid methyl ester,
- p-methoxy cinnamic acid isoamyl ester (Neo Heliopan® E 1000),
- p-methoxy cinnamic acid diethanol amine salt,
- p-methoxy cinnamic acid isopropyl ester,
- 2-phenyl benzimidazol sulfonic acid and salts (Neo Heliopan® Hydro),
- 3-(4'-trimethyl ammonium)-benzyliden-bornan-2-one-methyl sulfate,
- β.-imidazol-4(5)-acrylic acid (urocanic acid),
- 3-(4'-sulfo)benzyliden-bornan-2-one and salts,
- 3-(4'-methyl benzylidene)-d,l-camphor (Neo Heliopan® MBC),
- 3-benzylidene-d,l-camphor,
- N-[(2 and 4)-[2-(oxoborn-3-yliden methyl]benzyl]-acrylamide polymer,
- 4,4'-[(6-[4-(1,1-dimethyl)-aminocarbonyl)-phenylamino]-1,3,5-triazin-2,4-diyl)diimino]-bis-(benzoic acid-2-ethyl hexyl ester) (Uyasorb® HEB),
- benzylidene malonate polysiloxan (Parsor® SLX),
- glyceryl ethyl hexanoate dimethoxy cinnamate,
- dipropylene glycol salicylate,
- tris(2-etyl hexyl)-4,4",4"'-(1,35-triazin-2,4,6-triyl-triimino)tribenzoat (Uvinul® T150).

Broadband filters such as for example:
- 2-ethyl hexyl-2-cyano-3,3-diphenyl acrylate (Neo Hellopan® 303),
- ethyl-2-cyano-3,3'-diphenyl acrylate,
- 2-hydroxy-4-methoxy benzophenone (Neo Heliopan® BB),
- 2-hydroxy-4-methoxy benzophenone-5-sulfonic acid,
- dihydroxy-4-methoxy benzophenone,
- 2,4-dihydroxy benzophenone,
- tetrahydroxy benzophenone,
- 2,2'-dihydroxy-4,4'-dimethoxy benzophenone,
- 2-hydroxy-4-n-octoxy enzophenone,
- 2-hydroxy-4-methoxy-4'-methyl benzophenone,
- sodium hydroxylmethoxy benzophenone sulfonate,
- disodium-2,2'-dihydroxy-4,4'-dimethoxy-5,5'-disufto-benzophenone,
- phenol,-(2H-benztriazol-2-yl)-4-methyl-6-(2-methyl-3 (1,3,3,3-tetramethyl-1-(trimethylsilyl)-oxy)-disiloxa-nyl)-propyl), (Mexoryr® XL)
- 2,2'-methylene-bis-(6-(2H-benztriazol-2-yl)-4-1,1,3,3-te-tramethylbutyl)-phenol), (Tinosorb® M),
- 2,4-bis-[4-(2-ethyl hexyloxy)-2-hydroxyphenyl]-1,3,5-triazine,
- 2,4-bis-[{(4-(2-Ethyl-hexyloxy)-2-hydroxyl}-phenyl]-6-(4-methoxyphenyl)-1,3,5-triazine, (Tinosorb® S),
- 2,4-bis-[{(4-(3-sulfonato)-2-hydroxy-propyloxy)-2-hydroxyl}-phenyl]-6-(4-methoxyphenyl)-1,3,5-triazine sodium salt,
- 2,4-bis-[{(3-(2-propyloxy)-2-hydroxy-propyloxy)-2-hydroxyl}-phenyl]-6-(4-methoxy-phenyl)-1,3,5-triazine,
- 2,4-bis-[{4-(2-ethyl-hexyloxy)-2-hydroxy}-phenyl]-6-[4-(2-methoxyethyl-carbonyl)-phenylamino]-1,3,5-triazine
- 2,4-bis-[{4-(3-(2-propyloxy)-2-hydroxy-propyloxy)-2-hydroxyl}-phenyl]-6-4-(2-ethylcarboxyl)-phenylami-nol-1,3,5-triazine,
- 2,4-bis-[{4-(2-ethyl-hexyloxy)-2-hydroxy}-phenyl]-6-(1-methyl-pyrrol-2-yl)-1,3,5-triazine,
- 2,4-bis-[{4-tris-(trimethylsiloxy-silylpropyloxy)-2-hydroxy}-phenyl]-6-(4-methoxyphenyl)-1,3,5-triazine,
- 2,4-bis-[{4-(2"-methylpropenyloxy)-2-hydroxy}-phenyl]-6-(4-methoxyphenyl)-1,3,5-triazine,
- 2,4-bis-[{4-(1',1',1',3'5',5',5'-heptamethylsiloxy-2"-methyl-propyloxy)-2-hydroxy}-phenyl]-6-(4-methoxyphenyl)-1,3,5-triazine.

UVA filters such as for example:
- 4-isopropyl dibenzoyl methane,
- terephthalylidene-dibornan sulfonic acid and salts (Mexoryl• SX)
- 4-t-butyl-4'-methoxy-dibenzoyl methane (Avobenzon)/ (Neo 1-leliopan® 357),
- phenylene-bis-benzimidazyl-tetrasulfonic acid disodium salt (Neo Heliopan° AP),
- 2,2'-(1,4-phenylene)-bis-(1H-benzimidazol-4,6-disulfo-nic acid), monosodium salt,
- 2-(4-diethylamine-2-hydroxybenzoyl)benzoic acid hexy-lester (Uvinul® A Plus),
- Indanylidene compounds according to DE 100 55 940 (=WO 02/38537).

Here, UV absorbers particularly suitable for a combination are:
- p-aminobenzoic acid,
- 3-(4'-trimethyl ammonium)-benzylidene-bornan-2-one-methyl sulfate,
- salicylic acid homomethyl ester (Neo Heliopan® CHMS),
- 2-hydroxy-4-methoxy-benzophenone (Neo Heliopan® BB),
- 2-phenyl benzimidazol sulfonic acid (Neo Heliopan® Hydro),
- terephthalylidene-dibornan sulfonic acid and salts (Mexoryl® SX),
- 4-tert.-butyl-4'-methoxy dibenzoyl methane (Neo Heliopan® 357,
- 3-(4'-suffo)benzylidene-bornan-2-one and salts,
- 2-ethyl hexyl-2-cyano-3,3-diphenyl acrylate (Neo Heliopan® 303),
- N-[(2 and 4)-[2-(oxobom-3-ylidene)methyl]benzyl]-acry-lamide polymer,
- p-methoxy cinnamon acid-2-ethyl hexyl ester (Neo Heliopan® AV),
- p-aminobenzoic acid ethyl ester (25 mole) ethoxylated,
- p-methoxy cinnamon acid isoamyl ester (Neo Heliopan® E1000),
- 2,4,6-trianilino-(p-carbo-2'-ethyl hexyl-1'-oxy)-1,3,5-tri-azine (Uylnul® T150),
- phenol, 2-(2H-benzotriazol-2-yl)-4-methyl-6-(2-methyl-3 (1,3,3,3-tetramethyl-1-(trimethylsilyl)-oxy)-disiloxa-nyl)-propyl), (Mexoryl® XL),
- 4,4'-[(6-[4-(1,1-dimethyl)-aminocarbonyl)-phe-nylamino]-1,3,5-triazine-2,4-diyl)-diimino]-bis-(ben-zoic acid-2-ethyl hexyl ester), (Uyasorb® HEB), 3-(4'-methyl benzylidene)-d,l-camphor (Neo Helipan® MBC),
3-benzylidene camphor,
salicylic acid-2-ethyl hexyl ester (Neo Helipan® OS),
4-dimethyl aminobenzoic acid-2-ethyl hexyl ester (Padimate O),
hydroxy-4-methoxy-benzophenone-5-sulfonic acid and Na salt,
2,2'-methylene-bis-(6-(2H-benztriazol-2-yl)-4-1,1,3,3-tetramethylbutyl)-phenol), (Tinosorb® M),
phenylene-bis-benzimidazyl-tetrasulfonic add disodium salt (Neo Heliopan® AP),
2,4-bis-[{(4-(2-ethyl-hexyloxy)-2-hydroxyl}-phenyl]-6-(4-methoxyphenyl)-1,3,5-triazine, (Tinosorb® S),
benzylidene malonate polysiloxane (Parsol® SLX),
menthyl anthranilate (Neo Heliopan® MA),
2-(4-diethylamino-2-hydroxybenzoyl)benzoic acid hexyl ester (Uvinul® A Plus),
indanylidene compounds according to DE 100 55 940 (=WO 02/38537).

Advantageous inorganic light protection pigments are finely dispersed metal oxides and metal salts, for examples titanium dioxides, zinc oxide (ZnO), iron oxides (e.g. $Fe_2O_3$), aluminum oxide ($Al_2O_3$); cerium oxides (e.g. $Ce_2O_3$), manganese oxides (e.g. MnO), zirconium oxide ($ZrO_2$), silicon oxide ($SiO_2$), mixed oxides of the corresponding metals as well as mixtures of such oxides, barium sulfate and zinc stearate. Particularly preferably these are pigments on the basis of $TiO_2$ or zinc oxide. In preferred embodiments, the particles have an average diameter of less than 100 nm, preferably between 5 and 50 nm and particularly preferably between 15 and 30 nm. They may have a spherical shape; however, also particles having an ellipsoidal shape or a shape deviating from the spherical shape in other ways may be used. The pigments may also be present in a form in which they are surface treated, i.e. hydrophilized or hydrophobized. Typical examples include coated titanium dioxides such as for example titanium dioxide T 805 (Degussa) or Eusolex® T2000 (Merck) or coated zinc oxide such as for example zinc oxide NDM. As hydrophobic coating agents above all silicones and here especially trialkoxy octysilane or simethicone may be considered. With regard to sun protection products, so-called micro and nano pigments are preferably used. Preferably, zink micro or nano pigments are used.

The overall amount of anorganic pigments, in particular of hydrophobic anorganic micropigments in the ready-made compositions according to the invention, is advantageously in the range of 0.1 to 30% by wt., preferably 0.1 to 10.0, in particular 0.5 to 6.0% by wt. in relation to the overall weight of the composition.

Special Embodiments for Hair Care Applications

According to a further preferred embodiment, the compositions according to the invention are a hair care product (hair conditioning product).

Preferably, the hair care products according to the invention are present in the form of a styling foam, hair mousse, hair gel, shampoo, hair spray, hair foam, hair end fluid, equalizer for perms, hair dyeing and bleaching agent or "hot oil treatment". Depending on the area of application, the hair cosmetic compositions may be applied as (aerosol) spray, (aerosol) foam, gel, gel spray, cream, lotion or wax. Hair sprays include here both aerosol sprays and pump sprays without propellant gas. Hair foams include both aerosol foams and pump foams without propellant gas. Hair sprays and hair foams preferably include predominantly or exclusively water soluble or water dispersible components. If the compounds used in the hair sprays and hair foams according to the invention are dispersible in water, they may be applied in the form of aqueous micro-dispersions having particle diameters of usually 1. to 350 nm, preferably 1 to 250 nm.

The hair care products according to the invention may contain alcohol, the term alcohol is to be understood to encompass all of the alcohols that are customary in cosmetics, e.g. ethanol, isopropanol, n-propanol.

Moreover, they may contain all of the styling and conditioner polymers known in the cosmetics industry, which may be used in combination with the cooling mixtures according to the invention, if very specific properties are to be achieved.

As conventional hair cosmetic polymers, for example the above-mentioned cationic, anionic, neutral, non-ionic and amphoteric polymers are suitable, to which reference is made here.

In order to achieve certain properties, the compositions according to the invention may additionally also contain conditioning substances on the basis of silicone compounds. Suitable silicone compounds include for example polyalkyl siloxanes, polyaryl siloxanes, polyaryl alkyl siloxanes, polyether siloxanes, silicone resins or dimethicon copolyols (CTFA) and aminofunctional silicone compounds such as amodimethicone (CTFA).

The hair care products according to the invention may contain blowing agents (propellants). Blowing agents are the blowing agents that are customarily used for hair sprays or aerosol foams. Preferred are mixtures of propane/butane, pentane, dimethyl ether, 1,1-difluorethane (HFC-152 a), carbon dioxide, nitrogen or pressurized air.

As emulsifiers, any of the emulsifiers customarily used in hair foams may be used. Suitable emulsifiers may be non-ionic, cationic or anionic or amphoteric.

Examples of non-ionic emulsifiers (INCI nomenclature) include laureths, e.g. Laureth-4, ceteths, e.g. Cetheth-1, polyethylene glycol cetyl ether, cetearths, e.g. Cetheareth-25, polyglycol fatty acid glycerides, hydroxylated lecithins, lactyl ester of fatty acids, alkyl polyglycoside.

Examples of cationic emulsifiers are cetyl dimethyl-2-hydroxy ethyl ammonium dihydrogen phosphate, cetyl trimonium chloride, cetyl trimmonium bromide, cocotrimonium methyl sulfate, Quaternium-1 to x (INCI).

Anionic emulsifiers may for example be selected from the group consisting of alkyl sulfates, alkyl ether sulfates, alkyl sulfonates, alkyl aryl sulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefin sulfonates, in particular alkaline and earth alkaline metal salts, e,g. sodium, potassium, magnesium, calcium as well as ammonium and triethanol amine salts. The alkyl ether sulfates, alkyl ether phosphates and alkyl ether carboxylates may have between 1 and 10 ethylene oxide or propylene oxide units, preferably 1 to 3 ethylene oxide units in a molecule.

The use of gel formers may be of advantage, in order to achieve specific rheological or other application-specific properties of the gels. Any of the gel formers customarily used in the cosmetics industry may be used as gel formers. These include slightly cross-linked polyacrylic acid, for example carbomer (INCI), cellulose derivatives, e.g, hydroxypropyl cellulose, hydroxyethyl cellulose, cationically modified celluloses, polysaccharides, e.g. xanthan gum, caprylic/capric triglyceride, sodium-acrylate copolymers, Polyquaternium-32 (and) Paraffinum Liquidum (INCI), sodium-acrylate copolymers (and) Paraffinum Liquidum (and) PPG-1 Trideceth-6, acrylamido propyl trimonium chloride/acrylamide copolymers, Steareth-:10 allyl ether, acrylate copolymers, Polyquaternium-37 (and) Paraffinum Liquidum (and) PPG-1 Trideceth-6, Polyquaternium 37 (and) propylene glycol dicaprate dicaprylate (and) PPG-1 Trideceth-6, Polyquaternium-7, Polyquaternium-44.

Any of the anionic, neutral, amphoteric or cationic surfactants customarily used in shampoos may be used in the hair care products according to the invention embodied as shampoo formulations.

Suitable anionic surfactants include for example alkyl sulfates, alkyl ether sulfates, alkyl sulfonates, alkyl aryl sulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefin sulfonates, in particular the alkaline and earth alkaline metal salts, e.g. sodium, potassium, magnesium, calcium as well as ammonium and triethanol amine salts. The alkyl ether sulfates, alkyl ether phosphates and alkyl ether carboxylates may have between 1 and 10 ethylene oxide or propylene oxide units, preferably 1 to 3 ethylene oxide units in a molecule.

Suitable are for example sodium lauryl sulfate, ammonium lauryl sulfate, sodium lauryl ether sulfate, ammonium lauryl ether sulfate, sodium lauroyl sarcosinate, sodium oleyl succinate, ammonium lauryl sulfosuccinate, sodium dodecyl benzol sulfonate, triethanolamino dodecyl benzol sulfonate.

Suitable amphoteric surfactants include for example alkyl betaine, alkylamido propyl betaine, alkyl sulfobetaine, alkyl glycinates, alkyl carboxy glycinates, alkylamphoacetates or propionates, alkyl amphodiacetates or dipropionates.

For example, cocodimethyl sulfopropyl betaine, lauryl betaine, cocamidopropyl betaine or sodium cocamphopropionate may be used.

As non-ionic surfactants, for example the reaction products of aliphatic alcohols or alkyl phenols having 6 to 20 C atoms in the alkyl chain which may be linear or branched, with ethylene oxide and/or propylene oxide, are suitable. The amount of alkylene oxide is approx. 6 to 60 moles per mole of alcohol. Also, alkyl amine oxides, mono- or dialkyl alkanol amides, to fatty acid esters of polyethylene glycolene, alkyl polyglycosides or sorbitan ether ester are suitable.

Moreover, the shampoo formulations according to the invention may contain usual cationic surfactants such as for example quaternary ammonium compounds, for example cetyl trimethyl ammonium chloride.

In order to achieve certain effects, usual conditioners may be used in the shampoo formulations in combination with the active substances according to the invention.

These include for example the above-mentioned cationic polymers with the designation polyquaternium according to INCI, in particular copolymers of vinyl pyrrolidon/N-vinyl imidazolium salts (Luviquat FC, Luviquat HM, Luviquat MS, Luviquat Care), copolymers of N-vinyl pyrrolidon/dimethyl amino ethyl methacrylate, quaternized with diethyl sulfate (Luviquat D PQ 11), copolymers of N-vinyl caprolactam/N-vinyl pyrrolidon/N-vinyl imidazolium salts (Luviquat D Hold), cationic cellulose derivatives (Polyquaternium-4 and 10), acrylamide copolymers (Polyquaternium-7). Also, protein hydrolysates may be used as well as conditioning substances on the basis of silicone compounds, for example polyalkyl siloxanes, polyaryl siloxanes, polyaryl alkyl siloxanes, polyether siloxanes or silicone resins. Further suitable silicone compounds include dimethicon copolyols (CTFA) and aminofunctional silicone compounds such as amodimethicone (CTFA). Also, cationic guar derivatives such as guar hydroxylpropyl trimonium chloride (INCI) may be used.

Cooling Plasters as Skin Care Products

In the present invention, plasters which develop a cooling effect on the skin or on mucous membranes are also regarded as skin care products. Of course it will be obvious to a person skilled in the art that corresponding plasters may also be used for purposes other than skin care. This is explicitly included in the scope of the invention, Plasters according to the invention used as skin care products comprise a cooling mixture according to the invention. They may be designed in any desired way, for example according to the matrix system, the membrane system or the non-woven system (Drug Dev. Ind. Pharm. 14 (1988), 183-209; Drug Dev, Ind. Pharm. 13 (1987), 589-651; Drugs of Today 23 (1987), 625-646).

In its simplest form, the matrix system consists of 3 parts: the flexible backing film, the adhesive matrix containing the cooling mixture according to the invention and a peel-off film. If a non-adhesive matrix is used, an edge region of the backing film must be provided with an adhesive, in order to ensure adhesion to the skin.

By contrast, a membrane system comprises at least 5 parts: a flexible backing film, a reservoir with a dissolved or suspended cooling mixture according to the invention, a membrane for controlling the release of the active substance, an adhesive layer deposited on the membrane and a peel-off film.

In the non-woven system, the layer comprising the cooling mixture according to the invention consists of an absorbent non-woven fabric or a porous polymer which is impregnated with an active substance solution or suspension. This layer, which is firmly connected to the backing film, is covered with a peel-off film. The edge of the backing film is provided with an adhesive for application onto the skin.

In principle, all of the cooling mixtures according to the invention may be formulated in this way.

The auxiliary agents to be used are the ones that are customary for the production of plasters. Apart from the adhesive agent, as a rule a polymer having a glass temperature between −70 and −10, in particular −55 and −25.degree. C., as well as a carrier film which is coated with this adhesive agent, and the active substance, usually emulsifiers, thickeners as well as materials for controlling the release of the active substance as well as other auxiliary agents are added.

The adhesive polymers having the above-mentioned low glass temperatures are known for example from U.S. Pat. Nos. 2,973,282 and 3,307,544. The self-adhesive strips and films should adhere to the human skin merely on contact, however, the cohesion of the adhesive layer and the adhesion thereof on the carrier film should be greater than the adhesion on the skin, so that they may be peeled off as far as possible without leaving any residues. These are as a rule copolymerisates on the basis of acrylic and methacrylic acid esters of alcohols having 2 to 12, in particular 4 to 8 carbon atoms which may have a large number of other comonomers polymerized therein, for example (meth)acrylic acid, (meth)acrylic nitrile, (meth)acrylic amide, N-tert.-butyl-(methlacrylic amide, vinyl esters such as vinyl acetate, propionate or butyrate, other vinyl compounds such as styrene, further butadiene. Particular emphasis is given here to butyl acrylate and 2-ethyl hexyl acrylate. The polymers may be crosslinked by adding minor amounts of comonomers having 2 or more copolymerizable double bonds, i.e. for example of diacrylates such as butane diol diacrylate, or divinyl compounds such as divinyl benzene, or by adding other crosslinkers, for example melamine formaldehyde resins. As sticky polymers, also polyisobutylenes and polyvinyl ether with different molecular masses may be used.

The particle sizes of the dispersions should be between 50 and 500 nm, in particular between 50 and 200 nm. The particle size and the degree of crosslinking may be adjusted in a known manner as a function of the polymerization conditions and the comonomers. Smaller particle sizes and a higher degree of crosslinking may result in an increase of the release of active substance.

Matrix plasters may be produced in the usual manner by dissolving or finely dispersing the active substance in a suitable polymer solution and subsequently extracting this self-adhesive mass containing the active substance into a film by using roller or doctor blade deposition methods. In some cases it may be expedient to dissolve or extremely finely disperse the active substance prior to adding it to the polymer solution in an organic solvent such as for example ethanol or acetone. In this way, an improved distribution of the active substance in the polymer may be achieved.

The plasters may also be produced in accordance with German patent application no P 38 07 283.1 by working in the cooling mixture in a finely pulverized form, e.g. bound to a carrier (particle size lower than 200, in particular lower than 50 .mu.m) in the aqueous latex dispersion or by dispersing or dissolving it in an aqueous emulsifier solution and admixing this mixture to the aqueous latex dispersion at a temperature of 10 to 80, in particular of 30 to 70° C.

Expediently, the cooling mixture according to the invention is provided, the emulsifier and water are added and then mixed with the polymer dispersion. The cooling mixture thus obtained as a dispersion is, if required, provided with further auxiliary agents and is, as mentioned, extracted in a manner per se known into a film on a backing film and is dried. The drying temperature may here be between room temperature and 100.degree. C., with an optimum between the targeted rapid drying and ensuring that any blistering in the film and thermal loading of the active ingredient are avoided generally being in the order of 35 to 45° C.

This process has the significant advantage that the use of organic solvents is avoided. However, in principle also any other customary production methods for matrix plasters may be considered.

The resulting films have a thickness of 10 to 800, preferably 50 to 300 um. Film production may be carried out in a continuous or a batchwise process. The deposition process may be repeated several times, until the film has reached the desired thickness. The sticky polymer layer contains components a) and b) of the cooling mixture according to the invention in an accumulated concentration in the range of 1 to 40, in particular 5 to 25% by wt. in relation to the overall mass of the sticky polymer layer. The same concentration also applies to the reservoir liquid in the case of the membrane system (in relation to the overall mass of the reservoir liquid) and for the cooling mixture solution or dispersion used to impregnate the non-woven fabric or the porous polymer in the case of the non-woven system (in relation to the overall mass of the solution).

As emulsifiers both for the cooling mixture and also the polymers, the surfactants customarily used for this are used, such as the sodium salt of longer-chained fatty acids and the sulfuric acid semi-ester of a (if required oxyethylated) fatty alcohol as examples of anionic surfactants as well as polyethoxylated alkyl phenols and longer-chained fatty alcohols (e.g. hexadecan-(1)-ol) and glycerine partial fatty acid esters as examples of non-ionic surfactants and co-emulsifiers.

The desired viscosity of the mass ready to be extracted may be adjusted for example using polyacrylic acids or cellulose derivatives.

As additional crosslinkers which improve cohesion and thus the adhesive properties of the films, for example melamine formaldehyde resins may be used.

In order to enhance the release of the active substance, swelling agents such as polyvinyl pyrrolidone, cellulose derivatives or polyacrylates may be used, since the film can absorb more water, so that the diffusion resistance is reduced. The release of the active substances may be further improved by adding hydrophilic plasticizers such glycerine, 1,2-propanediol of the polyethylene glycols and lipophilic plasticizers such as triacetine, dibutyl phthalate or isopropyl myristate.

Matrix plasters usually provide a first order release of active substance. By using fillers which adsorb the active substance, such as aerosil, microcrystalline cellulose or lactose, an approximately zero order release will result.

The backing film which is dried onto the self-adhesive mass containing the cooling mixture is preferably essentially impermeable both to the active substance and to the water vapor. It may consist for example of an aluminum-plastic composite film, a metalized plastic film, a plastic film which, towards the side of the active substance, is provided with a barrier layer for example of polyvinylidene chloride, or of a simple plastic film, for example a polyester film.

The plasters according to the invention, which are designed according to the membrane system, are also manufactured in the usual manner (e.g. EP 0 186 071 A2, U.S. Pat. No. 4,262,003).

The production of the plasters designed according to the non-woven system is carried out by impregnating non-woven fabrics or porous polymers attached to the backing film with a solution or a dispersion of the cooling mixture in a hydrophilic or lipophilic solvent or solvent mix. Subsequently, the impermeable peel-off film is deposited.

Combination of Active Substances

If required, the cooling mixtures according to the invention may be combined with further known active substances, in particular with those that have a benefit effect in cosmetic or care compositions.

Anti-Irritants

Cosmetic/care compositions according to the invention may also contain anti-inflammatory active substances and/or active substances that alleviate reddening and/or itching. Here, any of the anti-inflammatory active substance and/or any of the active sub-stances for alleviating reddening and/or itching may be used that are suitable or customarily used for cosmetic and/or dermatological applications. Advantageously, steroidal anti-inflammatory active substances of the corticosteroide type are used as anti-inflammatory active substances or as active substances for alleviating reddening and/or itching, such as hydrocortisone, hydrocortisone derivatives such as hydrocortisone-17-butyrat, dexamethasone, dexamethasone phosphate, methylprednisolone or cortisone, and this list may be extended by adding further steroidal anti-inflammatory agents. Also non-steroidal anti-inflammatory agents may be used. Examples to be mentioned here include oxicams such as Piroxicam or Tenoxicam; salicylates such as Aspirin, Disalcid, Solprin or Fendosal; acetic acid derivatives such as Diclofenac, Fenclofenac, Indomethacin, Sulindac, Tolmetin or Clindanac; fenamates such as Mefenamic, Meclofenamic, Flufenamic or Niflumic; propionic acid derivatives such as Ibuprofen, Naproxen, Benoxaprofen, or pyrazols such as Phenylbutazon, Oxyphenylbutazon, Febrazon or Azapropazon. Alternatively, natural anti-inflammatory substances or substances for alleviating reddening and/or itching may be used. What can be used are plant extracts, special highly effective plant extract fractions as well as active substances of high purity isolated from plant extracts. Particularly preferred are extracts, fractions and active substances from camomile, Aloe vera, *Commiphora* species, *Rubia* species, willows, willow herbs, oats, Calendula, arnica, amber, honeysuckle, rosemary, melissa, ginger, Passiflora incarnata, Hamamelis, Pueraria, Dianthus or Echinacea as well as pure substances such as Bisabolol, Apigenin, Apigenin-7-glucosid, rosemarinic acid, boswellic acid, phytosterols, glycyrrhizic acid, Glabridin, Licochalkon A, gingerols and anthranilic acid amides such as in particular avenanthramides or dianthramides. The compositions according to the invention may also contain mixtures of two or more anti-inflammatory active substances.

The amount of anti-irritants (one or more compounds) in the compositions is preferably 0.0001 to 20% by wt., particularly preferably 0.0001-10% by wt., in particular 0.001-5% by wt, in relation to the overall weight of the composition.

Antiperspirants

In addition, also antiperspirant active substances (antiperspirants) may be used particularly advantageously with the compositions according to the invention. As antiperspirant active substances, predominantly aluminum salts such as aluminum chloride, aluminum chlorhydrate, nitrate, sulfate, acetate etc. are used. Moreover, however, also the use of zink, magnesium and zirconium compounds may be advantageous. For the application in cosmetic and dermatological antiperspirants, aluminum salts and—to a somewhat lower degree—aluminum/zirconium salt combinations have essentially proven successful. What is worth mentioning apart from that are the partially neutralized and thus more skin-compatible, although not quite so effective aluminum hydroxychlorides. Apart from aluminum salts, also other substances may be considered, such as for example a) protein precipitating substances such as formaldehyde, glutaraldehyde, natural and synthetic tannins as well as trichloroacetic acid which cause a superficial closure of the perspiratory glands, b) local anasthetics (e.g. diluted solutions of e.g. Lidokain, Prilokain or mixtures of such substances), which eliminate the sympathetic supply of the perspiratory glands by blocking the peripheral nerve tracts, c) zeoliths of type X, A or V, which besides reducing sweat secretion also have the function of adsorbing bad odors, and d) botulinus toxin (toxin of the bacteria Chlostridium botulinum) which is also used for the treatment of hyperhidrosis, an abnormally increased secretion of sweat, and the effect of which is based on an irreversible blockage of the release of the transmitter substance acetylchonine which is relevant for the secretion of sweat. Apart from that, also peptidic botulinus toxin analogs may be used in the compositions according to the invention.

Preferred sanitary articles in terms of the invention are wet wipes, sanitary towels, tampons and refreshing tissues containing a cooling mixture according to the invention. Of course, the cooling mixtures according to the invention may also be present in any of the preferred, above-described forms. Also, the sanitary articles according to the invention may contain cosmetic compositions according to the invention, in particular in the above-described preferred variants.

Methods

Further part of the invention is a method for generating an enhanced cooling effect of a cooling substance consisting of (i) 5-methyl-2-(propane-2-yl)cyclohexyl-N-ethyloxamate (formula I)

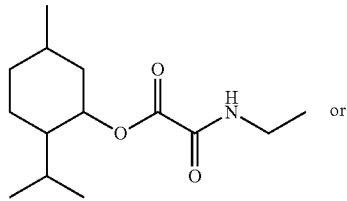 [SMILES: CCNC(=O)C(=O)OC1CC(C)CCC1C(C)C] or (ii) a physiologically cooling compound different to 5-methyl-2-(propane-2-yl)cyclohexyl-N-ethyloxamate or
(iii) a mixture of 2, 3, 4, 5, 6, 7, 8, 9, 10 or more physiologically cooling compounds different to 5-methyl-2-(propane-2-yl)cyclohexyl-N-ethyloxamate or
(iv) a mixture of one, 2, 3, 4, 5, 6, 7, 8, 9 or more physiologically cooling compounds with 5-methyl-2-(propane-2-yl)cyclohexyl-N-ethyloxamate on the skin or a mucous membrane, comprising the following steps:
(a) providing a cooling mixture according to the invention or a cosmetic composition according to the invention and
(b) contacting the cooling mixture or the cosmetic composition with skin or a mucous membrane.

What is preferred in this connection is the advantage of the method according to the invention is that the reduce amount of cooling substance can be used to achieve a given cooling sensation or an enhanced cooling effect an be achieved by using a given amount of cooling substance.

A further component of the invention is a method for producing a cooling mixture according to the invention or a cosmetic composition according to the invention or a sanitary article according to the invention, comprising the following steps:

(a) providing a cooling substance, the cooling substance consisting of
(i) 5-methyl-2-(propane-2-yl)cyclohexyl-N-ethyloxamate (formula I)

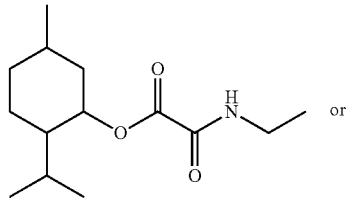 [SMILES: CCNC(=O)C(=O)OC1CC(C)CCC1C(C)C] or (ii) a physiologically cooling compound different to 5-methyl-2-(propane-2-yl)cyclohexyl-N-ethyloxamate or
(iii) a mixture of 2, 3, 4, 5, 6, 7, 8, 9, 10 or more physiologically cooling compounds different to 5-methyl-2-(propane-2-yl)cyclohexyl-N-ethyloxamate or
(iv) a mixture of one, 2, 3, 4, 5, 6, 7, 8, 9 or more physiologically cooling compounds with 5-methyl-2-(propane-2-yl)cyclohexyl-N-ethyloxamate
(b) providing one, two, three or more polyols selected from group A consisting of branched or unbranched alkanediols and branched or unbranched alkanetriols each having 3-12 carbon atoms, and
(c) mixing the components provided in steps a) and b).

This method according to the invention to generates the mixtures, cosmetic compositions or sanitary articles having the benefits of the present invention. Accordingly it is preferred that further compounds (especially compounds of any one, two, three, four or all of groups B-F) are added in the method according to the invention.

It is preferred that the uses and methods according to the invention are made for none-therapeutic purposes. Especially it is preferred that the uses and methods according to the invention are made for cosmetic or non-medical care purposes only.

EXAMPLES OF FORMULATIONS

All Amounts in w/w-%

Formulation Example 1A

Hair Lotion

| Phase | Amount | Ingredient |
|---|---|---|
| A | q.s. | Perfume oil |
|  | 1.00 | PEG-40 Hydrogenated Castor Oil |
| B | 65.0 | alcohol |
|  | 1.0 | Panthenol |
|  | 0.5 | Polyquarternium-16 |
|  | 0.1 | Menthol |
|  | 2.00 | (1R,2S,5R)-5-methyl-2-(propane-2-yl)cyclohexyl N ethyloxamate |
|  | 3.00 | Pentylene glycol |
|  | 27.4 | Aqua |

Preparation: mix phase A. Add phase B and stir until completely dissolved, adjust pH value to pH 7.0.

Formulation Example 1B

Hair Lotion

| Phase | Amount | Ingredient |
|---|---|---|
| A | q.s. | Perfume oil |
|  | 1.00 | PEG-40 Hydrogenated Castor Oil |
| B | 65.0 | Alcohol |
|  | 1.0 | Panthenol |
|  | 0.5 | Polyquarternium-16 |
|  | 0.1 | Menthol |
|  | 2.00 | (1R,2S,5R)-5-methyl-2-(propane-2-yl)cyclohexyl N ethyloxamate |
|  | 3.00 | Pentylene glycol |
|  | 1.00 | 4-t Butylcyclohexanol |
|  | 26.4 | Aqua dem. |

Preparation: Mix Phase A. Add phase B and stir until completely dissolved, adjust pH value to pH 7.0.

Formulation Example 2A

Hair Gel

| Phase | Amount | Ingredient |
|---|---|---|
| A | 45.00 | Carbopol 940 1% in water |
|  | 0.70 | Aminomethyl Propanol |
| B | 7.50 | VP/MethacrylamideNinyl Imidazole Copolymer |
|  | 0.10 | Perfume oil |
|  | 0.30 | PEG-40 Hydrogenated Castor Oil |
|  | 0.30 | Preservative |
|  | 0.05 | Disodium EDTA |
|  | 0.30 | Panthenol |
|  | 8.00 | Alcohol |
|  | 5.00 | Pentylene glycol |
|  | 2.00 | (1R,2S,5R)-5-methyl-2-(propane-2-yl)cyclohexyl N ethyloxamate |
|  | 30.75 | Aqua dem. |

Preparation: Mix Phase A. Add phase B and stir until completely dissolved, adjust pH value to pH 7.0.

Formulation Example 2B

Hair Gel

| Phase | Amount | Ingredient |
|---|---|---|
| A | 45.00 | Carbopol 940 1% in water |
|  | 0.70 | Aminomethyl Propanol |
| B | 7.50 | VP/MethacrylamideNinyl Imidazole Copolymer |
|  | 0.10 | Perfume oil |
|  | 0.30 | PEG-40 Hydrogenated Castor Oil |
|  | 0.30 | Preservative |
|  | 0.05 | Disodium EDTA |
|  | 0.30 | Panthenol |
|  | 8.00 | Alcohol |
|  | 5.00 | Pentylene glycol |
|  | 0.5 | 4-t Butylcyclohexanol |
|  | 1.50 | (1R,2S,5R)-5-methyl-2-(propane-2-yl)cyclohexyl-N-ethyloxamate |
|  | 30.75 | Aqua dem. |

Preparation: Mix Phase A. Add phase B and stir until completely dissolved, adjust pH value to pH 7.0.

Formulation Example 3A

Cosmetric Sun Protection Composition

In the following recipes, a cosmetic sun protection composition is described that contains a combination of at least a non-organic pigment and an organic UV filter. The formulations listed below are prepared in the usual manner as known to a person skilled in the art.

| Phase | Amount | Ingredient |
|---|---|---|
| A | 7.50 | Ethylhexyl cinnamic acid |
|  | 2.00 | Benzophenon-3 |
|  | 0.80 | Polyglyceryl dimer soyate |
|  | 1.00 | Sorbitane stearate |
|  | 0.50 | Tocopheryl acetate |
|  | 3.00 | Glyceryl stearate, PEG-100 Stearate |
|  | 1.00 | PEG-40 hydrogenated castor oil |
| B | 3.00 | Titanium dioxide, aluminum oxide hydrate, Dimethicon/Methicon Copolymer |
|  | 1.00 | *Butyrospermum parkii* (Shea Butter) |
|  | 6.50 | C12-1s alkyl benzoate |
| C | 5.00 | Butylene glycol |
|  | 0.30 | Xanthan gum |
|  | 0.10 | Disodium EDTA |
|  | 0.10 | Allantoin |
| D | 1.00 | Polyacryl amide, C13_14 isoparaffin, Laureth-7 |
|  | 5.00 | Pentylene glycol |
|  | 2.00 | (1R,2S,5R)-5-methyl-2-(propane-2-yl)cyclohexyl N ethyloxamate |
|  | 59.20 | Aqua dem. |

Formulation Example 3B

Cosmetic Sun Protection Composition

| Phase | Amount | Ingredient |
|---|---|---|
| A | 7.50 | Ethylhexyl cinnamic add |
|   | 2.00 | Benzophenon-3 |
|   | 0.80 | Polyglyceryl dimer soyate |
|   | 1.00 | Sorbitane stearate |
|   | 0.50 | Tocopheryl acetate |
|   | 3.00 | Glyceryl stearate, PEG-100 Stearate |
|   | 1.00 | PEG-40 hydrogenated castor oil |
| B | 3.00 | Titanium dioxide, aluminum oxide hydrate, Dimethicon/Methicon Copolymer |
|   | 1.00 | *Butyrospermum parkii* (Shea Butter) |
|   | 6.50 | C12-1s alkyl benzoate |
| C | 5.00 | Butylene glycol |
|   | 0.30 | Xanthan gum |
|   | 0.10 | Disodium EDTA |
|   | 0.10 | Allantoin |
| D | 1.00 | Polyacryl amide, C13_14 isoparaffin, Laureth-7 |
|   | 5.00 | Pentylene glycol |
|   | 1.00 | 4-t Butylcyclohexanol |
|   | 2.00 | (1R,2S,5R)-5-methyl-2-(propane-2-yl)cyclohexyl-N-ethyloxamate |
|   | 60.20 | Aqua dem. |

Formulation Example 4A

Moisturizing Body Care Cream

| Phase | Amount | Ingredient |
|---|---|---|
| A | 6.0 | PEG-7 hydrogenated castor oil |
|   | 10.0 | Cetearyl ethyl hexanoate |
|   | 5.0 | Isopropyl myristate |
|   | 7.0 | Mineral oil |
|   | 0.5 | Shea Butter (*Butyrospermum parkii*) |
|   | 0.5 | Aluminum stearate |
|   | 0.5 | Magnesium stearate |
|   | 0.2 | Bisabolol |
|   | 0.7 | Quaternium-18-Hectorit |
| B | 5.0 | Dipropylene glycol |
|   | 0.7 | Magnesium sulfate |
|   | q.s. | Preservative |
|   | q.s. | Perfume oil |
|   | 4.00 | Pentylene glycol |
|   | 1.00 | (1R,2S,5R)-5-methyl-2-(propane-2-yl)cyclohexyl Nethyloxamate |
|   | 58.9 | Aqua dem. |

Preparation: Heat phases A and B separately to approx. 80° C. Mix phase B in with phase A and homogenize. Cool down to approx. 40° C. under stirring. Add phase C and homogenize again. Allow to cool down to room temperature under stirring.

Formulation Example 4B

Moisturizing Body Care Cream

| Phase | Amount | Ingredient |
|---|---|---|
| A | 6.0 | PEG-7 hydrogenated castor oil |
|   | 10.0 | Cetearyl ethyl hexanoate |
|   | 5.0 | Isopropyl myristate |
|   | 7.0 | Mineral oil |
|   | 0.5 | Shea Butter (*Butyrospermum parkii*) |
|   | 0.5 | Aluminum stearate |
|   | 0.5 | Magnesium stearate |
|   | 0.2 | Bisabolol |
|   | 0.7 | Quaternium-18-Hectorit |
| B | 5.0 | Dipropylene glycol |
|   | 0.7 | Magnesium sulfate |
|   | q.s. | Preservative |
|   | q.s. | Perfume oil |
|   | 4.00 | Pentylene glycol |
|   | 1.00 | (1R,2S,5R)-5-methyl-2-(propane-2-yl)cyclohexyl N-ethyloxamate |
|   | 0.50 | 4-t Butylcyclohexanol |
|   | 58.4 | Aqua dem. |

Preparation: Heat phases A and B separately to approx. 80° C. Mix phase B in with phase A and homogenize. Cool down to approx. 40° C. under stirring. Add phase C and homogenize again. Allow to cool down to room temperature under stirring.

Formulation Example 5A

Care Shampoo

| Phase | Amount | Ingredient |
|---|---|---|
| A | 30.0 | Sodium laureth sulfate |
|   | 6.0 | Sodium cocoamphoacetate |
|   | 6.0 | Cocamidopropyl betaine |
|   | 3.0 | Sodium laureth sulfate, glycol distearate, Cocamid MEA, Laureth-10 |
|   | 7.2 | Polyquaternium-44 |
|   | 2.0 | Amodimethicon |
|   | q.s. | Perfume oil |
|   | 1.0 | Sodium chloride |
| B | 3.00 | Pentylene glycol |
|   | 1.5 | (1R,2S,5R)-5-methyl-2-(propane-2-yl)cyclohexyl N ethyloxamate |
|   | 40.3 | Aqua dem. |

Preparation: Mix and dissolve the components of phase A. Adjust pH value to 6-7 using citric acid.

Formulation Example 5B

Care Shampoo

| Phase | Amount | Ingredient |
|---|---|---|
| A | 30.0 | Sodium laureth sulfate |
|   | 6.0 | Sodium cocoamphoacetate |
|   | 6.0 | Cocamidopropyl betaine |
|   | 3.0 | Sodium laureth sulfate, glycol distearate, cocamid MEA, Laureth-10 |
|   | 7.2 | Polyquaternium-44 |
|   | 2.0 | Amodimethicon |
|   | q.s. | Perfume oil |
|   | 1.0 | Sodium chloride |
| B | 2.50 | Pentylene glycol |
|   | 1.5 | (1R,2S,5R)-5-methyl-2-(propane-2-yl)cyclohexyl N ethyloxamate |
|   | 0.5 | 4-t Butylcyclohexanol |
|   | 40.3 | Aqua dem. |

Preparation: Mix and dissolve the components of phase A. Adjust pH value to 6-7 using citric acid.

Formulation Example 6A

Shower Gel

| Phase | Amount | Ingredient |
|---|---|---|
| A | 40.0 | Sodium laureth sulfate |
|   | 5.0 | Decyl glucoside |
|   | 5.0 | Cocamidopropyl betaine |
|   | 1.0 | (1R,2S,5R)-5-methyl-2-(propane-2-yl)cyclohexyl N ethyloxamate |
|   | 1.0 | Panthenol |
|   | q.s. | Perfume oil |
|   | 3.0 | Pentylene glycol |
|   | 2.0 | Sodium chloride |
|   | 43.0 | Aqua dem. |
| B | q.s. | Citric acid |

Preparation: Mix and dissolve the components of phase A. Adjust pH value to 6-7 using citric acid.

Formulation Example 6B

Shower Gel

| Phase | Amount | Ingredient |
|---|---|---|
| A | 40.0 | Sodium laureth sulfate |
|   | 5.0 | Decyl glucoside |
|   | 5.0 | Cocamidopropyl betaine |
|   | 1.0 | (1R,2S,5R)-5-methyl-2-(propane-2-yl)cyclohexyl N ethyloxamate |
|   | 1.0 | Panthenol |
|   | q.s. | Perfume oil |
|   | 3.0 | Pentylene glycol |
|   | 2.0 | Sodium chloride |
|   | 42.6 | Aqua dem. |
|   | 0.4 | 4-t Butylcyclohexanol |
| B | q.s. | Citric acid |

Preparation: Mix and dissolve the components of phase A. Adjust pH value to 6-7 using citric acid.

Formulation Example 7A

Shampoo

| Phase | Amount | Ingredient |
|---|---|---|
| A | 40.0 | Sodium laureth sulfate |
|   | 5.0 | Sodium C12-1s pareth-15 sulfonate |
|   | 5.0 | Decyl glucoside |
|   | q.s. | Perfume oil |
|   | 0.1 | Phytantriol |
|   | 40.6 | Aqua dem. |
|   | 0.5 | (1R,2S,5R)-5-methyl-2-(propane-2-yl)cyclohexyl N ethyloxamate |
|   | 0.3 | Polyquaternium-10 |
|   | 1.0 | Panthenol |
|   | q.s. | Preservative |
|   | 4.5 | Pentylene glycol |
|   | 1.0 | Laureth-3 |
|   | 2.0 | Sodium chloride |

Preparation: Mix and dissolve the components of phase A. Adjust pH value to 6-7 using citric acid.

Formulation Example 7B

Shampoo

| Phase | Amount | Ingredient |
|---|---|---|
| A | 40.0 | Sodium laureth sulfate |
|   | 5.0 | Sodium C12-14 Pareth-15 sulfonate |
|   | 5.0 | Decyl glucoside |
|   | q.s. | Perfume oil |
|   | 0.1 | Phytantriol |
|   | 40.3 | Aqua dem. |
|   | 0.5 | (1R,2S,5R)-5-methyl-2-(propane-2-yl)cyclohexyl N ethyloxamate |
|   | 0.3 | Polyquaternium-10 |
|   | 1.0 | Panthenol |
|   | q.s. | Preservative |
|   | 4.5 | Pentylene glycol |
|   | 1.0 | Laureth-3 |
|   | 0.3 | 4-t Butylcyclohexanol |
|   | 2.0 | Sodium chloride |

Preparation: Mix and dissolve the components of phase A. Adjust pH value to 6-7 using citric acid.

Formulation Example 8A

Foot Balm

| Phase | Amount | Ingredient |
|---|---|---|
| A | 2.0 | Ceteareth-6, Stearyl alcohol |
|   | 2.0 | Ceteareth-25 |
|   | 5.0 | Cetearyl ethyl hexanoate |
|   | 4.0 | Cetyl alcohol |
|   | 4.0 | Glyceryl stearate |
|   | 5.0 | Mineral oil |
|   | 0.2 | Menthol |
|   | 0.5 | Camphor |
| B | 65.3 | Aqua dem. |
|   | q.s. | Preservative |
| C | 1.0 | Bisabolol |
|   | 1.0 | Tocopheryl acetate |
| D | 0.5 | (1R,2S,5R)-5-methyl-2-(propane-2-yl)cyclohexyl N ethyloxamate |
|   | 4.5 | Pentylene glycol |
|   | 5.0 | Witch hazel extract |

Preparation: Heat the components of phases A and B separately to approx. 80° C. Mix phase B in with phase A whilst homogenizing. Cool down to approx. 40° C. under stirring, add phases C and D and re-homogenize for a short time. Cool down to room temperature under stirring.

Formulation Example 8B

Foot Balm

| Phase | Amount | Ingredient |
|---|---|---|
| A | 2.0 | Ceteareth-6, Stearyl alcohol |
|   | 2.0 | Ceteareth-25 |
|   | 5.0 | Cetearyl ethyl hexanoate |
|   | 4.0 | Cetyl alcohol |
|   | 4.0 | Glyceryl stearate |
|   | 5.0 | Mineral oil |
|   | 0.2 | Menthol |
|   | 0.5 | Camphor |
| B | 65.3 | Aqua dem. |
|   | q.s. | Preservative |
| C | 1.0 | Bisabolol |
|   | 1.0 | Tocopheryl acetate |

-continued

| Phase | Amount | Ingredient |
|---|---|---|
| D | 0.5 | (1R,2S,5R)-5-methyl-2-(propane-2-yl)cyclohexyl N ethyloxamate |
| | 4.5 | Pentylene glycol |
| | 0.3 | 4-t Butylcyclohexanol |
| | 4.7 | Witch hazel extract |

Preparation: Heat the components of phases A and B separately to approx. 80° C. Mix phase B in with phase A whilst homogenizing. Cool down to approx. 40° C. under stirring, add phases C and D and re-homogenize for a short time. Cool down to room temperature under stirring.

Formulation Example 9A

Face Cleansing O/W Lotion

| Phase | Amount | Ingredient |
|---|---|---|
| A | 10.0 | Cetearyl ethyl hexanoate |
| | 10.0 | Caprylic/capric triglyceride |
| | 1.5 | Cyclopentasiloxane, Cyclohexasiloxane |
| | 2.0 | PEG-40 hydrogenated castor oil |
| B | 3.5 | Caprylic/capric triglyceride, sodium acrylate copolymer |
| C | 1.0 | Tocopheryl acetate |
| | 0.2 | Bisabolol |
| | q.s. | Preservative |
| | q.s. | Perfume oil |
| D | 3.0 | Polyquaternium-44 |
| | 0.5 | Cocotrimonium methosulfate |
| | 0.5 | Ceteareth-25 |
| | 2.0 | Panthenol, Propylene glycol |
| | 4.0 | Pentylene glycol |
| | 0.1 | Disodium EDTA |
| | 1.0 | (1R,2S,5R)-5-methyl-2-propane-2-yl)cyclohexyl N ethyloxamate |
| | 60.7 | Aqua dem. |

Preparation: Dissolve phase A. Mix phase B in with phase A, work phase C into combined phases A and B. Dissolve phase D, mix into combined phases A, B and C and homogenize. Keep stirring for another 15 min.

Formulation Example 9B

Face Cleansing O/W Lotion

| Phase | Amount | Ingredient |
|---|---|---|
| A | 10.0 | Cetearyl ethyl hexanoate |
| | 10.0 | Caprylic/capric triglyceride |
| | 1.5 | Cyclopentasiloxane, Cyclohexasiloxane |
| | 2.0 | PEG-40 hydrogenated castor oil |
| B | 3.5 | Caprylic/capric triglyceride, sodium acrylate copolymer |
| C | 1.0 | Tocopheryl acetate |
| | 0.2 | Bisabolol |
| | q.s. | Preservative |
| | q.s. | Perfume oil |
| D | 3.0 | Polyquaternium-44 |
| | 0.5 | Cocotrimonium methosulfate |
| | 0.5 | Ceteareth-25 |
| | 2.0 | Panthenol, Propylene glycol |
| | 4.0 | Pentylene glycol |
| | 0.1 | Disodium EDTA |
| | 1.0 | (1R,2S,5R)-5-methyl-2-propane-2-yl)cyclohexyl N ethyloxamate |
| | 1.0 | 4-t-Butylcyclohexanol |
| | 59.7 | Aqua dem. |

Preparation: Dissolve phase A. Mix phase B in with phase A, work phase C into combined phases A and B. Dissolve phase D, mix into combined phases A, B and C and homogenize. Keep stirring for another 15 min.

Formulation Example 10A

Body Spray

| Phase | Amount | Ingredient |
|---|---|---|
| A | 3.0 | Ethyl hexyl methoxy cinnamate |
| | 2.0 | Diethylamino hydroxybenzoyl hexyl benzoate |
| | 1.0 | Polyquaternium-44 |
| | 3.0 | Pentylene glycol |
| | 2.0 | Panthenol, Propylene glycol |
| | 1.0 | Cyclopentasiloxane, Cyclohexasiloxane |
| | 10.0 | Octyldodecanol |
| | 0.5 | PVP |
| | 10.0 | Caprylic/capric triglyceride |
| | 3.0 | C12-1s alkyl benzoate |
| | 3.0 | Glycerine |
| | 1.0 | Tocopheryl acetate |
| | 0.3 | Bisabolol |
| | 0.5 | (1R,2S,5R)-5-methyl-2-(propane-2-yl)cyclohexyl N ethyloxamate |
| | 59.7 | Alcohol |

Preparation: Weigh the components of phase A and dissolve clearly.

Formulation Example 10B

Body Spray

| Phase | Amount | Ingredient |
|---|---|---|
| A | 3.0 | Ethyl hexyl methoxy cinnamate |
| | 2.0 | Diethylamino hydroxybenzoyl hexyl benzoate |
| | 1.0 | Polyquaternium-44 |
| | 3.0 | Pentylene glycol |
| | 2.0 | Panthenol, Propylene glycol |
| | 1.0 | Cyclopentasiloxane, Cyclohexasiloxane |
| | 10.0 | Octyldodecanol |
| | 0.5 | PVP |
| | 10.0 | Caprylic/capric triglyceride |
| | 3.0 | C12-14 alkyl benzoate |
| | 3.0 | Glycerine |
| | 1.0 | Tocopheryl acetate |
| | 0.3 | Bisabolol |
| | 0.5 | (1R,2S,5R)-5-methyl-2-(propane-2-yl)cyclohexyl N ethyloxamate |
| | 0.5 | 4-t-Butylcyclohexanol |
| | 59.2 | Alcohol |

Preparation: Weigh the components of phase A and dissolve clearly.

Formulation Example 11A

Skin Care Gel

| Phase | Amount | Ingredient |
|---|---|---|
| A | 3.6 | PEG-40 hydrogenated castor oil |
| | 15.0 | Alcohol |
| | 0.1 | Bisabolol |
| | 0.5 | Tocopheryl acetate |
| | q.s. | Perfume oil |
| B | 3.0 | Panthenol |
| | 0.6 | Carbomer |
| | 4.0 | Pentylene glycol |
| | 0.5 | (1R,2S,5R)-5-methyl-2-(propane-2-yl)cyclohexyl N ethyloxamate |

| Phase | Amount | Ingredient |
|---|---|---|
| C | 71.9 | Aqua dem. |
| | 0.8 | Triethanolamine |
| | 0.1 | Bisabolol |
| | 0.5 | Tocopheryl acetate |
| | q.s. | Perfume oil |

Formulation Example 11B

Skin Care Gel

| Phase | Amount | Ingredient |
|---|---|---|
| A | 3.6 | PEG-40 hydrogenated castor oil |
| | 15.0 | Alcohol |
| | 0.1 | Bisabolol |
| | 0.5 | Tocopheryl acetate |
| | q.s. | Perfume oil |
| B | 3.0 | Panthenol |
| | 0.6 | Carbomer |
| | 4.0 | Pentylene glycol |
| | 0.5 | (1R,2S,5R)-5-methyl-2-(propane-2-yl)cyclohexyl N ethyloxamate |
| | 71.7 | Aqua dem. |
| | 0.2 | 4-t Butylcyclohexanol |
| C | 0.8 | Triethanolamine |

Formulation Example 12A

After Shave Lotion

| Phase | Amount | Ingredient |
|---|---|---|
| A | 10.0 | Cetearyl ethyl hexanoate |
| | 5.0 | Tocopheryl acetate |
| | 1.0 | Bisabolol |
| | 0.1 | Perfume oil |
| | 0.3 | Acrylate/$C_{10-30}$ alkylacrylate crosspolymer |
| B | 15.0 | Alcohol |
| | 1.0 | Panthenol |
| | 3.0 | Glycerine |
| | 1.0 | (1R,2S,5R)-5-methyl-2-(propane-2-yl)cyclohexyl N ethyloxamate |
| | 4.0 | Pentylene glycol |
| | 0.1 | Triethanolamine |
| | 59.5 | Aqua dem. |

Preparation: Mix the components of phase A. Dissolve phase B, work into phase A and homogenize.

Formulation Example 12B

After Shave Lotion

| Phase | Amount | Ingredient |
|---|---|---|
| A | 10.0 | Cetearyl ethyl hexanoate |
| | 5.0 | Tocopheryl acetate |
| | 1.0 | Bisabolol |
| | 0.1 | Perfume oil |
| | 0.3 | Acrylate/$C_{10-30}$ alkylacrylate crosspolymer |
| B | 15.0 | Alcohol |
| | 1.0 | Panthenol |
| | 3.0 | Glycerine |
| | 1.0 | (1R,2S,5R)-5-methyl-2-(propane-2-yl)cyclohexyl N ethyloxamate |
| | 4.0 | Pentylene glycol |
| | 0.1 | Triethanolamine |
| | 0.6 | 4-t-Butylcyclohexanol |
| | 58.9 | Aqua dem. |

Preparation: Mix the components of phase A. Dissolve phase B, work into phase A and homogenize.

Formulation Example 13A

After Sun Lotion

| Phase | Amount | Ingredient |
|---|---|---|
| A | 0.4 | Acrylate/C10-30 alkylacrylate crosspolymer |
| | 15.0 | Cetearylethyl hexanoate |
| | 0.2 | Bisabolol |
| | 1.0 | Tocopheryl acetate |
| | q.s. | Perfume oil |
| B | 1.0 | Panthenol |
| | 15.0 | Alcohol |
| | 3.0 | Glycerine |
| | 1.5 | (1R,2S,5R)-5-methyl-2-(propane-2-yl)cyclohexyl N ethyloxamate |
| | 4.0 | Pentylene glycol |
| | 58.7 | Aqua dem. |
| C | 0.2 | Triethanolamine |

Preparation: Mix the components of phase A. Mix phase B into phase A under homogenization. Neutralize with phase C and homogenize again.

Formulation Example 13B

After Sun Lotion

| Phase | Amount | Ingredient |
|---|---|---|
| A | 0.4 | Acrylate/C10-30 alkylacrylate crosspolymer |
| | 15.0 | Cetearylethyl hexanoate |
| | 0.2 | Bisabolol |
| | 1.0 | Tocopheryl acetate |
| | q.s. | Perfume oil |
| B | 1.0 | Panthenol |
| | 15.0 | Alcohol |
| | 3.0 | Glycerine |
| | 1.5 | (1R,2S,5R)-5-methyl-2-(propane-2-yl)cyclohexyl N ethyloxamate |
| | 4.0 | Pentylene glycol |
| | 2.0 | 4-t-Butylcyclohexanol |
| | 56.7 | Aqua dem. |
| C | 0.2 | Triethanolamine |

Preparation: Mix the components of phase A. Mix phase B into phase A under homogenization. Neutralize with phase C and homogenize again.

Formulation Example 14 A

Sun Lotion

| Phase | Amount | Ingredient |
|---|---|---|
| A | 4.5 | Ethyl hexyl methoxy cinnamic acid |
| | 2.0 | Diethylamino hydroxybenzoyl hexyl benzoate |
| | 3.0 | Octocrylene |
| | 2.5 | Di-C12-13 alkylmalate |

-continued

| Phase | Amount | Ingredient |
|---|---|---|
|  | 0.5 | Tocopheryl acetate |
|  | 4.0 | Polyglyceryl-3-methyl glucose distearate |
| B | 3.5 | Cetearyl isononanoate |
|  | 1.0 | VP/Eicosene copolymer |
|  | 5.0 | Isohexadecane |
|  | 2.5 | Di-C12-13 alkylmalate |
|  | 3.0 | Titanium dioxide, Trimethoxy caprylyl silane |
| C | 5.0 | Glycerine |
|  | 1.0 | Sodium cetearyl sulfate |
|  | 0.5 | Xanthan gum |
|  | 55.7 | Aqua dem. |
| D | 1.0 | (1R,2S,5R)-5-methyl-2-propane-2-yl)cyclohexyl N ethyloxamate |
|  | 4.0 | Pentylene glycol |
|  | 1.0 | Phenoxy ethanol, methyl paraben, ethyl paraben, butyl paraben, propyl paraben, isobutyl paraben |
|  | 0.3 | Bisabolol |

Preparation: Heat the components of phases A and B separately to approx. 80° C. Mix phase B in with phase A and homogenize. Heat phase C to approx. 80° C. into combined phases A and B under homogenization. Cool down to approx. 40° C. under stirring, add phase D and homogenize again.

Formulation Example 14B

Sun Lotion

| Phase | Amount | Ingredient |
|---|---|---|
| A | 4.5 | Ethyl hexyl methoxy cinnamic acid |
|  | 2.0 | Diethylamino hydroxybenzoyl hexyl benzoate |
|  | 3.0 | Octocrylene |
|  | 2.5 | Di-C12-13 alkylmalate |
|  | 0.5 | Tocopheryl acetate |
|  | 4.0 | Polyglyceryl-3-methyl glucose distearate |
| B | 3.5 | Cetearyl isononanoate |
|  | 1.0 | VP/Eicosene copolymer |
|  | 5.0 | Isohexadecane |
|  | 2.5 | Di-C12-13 alkyl malate |
|  | 3.0 | Titanium dioxide, trimethoxy caprylyl silane |
| C | 5.0 | Glycerine |
|  | 1.0 | Sodium cetearyl sulfate |
|  | 0.5 | Xanthan gum |
|  | 55.4 | Aqua dem. |
| D | 1.0 | (1R,2S,5R)-5-methyl-2-(propane-2-yl)cyclohexyl N ethyloxamate |
|  | 4.0 | Pentylene glycol |
|  | 0.3 | 4-t-Butylcyclohexanol |
|  | 1.0 | Phenoxy ethanol, methyl paraben, ethyl paraben, butyl paraben, propyl paraben, isobutyl paraben |
|  | 0.3 | Bisabolol |

Preparation: Heat the components of phases A and B separately to approx. 80° C. Mix phase B in with phase A and homogenize. Heat phase C to approx. 80° C. into combined phases A and B under homogenization. Cool down to approx. 40° C. under stirring, add phase D and homogenize again.

The following examples illustrate possibilities for using the cooling substances to according to the invention in cosmetic formulations, by the use of which a particularly pleasant cool feel on the skin and a balming of the skin may be achieved.

ADDITIONAL FORMULATION EXAMPLES

| Ingredient | INCI-Name | 15 | 16 | 17 | 18 | 19 | 20 | 21 | 22 | 23 | 24 | 25 | 26 | 27 |
|---|---|---|---|---|---|---|---|---|---|---|---|---|---|---|
| (1R,2S,5R)-5-methyl-2-(propane-2-yl)cyclohexyl N ethyloxamate | | 0.5 | 0.5 | 0.5 | 0.5 | 0.5 | 0.5 | 0.5 | 0.5 | 0.5 | 0.5 | 0.5 | 0.5 | 0.5 |
| SymSitive 1609 | Trans-4-tert. butyl cyclohexanol Pentylene Glycol | 1 | 1 | 1 | 1 | 1 | 1 | 1 | 1 | 1 | 1 | 1 | 1 | 1 |
| Allantoin | Allantoin | | | | 0.1 | | | | | | 0.1 | | | |
| (−) alpha Bisabolol natural | Bisabolol | 0.1 | | | | | | | | | 0.2 | | 0.3 | |
| Abil 350 | Dimethicone | | | 3.0 | | | | | | 2.0 | | | | |
| Akyposoft 100 BVC | Sodium Laureth-11 Carboxylate. Laureth-10 | | 8.5 | | | | | | | | | | | |
| Aloe Vera Gel Konzentrat 10:1 | Aloe Barbadensis Leaf juice | | | | | | 1.0 | | | | | | | |
| Aluminum stearate | Aluminum Stearate | | | | | | | | | | | | | 1.2 |
| Arlypon F | Laureth-2 | | 2.5 | | | | | | | | | | | |
| Biotive ® L-Arginine | Arginine | | | | | | | | | | 0.5 | | | |
| Carbopol Ultrez-10 | Carbomer | | | | | | | | | 0.2 | | 0.2 | | |
| Carbopol Ultrez-21 | Acrylates/Cl 0-30 Alkylacrylate Crosspolymer | | | | 0.4 | | | | | | | | | |
| Covi-Ox T-70 | Tocopherol | | | | 0.1 | | | | | | | 0.1 | | |
| CutinaGMS V | Glyceryl Stearate | | | | | | | | | | 2.0 | 2.0 | | |
| Dehyton K | Cocoamido propyl Betaine | | 7.0 | | | | | | | | | | | |
| Dehyquart A CA | Cetrimonium Choride | | | | | | | | | | | | | 4.0 |
| Deolite | Dimethyl Phenylpropanol Pentylene Glycol | | | | | | 0.5 | 0.5 | | | | | | |

| Ingredient | INCI-Name | 15 | 16 | 17 | 18 | 19 | 20 | 21 | 22 | 23 | 24 | 25 | 26 | 27 |
|---|---|---|---|---|---|---|---|---|---|---|---|---|---|---|
| Dow Corning 246 fluid | Cyclohexasiloxane | | | | | | | 1.0 | | | | 2.0 | | |
| D-Panthenol 75 L | Panthenol | | | 1.0 | | | | | | | | 1.0 | | 1.0 |
| Dracorin ® 100 S.E.P. | Glyceryl Stearate PEG-100 Stearate | | | | | | | 0.5 | | | | | | |
| Dracorin ® CE | Glyceryl Stearate/Citrate | | | | | | | | | | 2.0 | | | |
| Dracorin ® GOC | Glyceryl Oleate Citrate Caprylic Capric Triglyceride | | | | | | | 2.0 | | | | 2.0 | | |
| Drago-Beta-Glucan | Water (Aqua). Butylene Glycol. Glycerin. *Avena Sativa* (Oat) Kernel Extract | | | | | | | | | | 2.0 | | | |
| DragoCalm ® | Water. Glycerin. *Avena Sativa* (Oat Kernel Extract) | | | | | | | | | | 1.0 | | | |
| Dragocide ® Liquid | Phenoxy ethanol Methyl paraben Ethyl paraben Butyl paraben Propyl paraben Isobutyl paraben | | 0.5 | 0.8 | | | | 0.8 | 0.8 | | | | 0.8 | 0.8 |
| Dragoderm ® | Glycerin. *Triticum Vulgare* (Wheat) Gluten. Water (Aqua) | | | | | | | | | | 2.0 | 2.0 | | 2.0 |
| Dragosan W/0 P | Sorbitan Isostearate Hydrogenated Castor Oil. Ceresin. Beeswax (*Cera Alba*) | | | | | | | | | | | 8.0 | | |
| Dragosantol ® 100 | Bisabolol | | | 0.2 | | 0.2 | | 0.2 | | | 0.2 | | | |
| Dragosine ® | Carnosine | | | | | | | | | | | 1.0 | | |
| Dragoxat ® 89 | Ethylhexyl Isononanoate | | | | | | 1.0 | | | 3.0 | 4.0 | 1.0 | 5.0 | |
| EDTABD | Disodium EDTA | | | 0.1 | | | | | | 0.1 | 0.1 | | | |
| Emulsiphos ® | Potassium Cetyl Phosphate Hydrogenated Palm Glycerides | | | | | | | | 2.0 | | 2.0 | | | |
| Ethanol 96% | Ethanol | 26 | | | 81.0 | 45.0 | | | | | | 65.0 | | |
| Extrapone ® *Ginkgo Biloba* | Propylene Glycol. Water (Aqua). *Ginkgo Biloba* Leaf Extract. Glucose. Lactic Acid | | 1.0 | | | | | | | | | | | |
| Farnesol | Farnesol | | | | | 0.5 | | | | | | | | |
| Riechstoff | Perfume | 1.0 | 1.5 | 1.0 | 10.0 | 0.5 | 0.5 | 0.4 | 0.3 | 0.4 | 0.3 | 1.0 | 0.3 | 0.3 |
| Frescolat ® MGA | Menthone Glycerin Acetal | | | | | | 1.0 | | | | | | | |
| Frescolat ® ML | Menthyl Lactate | | | 0.6 | 1.0 | | 0.3 | | 0.5 | 0.3 | | 0.5 | | |
| Fruitapone ® Orange B | Propylene Glycol. Water (Aqua)./ Citric Acid. *Citrus Aurantium Dulcis* (Orange) Juice Trideceth-9. Bisabolol | | | | | | | | | 1.0 | | | | |
| Genapol LRO Liquid | Sodium Laureth Sulfate | | 40.0 | | | | | | | | | | | |
| Glycerin 99.5% | Glycerin | | | 2.5 | | | | 4.0 | 2.0 | | 3.0 | 4.0 | 3.0 | |
| Hydrolite ®-5 | Pentylene Glycol | | | | | | | | | 5.0 | | 5.0 | | |
| Hydroviton ®-24 | Water. Pentylene Glycol. Glycerin. Lactic Acid. Sodium Lactate. Serine. Urea. Sorbitol. Sodium Chloride. Allantoin | | | | | | | | | | 1.0 | | 2.0 | |
| Iso Adipat | Diisopropyl Adipate | | | | | | | | | | | 1.0 | 5.0 | |

-continued

| Ingredient | INCI-Name | % w/w Formulation example | | | | | | | | | | | |
|---|---|---|---|---|---|---|---|---|---|---|---|---|---|
| | | 15 | 16 | 17 | 18 | 19 | 20 | 21 | 22 | 23 | 24 | 25 | 26 | 27 |
| Isodragol ® | Triisononanoin | | | | | | | 1.0 | | | | | | |
| Jojobaöl | Simmondsia Chinensis (Jojoba) Seed Oil | | | 2.0 | | | | | | | | | 2.0 | |
| Keltrol CG RD | XanthanGum | | | | | | | | 0.1 | 0.1 | 0.2 | | | |
| Lanette 0 | Cetearyl Alcohol | | | | | | | | 3.0 | 2.0 | 3.0 | | | 3.5 |
| Mineral oil | Mineral Oil | | | | | | | | | | | | 8.0 | |
| Sodium chloride | Sodium Chloride | | | | | | | | | | | | 1.0 | 2.0 |
| Sodium hydroxide 10% Lsg. | Sodium Hydroxide | | 0.1 | 0.8 | | | | 0.6 | 0.5 | | | 0.4 | | |
| Sodium stearate | Sodium Stearate | | | | | | 9.0 | | | | | | | |
| Neo Heliopan ® 303 | Octocrylene | | | | | | | | 5.0 | 8.0 | | | | |
| Neo Heliopan ® 357 | Butylmethoxy dibenzoyl methane | | | | | | | | 1.1 | 3.0 | | | | |
| Neo Heliopan ® HMS | Homosalate | | | | | | | | | 5.0 | | | | |
| Neo Heliopan ® Hydro. 25% Lsg. Neutralised using Biotive L-Arginin | Phenyl benzimidazole Sulfonic Acid | | | | | | | | 3.0 | 8.0 | | | | |
| Neo Heliopan ® AP. 10% Lsg.. neutralized usingNAOH | Disodium Phenyl Dibenzimidazole Tetrasulfonate | | | | | | | | 3.0 | 13.3 | | | | |
| Neo Heliopan ® OS | Ethylhexyl Salicylate | | | | | | | | 5.0 | | | | | |
| Neutral oil | Caprylic/Capric Triglyceride | | | | | | | | 3.5 | | | 5.0 | | |
| Ozokerite Wax 2389 | Ozokerite | | | | | | | | | | | | 2.0 | |
| PCL-Liquid 100 | Cetearyl Ethyl hexanoate | | | 3.0 | | 1.0 | | | | | | | | |
| Pemulen TR-2 | Acrylates/Cl 0-30 Alkylacrylate Crosspolymer | | | | | | | | 0.3 | | | 0.3 | | |
| Polymer JR400 | Polyquatemium-10 | | 0.3 | | | | | | | | | | | |
| Polyquart H81 | PEG-15 Coco Poly-amine | | | | | | | | | | | | | 3.0 |
| Propane Butane 2.7 bar | Propane. Butane | 70.4 | | | | 48 | | | | | | | | |
| Propylene glycol | Propylene Glycol | | | | | | 36.5 | | 3.0 | 4.0 | | | | |
| Rezal 36 GP | Aluminum Zirconium Tetrachlorohydrex GLY | | | | | | | | | 5.0 | | | | |
| Softisan 100 | Hydrogenated Co-co Glycerides | | | | | | | | | 1.5 | | | | |
| Solubilizer | PEG-40 Hydro-genated Castor Oil. Trideceth-9. Pro-pylene Glycol. Water (Aqua) | | 0.5 | | 1.0 | 1.0 | | | | | | | | |
| Squalan herbal | Squalane | | | | | | | | | | 3.0 | | | |
| SymAmide UDA | Undecylenamide DEA. Diethanol-amine | | | | | 1.0 | | | | | | | | |
| SymCalmin ® | Pentylene Glycol. Butylene Glycol. Hydroxy phenyl Propamidobenzoic Acid | | | 0.5 | | | | | | | 1.0 | | | |
| SymClariol ® | Decylene Glycol | 0.5 | | | | 0.5 | | | | | | | | |
| SymDeo ® MPP | Dimethyl Phenyl butanol | 0.5 | | | | | | 0.5 | | | | | | |
| SymDiol ® 68 | 1.2 Hexanediol. Caprylyl Glycol | | | | | | | | | | 1.0 | | | |
| SymGlucan ® | Water (Aqua) Glycerin. Beta Glucan | | | | | | | | | | | 1.0 | | |
| SymMollient ® W/S | Trideceth-9. PEG-5 Isononanoate | | | | 1.0 | 0.5 | | | | | 0.5 | | | |
| SymRelief ® | Bisabolol. Zingiber Officinale (Ginger) Root Extract | | 0.2 | 0.2 | | | | | | | 0.2 | | | |
| SymRepair ® | Hexyl decanol. Bisabolol. Cetyl hydroxyl proline | | | | | | | | | | 2.0 | 3.0 | | |

-continued

| Ingredient | INCI-Name | 15 | 16 | 17 | 18 | 19 | 20 | 21 | 22 | 23 | 24 | 25 | 26 | 27 |
|---|---|---|---|---|---|---|---|---|---|---|---|---|---|---|
| SymVital ® | Palmitamide. Stearic Acid. *Brassica Campestris* (Rapeseed sterols) *Aloe Barbadensis* Leaf Juice Powder. Magnesium Ascorbyl Phosphate. *Rubus Idaeus* (Raspberry) Leaf Extract | | | 0.1 | | | | | 0.3 | | | | | |
| Triethanoiamin 99% | Triethanolamine | | | | | | | | | | 0.4 | 0.3 | | |
| Vitamin E Acetat | Tocopherol Acetate | | | 0.5 | | | | | | 0.5 | | | 0.2 | |
| Water | Water (Aqua) | | | | | | Ad 100 | | | | | | | |

15 = Aerosol Deo-Spray
16 = Shower gel
17 = After Shave Balm
18 = Eau de Toilette
19 = Foot Spray
20 = Deo Stick
21 = Deo APP Roll on Emulsion
22 = Deo Cream O/W (SPF = 15)
23 = Sun Lotion 8SPF = 25)
24 = After Sun Spray
25 = After Shave
26 = Cream w/o
27 = Hair Conditioner In all of the formulation examples, the cooling effect as perceived by the test persons was enhanced in relation to comparable formulations which did not contain any C3-C12 alkanediols and alkanetriols. Provided the corresponding formulations also contained trans-4-tert. butylcyclohexanol, the cooling effect was even further enhanced compared to formulations without this compound.

It has further been shown in practice that comparable effects are achieved if in each of these above-mentioned formulations, the proportion of 1,2-pentanediol is replaced with 1,2-hexanediol at a ratio of 5:3.

The same applies to the replacement of 1,2-pentanedial with 1,2-octanediol.

This applies analogously also to the replacement of 1,2-pentanedial with 1,2-decanediol, however, the latter is only used in an amount of one fifth of the pentanediol.

According to the present invention it is additionally to be expected that as a result of a replacement of 5-methyl-2-(propane-2-yl)cyclohexyl-N-ethyloxamate with other oxamates or other cooling substances such as for example 5-methyl-2-(propane-2-yl)cyclohexyl-N-methyl oxamate, a similar effect may be achieved.

5-methyl-2-(propane-2-yl)cyclohexyl-N-ethyloxamate has been used in the examples as cooling compound for exemplification of the specific effect of the invention. It has to be noted that this compound can be exchanged of partly exchanged with other physiologically cooling compounds and an analog effect or enhancement of the cooling sensation can be observed. It has further to be noted that the addition of compounds of group B, C, D, E and/or F would enhance the enhancing effect of the diols according to Group A in respective examples.

The breadth of formulations and the diversity of the examples shows that the enhancing cooling effect may be achieved over the entire range of cosmetics. As a result, a multiplicity of additional cooling mixtures and formulations will be accessible to a person skilled in the art.

What is claimed is:
1. A cooling mixture consisting of:
   (a) 5-methyl-2-(propane-2-yl)cyclohexyl-N-ethyloxamate (formula I)

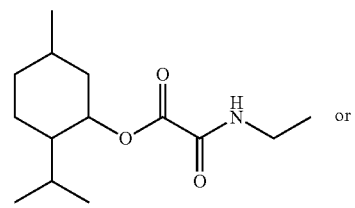 [SMILES: CCNC(=O)C(=O)OC1CC(C)CCC1C(C)C]

and
   (b) at least one 1,2-alkanediol selected from the group consisting of 1,2-hexanediol, 1,2-octanediol, 1,2-decanediol, 1,2-dodecanediol and mixtures thereof.
2. The mixture of claim 1, wherein at least part of the 5-methyl-2-(propane-2-yl)cyclohexyl-N-ethyloxamate is present in the (1R,2S,5R) configuration (formula II):

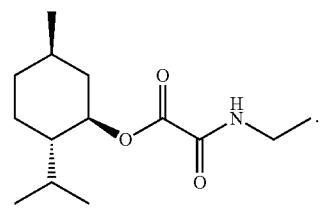 [SMILES: CCNC(=O)C(=O)O[C@@H]1C[C@H](C)CC[C@H]1C(C)C]

3. The mixture of claim 1, wherein the proportion of 5-methyl-2-(propane-2-yl)cyclohexyl-N-ethyloxamate present in the (1R,2S,5R) configuration in relation to the overall proportion of 5-methyl-2-(propane-2-yl)cyclohexyl-N-ethyloxamate is about 45%.

4. The mixture of claim 1, wherein component (b) is a mixture of 1,2-hexanediol and 1,2-octanediol.

5. The mixture of claim 1, wherein the ratio by weight between component (a) and component (b) is 1:20 to 1:0.1.

* * * * *